(12) United States Patent
Hogrefe et al.

(10) Patent No.: US 9,523,085 B2
(45) Date of Patent: Dec. 20, 2016

(54) THERMOSTABLE TYPE-A DNA POLYMERASE MUTANTS WITH INCREASED POLYMERIZATION RATE AND RESISTANCE TO INHIBITORS

(75) Inventors: Holly Hogrefe, San Diego, CA (US); Michelle Cayouette, San Diego, CA (US); Jeffrey Fox, Escondito, CA (US); Connie J. Hansen, San Diego, CA (US); Jennifer Lapira, San Diego, CA (US); Bahram Arezi, Carlsbad, CA (US); Nancy McKinney, San Diego, CA (US)

(73) Assignee: Agilent Technologies Inc., Loveland, CO (US)

( * ) Notice: Subject to any disclaimer, the term of this patent is extended or adjusted under 35 U.S.C. 154(b) by 1406 days.

(21) Appl. No.: 12/848,765

(22) Filed: Aug. 2, 2010

(65) Prior Publication Data

US 2011/0027833 A1 Feb. 3, 2011

Related U.S. Application Data

(60) Provisional application No. 61/230,275, filed on Jul. 31, 2009.

(51) Int. Cl.
*C12N 9/12* (2006.01)
*C12P 19/34* (2006.01)

(52) U.S. Cl.
CPC .................................. *C12N 9/1252* (2013.01)

(58) Field of Classification Search
None
See application file for complete search history.

(56) References Cited

U.S. PATENT DOCUMENTS

2009/0142754 A1 6/2009 Allawi
2009/0305292 A1 12/2009 Holliger et al.

FOREIGN PATENT DOCUMENTS

WO 2008034110 3/2008
WO 2010062777 6/2010

OTHER PUBLICATIONS

Ngo et al. in the Protein Folding Problem and Tertiary Structure Prediction, 1994, Merz et al. (ed.), Birkhauser, Boston, MA, pp. 433 and 492-495.*
Kermekchiev et al., "Mutants of Taq DNA polymerase resistant to PCR inhibitors allow DNA amplication from whole blood and cure soil samples," Nucleic Acids Research (Apr. 1, 2009); 37(5):1-14.
Ma et al., "RNA Template-dependent 5' Nuclease Activity of Themus aquaticus and Thermus thermophilus DNA Polymerases," The Journal of Biological Chemistry (Aug. 11, 2000); 275(32):24693-24700.
Lee et al., "Thermus aquaticus DNA polymerase," retrieved from EBI accession No. GSP:ABR43331 Dtabase accession No. ABR43331 Jul. 17, 2003.
Arezi et al., "Compartmentalized self-replication under fast PCR cycling conditions yields Taq DNA polymerase mutants with increased DNA-binding affinity and blood resistance," Frontiers in Microbiology (Aug. 14, 2014); vol. 5, Article 408:1-10.

* cited by examiner

*Primary Examiner* — Richard Hutson
(74) *Attorney, Agent, or Firm* — Fox Rothschild LLP

(57) ABSTRACT

The present invention provides mutants of DNA polymerases having an increased rate of incorporation of nucleotides into nucleic acids undergoing polymerization and having an enhanced resistance to inhibitors of DNA polymerase activity. The mutant polymerases are well suited for fast PCR applications, for PCR amplification of targets in samples that contain inhibitors of wild-type polymerases, and for fast PCR amplification of samples containing DNA polymerase inhibitors. In exemplary embodiments, the mutants are mutants of Taq DNA polymerase.

18 Claims, 21 Drawing Sheets

Figure 1

```
CLUSTAL 2.0.10 multiple sequence alignment

Thermus.Thermophilus.HB8        MEAMLPLFEPKGRVLLVDGHHLAYRTFFALKG-LTTSRGEPVQAVYGFAK 49
Thermus.caldophilus             MEAMLPLFEPKGRVLLVDGHHLAYRTFFALKG-LTTSRGEPVQAVYGFAK 49
Thermus.thermophilus.HB27       MEAMLPLFESKGRVLLVDGHHLAYRTFFALKG-LTTSRGEPVQAVYGFAK 49
Thermus.aquaticus               MRGMLPLFEPKGRVLLVDGHHLAYRTFHALKG-LTTSRGEPVQAVYGFAK 49
Thermus.scotoductus             MRAMLPLFEPKGRVLLVDGHHLAYRTFHALKG-LTTSRGEPVQAVYGFAK 49
Thermus.flavus                  -MAMLPLFEPKGRVLLVDGHHLAYRTFFALKG-LTTSRGEPVQAVYGFAK 48
Thermus.oshimai                 ---MLPLFEPKGRVLLVDGHHLAYRTFFALKG-LTTSRGEPVQAVYDFAK 46
Thermus.filiformis              MTPLFDLEEPPKRVLLVDGHHLAYRTFYALS--LTTSRGEPVQMVYGFAR 48
Thermotoga.maritima.MSB8        ----------MARLFLFDGTALAYRAYYALDRSLSTSTGIPTNATYGVAR 40
Thermotoga.neapolitana.DSM4359  ----------MARLFLFDGTALAYRAYYALDRSLSTSTGIPTNAVYGVAR 40
                                          *::*.**  ****::.**.  *:** * *.: .*..*:

Thermus.Thermophilus.HB8        SLLKALKEDGY---KAVFVVFDAKAPSFRHEAYEAYKAGRAPTPEDFPRQ 96
Thermus.caldophilus             SLLKALKEDGY---KAVFVVFDAKAPSFRHEAYEAYKAGRAPTPEDFPRQ 96
Thermus.thermophilus.HB27       SLLKALKEDGY---KSVFVVFDAKAPSFRHEAYEAYKAGRAPTPEDFPRQ 96
Thermus.aquaticus               SLLKALKEDG-----DAVIVVFDAKAPSFRHEAYGGYKAGRAPTPEDFPRQ 95
Thermus.scotoductus             SLLKALKEDG----DVVIVVFDAKAPSFRHQTYEAYKAGRAPTPEDFPRQ 95
Thermus.flavus                  SLLKALKEDG----DVVVVVFDAKAPSFRHEAYEAYKAGRAPTPEDFPRQ 94
Thermus.oshimai                 SLLKALKEDG----EVAIVVFDAKAPSFRHEAYEAYKAGRAPTPEDFPRQ 92
Thermus.filiformis              SLLKALKEDG----QAVVVVFDAKAPSFRHEAYEAYKAGRAPTPEDFPRQ 94
Thermotoga.maritima.MSB8        MLVRFIKDHIIVGKDYVAVAFDKKAATFRHKLLETYKAQPPKTPDLLIQQ 90
Thermotoga.neapolitana.DSM4359  MLVKFIKEHIIPEKDYAAVAFDKKAATFRHKLLEAYKAQRPKTPDLLVQQ 90
                                *::  :::.    . .*.**  **.:***:   *** *. **: : :*

Thermus.Thermophilus.HB8        LALIKELVDLLGFTRLEVPGYEADDVLATLAKKAEKEGYEVRILTADRDL 146
Thermus.caldophilus             LALIKELVDLLGFTRLEVPGYEADDVLATLAKNPEKEGYEVRILTADRDL 146
Thermus.thermophilus.HB27       LALIKELVDLLGFTRLEVPGYEADDVLATLAKKAEKEGYEVRILTADRDL 146
Thermus.aquaticus               LALIKELVDLLGLARLEVPGYEADDVLASLAKKAEKEGYEVRILTADKDL 145
Thermus.scotoductus             LALIKEMVDLLGLERLEVPGFEADDVLATLAKKAEKEGYEVRILTADRDL 145
Thermus.flavus                  LALIKELVDLLGLVRLEVPGFEADDVLATLAKRAEKEGYEVRILTADRDL 144
Thermus.oshimai                 LALIKELVDLLGLVRLEVPGFEADDVLATLAKKAEREGYEVRILSADRDL 142
Thermus.filiformis              LALVKRLVDLLGLVRLEAPGYEADDVLGTLAKKAEREGMEVRILTGDRDF 144
Thermotoga.maritima.MSB8        LPYIKKLVEALGMKVLEVEGYEADDIIATLAVKGLPLFDEIFIVTGDKDM 140
Thermotoga.neapolitana.DSM4359  LPYIKRLIEALGFKVLELEGYEADDIIATLAVRGCTFFDEIFIITGDKDM 140
                                *. :*.::: **:  ** *:****::.:**.       *: *::.*:*:

Thermus.Thermophilus.HB8        YQLVSDRVAVLHPEG-----HLITPEWLWEKYGLRPEQWVDFRALVGDPS 191
Thermus.caldophilus             DQLVSDRVAVLHPEG-----HLITPEWLWQKYGLKPEQWVDFRALVGDPS 191
Thermus.thermophilus.HB27       YQLVSDRVAVLHPEG-----HLITPEWLWEKYGLRPEQWVDFRALVGDPS 191
Thermus.aquaticus               YQLLSDRIHVLHPEG-----YLITPAWLWEKYGLRPDQWADYRALTGDES 190
Thermus.scotoductus             YQLLSERISILHPEG-----YLITPEWLWEKYGLKPSQWVDYRALAGDPS 190
Thermus.flavus                  YQLLSERIAILHPEG-----YLITPAWLYEKYGLRPEQWVDYRALAGDPS 189
Thermus.oshimai                 YQLLSDRIHLLHPEG-----EVLTPGWLQERYGLSPERWVEYRALVGDPS 187
Thermus.filiformis              FQLLSEKVSVLLPDG-----TLVTPKDVQEKYGVPPERWVDFRALTGDRS 189
Thermotoga.maritima.MSB8        LQLVNEKIKVWRIVKGISDLELYDAQKVREKYGVEPQQIPDLLALTGDEI 190
Thermotoga.neapolitana.DSM4359  LQLVNEKIKVWRIVKGISDLELYDSKKVKERYGVEPHQIPDLLALTGDEI 190
                                ::.::: :         :  .   ::**: * :   **.**
```

Figure 1 (cont.)

```
Thermus.Thermophilus.HB8        DNLPGVKGIGEKTALKLLKEWGSLENLLKNLDRVKPENVREKIKAHLEDL 241
Thermus.caldophilus             DNLPGVKGIGEKTALKLLKEWGSLENLLKNLDRVKPENVREKIKAHLEDL 241
Thermus.thermophilus.HB27       DNLPGVKGIGEKTALKLLKEWGSLESLLKNLDRVKPENVREKIKAHLEDL 241
Thermus.aquaticus               DNLPGVKGIGEKTARKLLEEWGSLEALLKNLDRLKP-AIREKILAHMDDL 239
Thermus.scotoductus             DNIPGVKGIGEKTAAKLIREWGSLENLLKHLEQVKPASVREKILSHMEDL 240
Thermus.flavus                  DNIPGVKGIGEKTAQRLIREWGSLENLFQHLDQVKPS-LREKLQAGMEAL 238
Thermus.oshimai                 DNLPGVPGIGEKTALKLLKEWGSLEAILKNLDQVKPERVREAIRMNLDKL 237
Thermus.filiformis              DNIPGVAGIGEKTALRLLAEWGSVENLLKNLDRVKPDSVRRKIEAHLEDL 239
Thermotoga.maritima.MSB8        DNIPGVTGIGEKTAVQLLEKYKDLEDILNHVR-ELPQKVRKALLRDRENA 239
Thermotoga.neapolitana.DSM4359  DNIPGVTGIGEKTAVQLLGKYRNLEDILEHAR-ELPQRVRKALLRDREVA 239
                                **:*** ******* :*: :: .:* ::::      * :*. :   :

Thermus.Thermophilus.HB8        RLSLELSRVRTDLPLEVDLA--QGREPDREGLRAFLERLEFGSLLHEFGL 289
Thermus.caldophilus             RLSLELSRVRTDLPLEVDLA--QGREPDREGLRAFLERLEFGSLLHEFGL 289
Thermus.thermophilus.HB27       RLSLELSRVRADLPLEVDLA--QGREPDREGLRAFLERLEFGSLLHEFGL 289
Thermus.aquaticus               KLSWDLAKVRTDLPLEVDFA--KRPEPDRERLRAFLERLEFGSLLHEFGL 287
Thermus.scotoductus             KLSLELSRVRTDLPLQVDFA--RRPEPDREGLKAFLERLEFGSLLHEFGL 288
Thermus.flavus                  ALSRKLSQVHTDLPLEVDFG--RRRTPNLEGLRAFLERLEFGSLLHEFGL 286
Thermus.oshimai                 QMSLELSRLRTDLPLEVDFA--KRREPDWEGLKAFLERLEFGSLLHEFGL 285
Thermus.filiformis              RLSLDLARIRTDLPLEVDFKALRRRTPDLEGLRAFLEELEFGSLLHEFGL 289
Thermotoga.maritima.MSB8        ILSKKLAILETNVPIEINWEELRYQGYDREKLLPLLKELEFASIMKELQL 289
Thermotoga.neapolitana.DSM4359  ILSKKLATLVTNAPVEVDWEEMKYRGYDKRKLLPILKELEFASIMKELQL 289
                                :* .*: : :: *::::    :  :  :. *..:*:.***.*:::*: *

Thermus.Thermophilus.HB8        LEAPAPL-----------EEAPWPPPE--GAFVGFVLSRPEPMWAELKAL 326
Thermus.caldophilus             LEAPAPL-----------EEAPWPPPE--GAFVGFVLSRPEPMWAELKAL 326
Thermus.thermophilus.HB27       LEAPTPL-----------EEAPWPPPE--GAFVGFVLSRPEPMWAELKAL 326
Thermus.aquaticus               LESPKAL-----------EEAPWPPPE--GAFVGFVLSRKEPMWADLLAL 324
Thermus.scotoductus             LESPVAA-----------EEAPWPPPE--GAFVGYVLSRPEPMWAELNAL 325
Thermus.flavus                  LEGPKAA-----------EEAPWPPPE--GAFLGFSFSRPEPMWAELLAL 323
Thermus.oshimai                 LEAPKEA-----------EEAPWPPPG--GAFLGFLLSRPEPMWAELLAL 322
Thermus.filiformis              LGGEKPR-----------EEAPWPPPE--GAFVGFLLSRKEPMWAELLAL 326
Thermotoga.maritima.MSB8        YEESEPVGYRIVKDLVEFEKLIEKLRESPSFAIDLETSSLDPFDCDIVGI 339
Thermotoga.neapolitana.DSM4359  YEEAEPTGYEIVKDHKTFEDLIEKLKEVPSFALDLETSSLDPFNCEIVGI 339
                                                *.    . :.    *  :*:  .:: .:

Thermus.Thermophilus.HB8        AACRDGR-------VHRAADPLAGLKDLKEVRGLLAK------------D 357
Thermus.caldophilus             AACRDGR-------VHRAADPLAGLKDLKEVRGLLAK------------D 357
Thermus.thermophilus.HB27       AACRDGR-------VHRAEDPLAGLGDLEEVRGLLAK------------D 357
Thermus.aquaticus               AAARGGR-------VHRAPEPYKALRDLKEARGLLAK------------D 355
Thermus.scotoductus             AAAWEGR-------VYRAEDPLEALRGLGEVRGLLAK------------D 356
Thermus.flavus                  AGAWEGR-------LHRAQDPLRGLRDLKGVRGILAK------------D 354
Thermus.oshimai                 AGAKEGR-------VHRAEDPVGALKDLKEIRGLLAK------------D 353
Thermus.filiformis              AAAAEGR-------VHRATSPVEALADLKEARGFLAK------------D 357
Thermotoga.maritima.MSB8        SVSFKPKEAYYIPLHHRNAQNLDEKEVLKKLKEILEDPGAKIVGQNLKFD 389
Thermotoga.neapolitana.DSM4359  SVSFKPKTAYYIPLHHRNAQNLDETLVLSKLKEILEDPSSKIVGQNLKYD 389
                                :  . :        :*  .      *  :;*  .              *
```

Figure 1 (cont.)

```
Thermus.Thermophilus.HB8        LAVLASREGLDLVPGDDPMLLAYLLDPS--NTTPEGVARRYGG------- 398
Thermus.caldophilus             LAVLASREGLDLVPGDDPMLLAYLLDPS--NTTPEGVARRYGG------- 398
Thermus.thermophilus.HB27       LAVLALREGLDLAPGDDPMLLAYLLDPS--NTTPEGVARRYGG------- 398
Thermus.aquaticus               LSVLALREGLGLPPGDDPMLLAYLLDPS--NTTPEGVARRYGG------- 396
Thermus.scotoductus             LAVLALREGIALAPGDDPMLLAYLLDPS--NTAPEGVARRYGG------- 397
Thermus.flavus                  LAVLALREGLDLFPEDDPMLLAYLLDPS--NTTPEGVARRYGG------- 395
Thermus.oshimai                 LSVLALREGREIPPGDDPMLLAYLLDPG--NTNPEGVARRYGG------- 394
Thermus.filiformis              LAVLALREGVALDPTDDPLLVAYLLDPA--NTNPEGVARRYGG------- 398
Thermotoga.maritima.MSB8        YKVLMVKGVEPVPPYFDTMIAAYLLEPNEKKFNLDDLALKFLGYKMTSYQ 439
Thermotoga.neapolitana.DSM4359  YKVLMVKGISPVYPHFDTMIAAYLLEPNEKKFNLEDLSLKFLGYKMTSYQ 439
                                **  :     : * *.:: ****;*    :  :.:: :: *

Thermus.Thermophilus.HB8        --------------------EWTEDAAHRALLSERLHRNLLKRLEGEEKL 428
Thermus.caldophilus             --------------------EWTEDAAHRALLSERLHRNLLKRLQGEEKL 428
Thermus.thermophilus.HB27       --------------------EWTEDAAHRALLSERLHRNLLKRLEGEEKL 428
Thermus.aquaticus               --------------------EWTEEAGERAALSERLFANLWGRLEGEERL 426
Thermus.scotoductus             --------------------EWTEEAGERALLSERLYAALLERLKGEERL 427
Thermus.flavus                  --------------------EWTEDAGERALLAERLFQTLKEPLKGEERL 425
Thermus.oshimai                 --------------------EWKEDAAARALLSERLWQALYPPVAEEERL 424
Thermus.filiformis              --------------------EFTEDAAERALLSERLFQNLFPRLS--EKL 426
Thermotoga.maritima.MSB8        ELMSFSFPLFGFSFADVPVEKAANYSCEDADITYRLYKTLSLKLH-EADL 488
Thermotoga.neapolitana.DSM4359  ELMSFSSPLFGFSFADVPVDKAANYSCEDADITYRLYKILSMKLH-EAEL 488
                                   :  :    * :: ** *  ::       *

Thermus.Thermophilus.HB8        LWLYHEVEKPLSRVLAHMEATGVRLDVAYLQALSLELAEEIRRLEEEVFR 478
Thermus.caldophilus             LWLYHEVEKPLSRVLAHMEATGVRLDVAYLQALSLELAEEIRRLEEEVFR 478
Thermus.thermophilus.HB27       LWLYHEVEKPLSRVLAHMEATGVRLDVAYLQALSLELAEEIRRLEEEVFR 478
Thermus.aquaticus               LWLYREVERPLSAVLAHMEATGVRLDVAYLRALSLEVAEEIARLEAEVFR 476
Thermus.scotoductus             LWLYEEVERPLSRVLAHMEATGVRLDVAYLKALSLEVEAELRRLEEEVHR 477
Thermus.flavus                  LWLYEEVEKPLSRVLARMEATGVRLDVAYLQALSLEVEAEVRQLEEEVFR 475
Thermus.oshimai                 LWLYREVERPLAQVLAHMEATGVRLDVPYLEALSQEVAFELERLEAEVHR 474
Thermus.filiformis              LWLYQEVERPLSRVLAHMEARGVRLDVPLLEALSFELEKEMERLEGEVFR 476
Thermotoga.maritima.MSB8        ENVFYKIEMPLVNVLARMELNGVYVDTEFLKKLSEEYGKKLEELAEEIYR 538
Thermotoga.neapolitana.DSM4359  ENVFYRIEMPLVNVLARMELNGVYVDTEFLKKLSEEYGKKLEELAEKIYQ 538
                                ::  .:* ** ***:** ** :*. *. ** *   :: .*  ::.:

Thermus.Thermophilus.HB8        LAGHPFNLNSRDQLERVLFDELRLPALGKTQKTGKRSTSAAVLEALREAH 528
Thermus.caldophilus             LAGHPFNLNSRDQLERVLFDELRLPALGKTQKTGKRSTSAAVLEALREAH 528
Thermus.thermophilus.HB27       LAGHPFNLNSRDQLERVLFDELRLPALGKTQKTGKRSTSAAVLEALREAH 528
Thermus.aquaticus               LAGHPFNLNSRDQLERVLFDELGLPAIGKTEKTGKRSTSAAVLEALREAH 526
Thermus.scotoductus             LAGHPFNLNSRDQLERVLFDELGLPAIGKTEKTGKRSTSAAVLEALREAH 527
Thermus.flavus                  LAGHPFNLNSRDQLERVLFDELGLPAIGKTEKTGKRSTSAAVLEALREAH 525
Thermus.oshimai                 LAGHPFNLNSRDQLERVLFDELGLPPIGKTEKTGKRSTSAAVLELLREAH 524
Thermus.filiformis              LAGHPFNLNSRDQLERVLFDELGLTPVGRTEKTGKRSTAQGALEALRGAH 526
Thermotoga.maritima.MSB8        IAGEPFNINSPKQVSRILFEKLGIKPRGKTTKTGDYSTRIEVLEELAGEH 588
Thermotoga.neapolitana.DSM4359  IAGEPFNINSPKQVSKILFEKLGIKPRGKTTKTGEYSTRIEVLEEIANEH 588
                                :**.***:**  .*:.;:**::* :  *;* ***. **   .** :   *
```

Figure 1 (cont.)

```
Thermus.Thermophilus.HB8         PIVEKILQHRELTKLKNTYVDPLPSLVHPRTGRLHTRFNQTATATGRLSS 578
Thermus.caldophilus              PIVEKILQHRELTKLKNTYVDPLPSLVHPNTGRLHTRFNQTATATGRLSS 578
Thermus.thermophilus.HB27        PIVEKILQHRELTKLKNTYVDPLPSLVHPRTGRLHTRFNQTATATGRLSS 578
Thermus.aquaticus                PIVEKILQYRELTKLKSTYIDPLPDLIHPRTGRLHTRFNQTATATGRLSS 576
Thermus.scotoductus              PIVDRILQYRELSKLKGTYIDPLPALVHPKTNRLHTRFNQTATATGRLSS 577
Thermus.flavus                   PIVDRILQYRELTKLKNTYIDPLPALVHPKTGRLHTRFNQTATATGRLSS 575
Thermus.oshimai                  PIVGRILEYRELMKLKSTYIDPLPRLVHPKTGRLHTPFNQTATATGRLSS 574
Thermus.filiformis               PIVELILQYRELSKLKSTYLDPLPRLVHPRTGRLHTRFNQTATATGRLSS 576
Thermotoga.maritima.MSB8         EIIPLILEYRKIQKLKSTYIDALPKMVNPKTGRIHASFNQTGTATGRLSS 638
Thermotoga.neapolitana.DSM4359   EIVPLILEYRKIQKLKSTYIDTLPKLVNPKTGRIHASFHQTGTATGRLSS 638
                                 *:   **::*:: ***.**:*.** :::*.*.*:*: *:**.********

Thermus.Thermophilus.HB8         SDPNLQNIPVRTPLGQRIRRAFVAEAG-WALVALDYSQIELRVLAHLSGD 627
Thermus.caldophilus              SDPNLQNIPVRTPLGQRIRRAFVAEAG-WALVALDYSQIELRVLAHLSGD 627
Thermus.thermophilus.HB27        SDPNLQNIPVRTPLGQRIRRAFVAEAG-WALVALDYSQIELRVLAHLSGD 627
Thermus.aquaticus                SDPNLQNIPVRTPLGQRIRRAFIAEEG-WLLVALDYSQIELRVLAHLSGD 625
Thermus.scotoductus              SDPNLQNIPVRTPLGQRIRRAFVAEEG-WRLVVLDYSQIELRVLAHLSGD 626
Thermus.flavus                   SDPNLQNIPVRTPLGQRIRRAFVAEEG-WVLVVLDYSQIELRVLAHLSGD 624
Thermus.oshimai                  SDPNLQNIPVRTPLGQRIRKAFIAEEG-HLLVALDYSQIELRVLAHLSGD 623
Thermus.filiformis               SDPNLQNIPVRTPLGQRIRKAFVAEEG-WLLLAADYSQIELRVLAHLSGD 625
Thermotoga.maritima.MSB8         SDPNLQNLPTKSEEGKEIRKAIVPQDPNMWIVSADYSQIELRILAHLSGD 688
Thermotoga.neapolitana.DSM4359   SDPNLQNLPTKSEEGKEIRKAIVPQDPDWWIVSADYSQIELRILAHLSGD 688
                                 *******:*.:: *:.**:*::.:     :: ********:*******

Thermus.Thermophilus.HB8         ENLIRVFQEGKDIHTQTASWMFGVPPEAVDPLMRRAAKTVNFGVLYGMSA 677
Thermus.caldophilus              ENLIRVFQEGKDIHTQTASWMFGVPPEAVDPLMRRAAKTVNFGVLYGMSA 677
Thermus.thermophilus.HB27        ENLIRVFQEGKDIHTQTASWMFGVPPEAVDPLMRRAAKTVNFGVLYGMSA 677
Thermus.aquaticus                ENLIRVFQEGRDIHTETASWMFGVPREAVDPLMRRAAKTINFGVLYGMSA 675
Thermus.scotoductus              ENLIRVFQEGQDIHTQTASWMFGVPPEAVDSLMRRAAKTINFGVLYGMSA 676
Thermus.flavus                   ENLIRVFQEGRDIHTQTASWMFGVSPEGVDPLMRRAAKTINFGVLYGMSA 674
Thermus.oshimai                  ENLIRVFREGKDIHTETAAWMFGVPPEGVDGAMRRAAKTVNYGVLYGMSA 673
Thermus.filiformis               ENLKRVFREGKDIHTETAAWMFGLDPALVDPKMRRAAKTVNFGVLYGMSA 675
Thermotoga.maritima.MSB8         ENLLRAFEEGIDVHTLTASRIFNVKPEEVTEEMRRAGKMVNFSIIYGVTP 738
Thermotoga.neapolitana.DSM4359   ENLVKAFEEGIDVHTLTASRIYNVKPEEVNEEMRRVGKMVNFSIIYGVTP 738
                                 ***   :.*.** *;** **: ::.:   *   ***..* :*:.::**:;.

Thermus.Thermophilus.HB8         HRLSQELAIPYEEAVAFIERYFQSFPKVRAWIEKTLEEGRKRGYVETLFG 727
Thermus.caldophilus              HRLSQELAIPYEEAVAFIERYFQSFPKVRAWIEKTLEEGRKRGYVETLFG 727
Thermus.thermophilus.HB27        HRLSQELAIPYEEAVAFIERYFQSFPKVRAWIEKTLEEGRKRGYVETLFG 727
Thermus.aquaticus                HRLSQELAIPYEEAQAFIERYFQSFPKVRAWIEKTLEEGRRRGYVETLFG 725
Thermus.scotoductus              HRLSQELAIPYEEAVAFIERYFQSYPKVRAWIEKTLAEGRERGYVETLFG 726
Thermus.flavus                   HRLSGELSIPYEEAVAFIERYFQSYPKVRAWIEGTLEEGRRRGYVETLFG 724
Thermus.oshimai                  HRLSQELSIPYEEAAAFIERYFQSFPKVRAWIAKTLEEGRKKGYVETLFG 723
Thermus.filiformis               HRLSQELGIDYKEAEAFIERYFQSFPKVRAUIERTLEEGRTRGYVETLFG 725
Thermotoga.maritima.MSB8         YGLSVRLGVPVKEAEKMIVNYFVLYPKVRDYIQRVVSEAKEKGYVRTLFG 788
Thermotoga.neapolitana.DSM4359   YGLSVRLGIPVKEAEKMIISYFTLYPKVRSYIQQVVAEAKEKGYVRTLFG 788
                                 : **.*.:  :** .*  **  :****  :*  .: *.:  :***.****
```

Figure 1 (cont.)

```
Thermus.Thermophilus.HB8          RRRYVPDLNARVKSVREAAERMAFNMPVQGTAADLMKLAMVKLFPRLR--  775
Thermus.caldophilus               RRRYVPDLNARVKSVREAAERMAFNMPVQGTAADLMKLAMVKLFPRLR--  775
Thermus.thermophilus.HB27         RRRYVPDLNARVKSVREAAERMAFNMPVQGTAADLMKLAMVKLFPRLR--  775
Thermus.aquaticus                 RRRYVPDLEAPVKSVREAAERMAFNMPVQGTAADLMKLAMVKLFPRLE--  773
Thermus.scotoductus               RRRYVPDLASRVKSIPEAAERMAFNMPVQGTAADLMKLAMVKLFPRLQ--  774
Thermus.flavus                    RRRYVPDLNARVKSVREAAERMAFNMPVQGTAADLMKLAMVRLFPRLQ--  772
Thermus.oshimai                   RRRYVPDLNARVKSVREAAERMAFNMPVQGTAADLMKLAMVRLFPRLR--  771
Thermus.filiformis                RRRYVPDLASRVRSVREAAERMAFNMPVQGTAADLMKIAMVKLFPRLK--  773
Thermotoga.maritima.MSB8          RKRDIPQLMARDRNTQAEGERIAINTPIQGTAADIIKLAMIEIDRELKER 838
Thermotoga.neapolitana.DSM4359    RKRDIPQLMARDKNTQSEGERIAINTPIQGTAADIIKLAMIDIDEELRKR 838
                                  *:*  :*:*  :*  :.  :   ,**:*;*  *;******::*:**;  :   .*.

Thermus.Thermophilus.HB8          EMGARMLLQVHDELLLEAPQAPAEEVAALAKEAMEKAYPLAVPLEVEVGM 825
Thermus.caldophilus               EMGARMLLQVHDELLLEAPQAGAEEVAALAKEAMEKAYPLAVPLEVEVGM 825
Thermus.thermophilus.HB27         EMGARMLLQVHDELLLEAPQAPAEEVAALAKEAMEKAYPLAVPLEVEVGM 825
Thermus.aquaticus                 EMGARMLLQVHDELVLEAPKERAEAVARLAKEVMEGVYPLAVPLEVEVGI 823
Thermus.scotoductus               ELGARMLLQVHDELVLEAPKEQAEEVAQEAKRTMEEVWPLKVPLEVEVGI 824
Thermus.flavus                    ELGARMLLQVHDELVLEAPKDRAERVAALAKEVMEGVWPLQVPLEVEVGL 822
Thermus.oshimai                   PLGVRILLQVHDELVLEAPKARAEEAAQLAKETMEGVYPLSVPLEVEVGM 821
Thermus.filiformis                PLGAHLLLQVHDELVLEVPEDRAEEAKALVKEVMENTYPLDVPLEVEVGV 823
Thermotoga.maritima.MSB8          KMRSKMIIQVHDELVFEVPNEEKDALVELVKDRMTNVVKLSVPLEVDVTI 888
Thermotoga.neapolitana.DSM4359    NMKSRMIIQVHDELVFEVPDEEKEELVDLVKNKMTNVVKLSVPLEVDISI 888
                                  :   ::::******;;*.*.   :    .* *  .  * ****;; :

Thermus.Thermophilus.HB8          GEDWLSAKG-  834   (SEQ ID NO:1)
Thermus.caldophilus               GEDWLSAKG-  834   (SEQ ID NO:2)
Thermus.thermophilus.HB27         GEDWLSAKG-  834   (SEQ ID NO:3)
Thermus.aquaticus                 GEDWLSAKE-  832   (SEQ ID NO:4)
Thermus.scotoductus               GEDWLSAKA-  833   (SEQ ID NO:5)
Thermus.flavus                    GEDWLSAKE-  831   (SEQ ID NO:6)
Thermus.oshimai                   GEDWLSAKA-  830   (SEQ ID NO:7)
Thermus.filiformis                GRDWLEAKGD  833   (SEQ ID NO:8)
Thermotoga.maritima.MSB8          GKTWS-----  893   (SEQ ID NO:9)
Thermotoga.neapolitana.DSM4359    GKSWS-----  893   (SEQ ID NO:10)
                                  *. *
```

Figure 5
(Replacement Sheet)
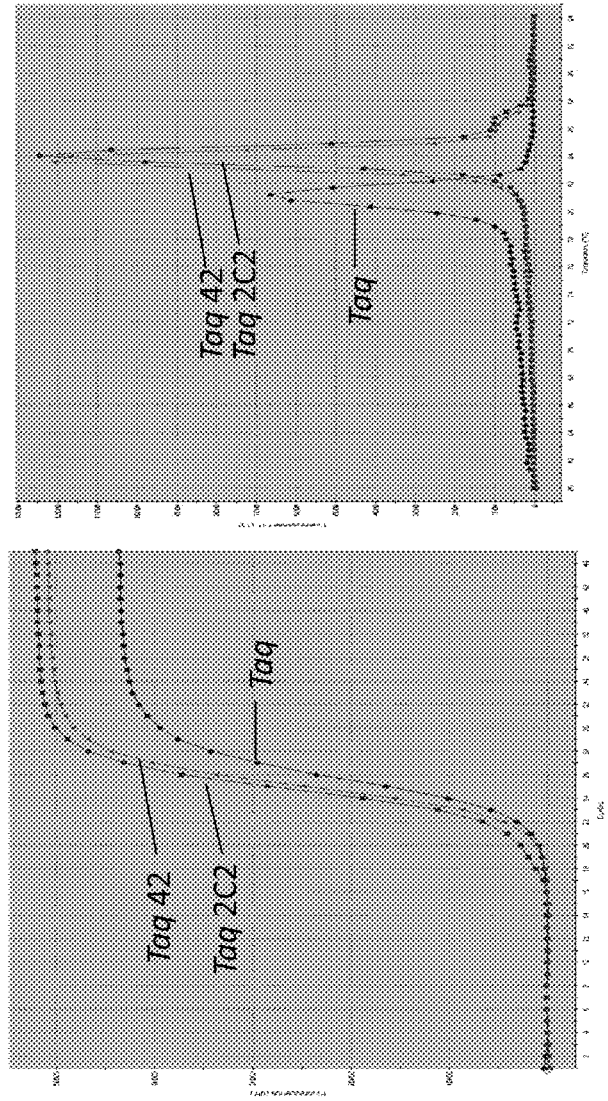

Figure 5, cont.
(Replacement Sheet)
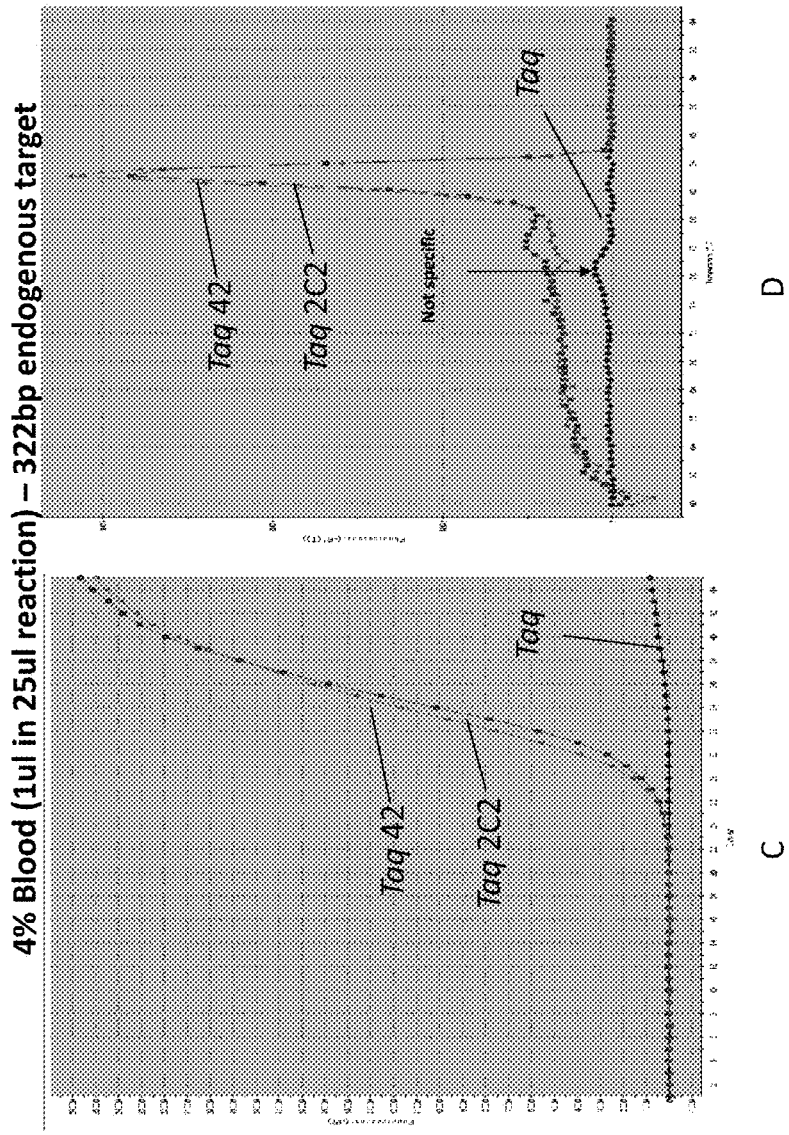

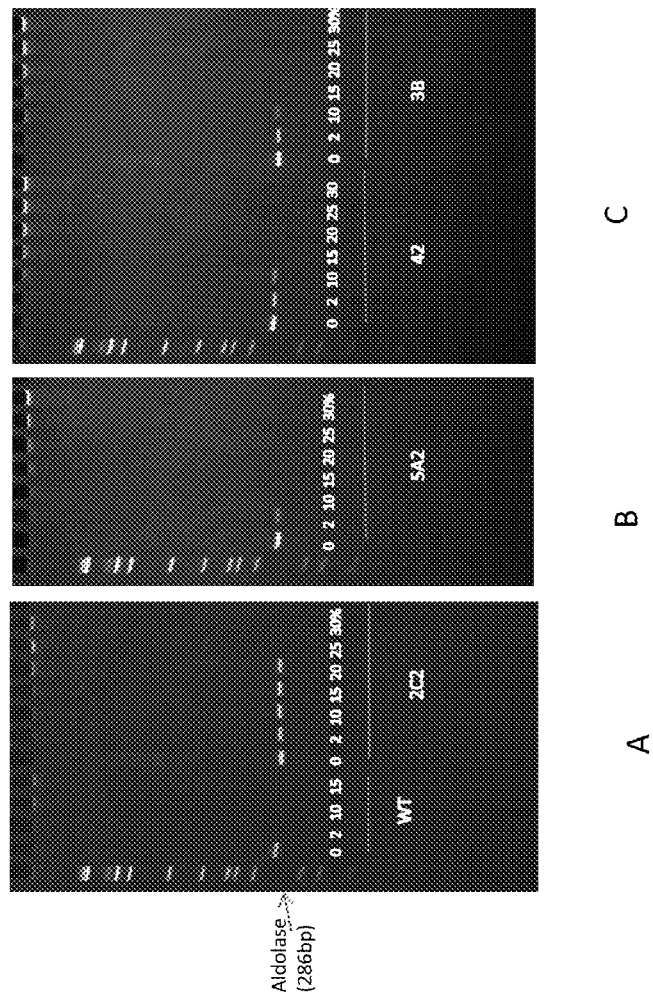
Figure 6
(Replacement Sheet)

Figure 7
(Replacement Sheet)
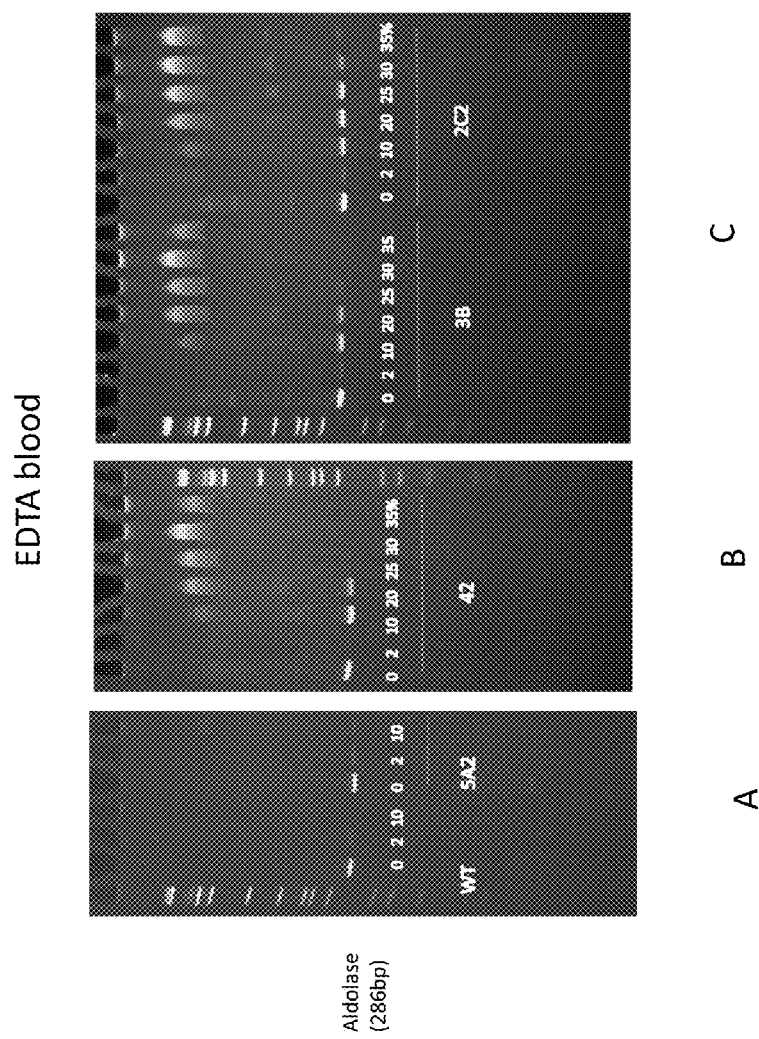

SEQUENCE LISTING

<160> NUMBER OF SEQ ID NOS: 39

<210> SEQ ID NO 1
<211> LENGTH: 832
<212> TYPE: PRT
<213> ORGANISM: Thermus thermophilus HB8

<400> SEQUENCE: 1

```
Met Glu Ala Met Leu Pro Leu Phe Glu Pro Lys Gly Arg Val Leu Leu
1               5                   10                  15

Val Asp Gly His His Leu Ala Tyr Arg Thr Phe Phe Ala Leu Lys Gly
            20                  25                  30

Leu Thr Thr Ser Arg Gly Glu Pro Val Gln Ala Val Tyr Gly Phe Ala
        35                  40                  45

Lys Ser Leu Leu Lys Ala Leu Lys Asp Asp Gly Tyr Lys Ala Val Phe
    50                  55                  60

Val Val Phe Asp Ala Lys Ala Pro Ser Phe Arg His Glu Ala Tyr Glu
65                  70                  75                  80

Ala Tyr Lys Ala Gly Arg Ala Pro Thr Pro Glu Asp Phe Pro Arg Gln
                85                  90                  95
```

```
Leu Ala Leu Ile Lys Glu Leu Val Asp Leu Gly Phe Thr Arg Leu
            100                 105                 110

Glu Val Gly Tyr Glu Ala Asp Val Leu Ala Thr Leu Ala Lys Lys
            115                 120                 125

Ala Glu Lys Glu Gly Tyr Glu Val Arg Ile Leu Thr Ala Asp Arg Asp
130                 135                 140

Leu Tyr Gln Leu Val Ser Asp Arg Val Ala Val Leu His Pro Glu Gly
145                 150                 155                 160

His Leu Ile Thr Pro Glu Trp Leu Trp Glu Lys Tyr Gly Leu Arg Pro
                165                 170                 175

Glu Gln Trp Val Asp Phe Arg Ala Leu Val Gly Asp Pro Ser Asp Asn
            180                 185                 190

Leu Pro Gly Val Lys Gly Ile Gly Glu Lys Thr Ala Leu Lys Leu Leu
            195                 200                 205

Lys Glu Trp Gly Ser Leu Glu Asn Leu Leu Lys Asn Leu Asp Arg Val
            210                 215                 220

Lys Pro Glu Asn Val Arg Glu Lys Ile Lys Ala His Leu Glu Asp Leu
225                 230                 235                 240

Arg Leu Ser Leu Glu Leu Ser Arg Val Arg Thr Asp Leu Pro Leu Glu
                245                 250                 255

Val Asp Leu Ala Gln Gly Arg Glu Pro Asp Arg Glu Gly Leu Arg Ala
            260                 265                 270

Phe Leu Glu Arg Leu Glu Phe Gly Ser Leu Leu His Glu Phe Gly Leu
            275                 280                 285

Leu Glu Ala Pro Ala Pro Leu Glu Glu Ala Pro Trp Pro Pro Pro Glu
            290                 295                 300

Gly Ala Phe Val Gly Phe Val Leu Ser Arg Pro Glu Pro Met Trp Ala
305                 310                 315                 320

Glu Leu Lys Ala Leu Ala Ala Cys Arg Asp Gly Arg Val His Arg Ala
                325                 330                 335

Ala Asp Pro Leu Ala Gly Leu Lys Asp Leu Lys Glu Val Arg Gly Leu
            340                 345                 350

Leu Ala Lys Asp Leu Ala Val Leu Ala Ser Arg Glu Gly Leu Asp Leu
            355                 360                 365

Val Pro Gly Asp Asp Pro Met Leu Leu Ala Tyr Leu Leu Asp Pro Ser
370                 375                 380

Asn Thr Thr Pro Glu Gly Val Ala Arg Arg Tyr Gly Gly Glu Trp Thr
385                 390                 395                 400

Glu Asp Ala Ala His Arg Ala Leu Leu Ser Glu Arg Leu His Arg Asn
                405                 410                 415

Leu Leu Lys Arg Leu Glu Gly Glu Glu Lys Leu Leu Trp Leu Tyr His
            420                 425                 430

Glu Val Glu Lys Pro Leu Ser Arg Val Leu Ala His Met Glu Ala Thr
            435                 440                 445

Gly Val Arg Leu Thr Val Ala Tyr Leu Gln Ala Leu Ser Leu Glu Leu
            450                 455                 460

Ala Glu Glu Ile Arg Arg Leu Glu Glu Val Phe Arg Leu Ala Gly
465                 470                 475                 480

His Pro Phe Asn Leu Asn Ser Arg Asp Gln Leu Glu Arg Val Leu Phe
                485                 490                 495

Asp Glu Leu Arg Leu Pro Ala Leu Gly Lys Thr Gln Lys Thr Gly Lys
            500                 505                 510
```

```
Arg Ser Thr Ser Ala Ala Val Leu Glu Ala Leu Arg Glu Ala His Pro
            515                 520                 525

Ile Val Glu Lys Ile Leu Gln His Arg Glu Leu Thr Lys Leu Lys Asn
    530                 535                 540

Thr Tyr Val Asp Pro Leu Pro Ser Leu Val His Pro Arg Thr Gly Arg
545                 550                 555                 560

Leu His Thr Arg Phe Asn Gln Thr Ala Thr Ala Thr Gly Arg Leu Ser
                565                 570                 575

Ser Ser Asp Pro Asn Leu Gln Asn Ile Pro Val Arg Thr Pro Leu Gly
            580                 585                 590

Gln Arg Ile Arg Arg Ala Phe Val Ala Glu Ala Gly Trp Ala Leu Val
    595                 600                 605

Ala Leu Asp Tyr Ser Gln Ile Glu Leu Arg Val Leu Ala His Leu Ser
610                 615                 620

Gly Asp Glu Asn Leu Ile Arg Val Phe Gln Glu Gly Lys Asp Ile His
625                 630                 635                 640

Thr Gln Thr Ala Ser Trp Met Phe Gly Val Pro Pro Glu Ala Val Asp
                645                 650                 655

Pro Leu Met Arg Arg Ala Ala Lys Thr Val Asn Phe Gly Val Leu Tyr
            660                 665                 670

Gly Met Ser Ala His Arg Leu Ser Gln Glu Leu Ala Ile Pro Tyr Glu
    675                 680                 685

Glu Ala Val Ala Phe Ile Glu Arg Tyr Phe Gln Ser Phe Pro Lys Val
690                 695                 700

Arg Ala Trp Ile Glu Lys Thr Leu Glu Glu Gly Arg Lys Arg Gly Tyr
705                 710                 715                 720

Val Glu Thr Leu Phe Gly Arg Arg Arg Tyr Val Pro Asp Leu Asn Ala
                725                 730                 735

Arg Val Lys Ser Val Arg Glu Ala Ala Glu Arg Met Ala Val Asn Met
            740                 745                 750

Pro Val Gln Gly Thr Ala Ala Asp Leu Met Lys Leu Ala Met Val Lys
    755                 760                 765

Leu Phe Pro Arg Leu Arg Glu Met Gly Ala Arg Met Leu Leu Gln Val
770                 775                 780

His Asp Glu Leu Leu Glu Ala Pro Gln Ala Arg Ala Glu Glu Val Ala
785                 790                 795                 800

Ala Leu Ala Lys Glu Ala Met Glu Lys Ala Tyr Pro Leu Ala Val Pro
                805                 810                 815

Leu Glu Val Glu Val Gly Met Gly Glu Asp Trp Leu Ser Ala Lys Gly
            820                 825                 830

<210> SEQ ID NO 2
<211> LENGTH: 835
<212> TYPE: PRT
<213> ORGANISM: Thermus caldophilus

<400> SEQUENCE: 2

Met Glu Ala Met Leu Pro Leu Phe Glu Pro Lys Gly Arg Val Leu Leu
1               5                   10                  15

Val Asp Gly His His Leu Ala Tyr Arg Thr Phe Phe Ala Leu Lys Gly
            20                  25                  30

Leu Thr Thr Ser Arg Gly Glu Pro Val Gln Ala Val Tyr Gly Phe Ala
        35                  40                  45

Lys Ser Leu Leu Lys Ala Leu Lys Glu Asp Gly Tyr Lys Ala Val Phe
    50                  55                  60
```

```
Val Val Phe Asp Ala Lys Ala Pro Ser Phe Arg His Glu Ala Tyr Glu
 65                  70                  75                  80

Ala Tyr Lys Ala Gly Arg Ala Pro Thr Pro Glu Asp Phe Pro Arg Gln
                 85                  90                  95

Leu Ala Leu Ile Lys Glu Leu Val Asp Leu Leu Gly Phe Thr Arg Leu
                100                 105                 110

Glu Val Pro Gly Tyr Glu Ala Asp Asp Val Leu Ala Thr Leu Ala Lys
                115                 120                 125

Asn Pro Glu Lys Glu Gly Tyr Glu Val Arg Ile Leu Thr Ala Asp Arg
            130                 135                 140

Asp Leu Asp Gln Leu Val Ser Asp Arg Val Ala Val Leu His Pro Glu
145                 150                 155                 160

Gly His Leu Ile Thr Pro Glu Trp Leu Trp Gln Lys Tyr Gly Leu Lys
                165                 170                 175

Pro Glu Gln Trp Val Asp Phe Arg Ala Leu Val Gly Asp Pro Ser Asp
                180                 185                 190

Asn Leu Pro Gly Val Lys Gly Ile Gly Glu Lys Thr Ala Leu Lys Leu
                195                 200                 205

Leu Lys Glu Trp Gly Ser Leu Glu Asn Leu Leu Lys Asn Leu Asp Arg
210                 215                 220

Val Lys Pro Glu Asn Val Arg Glu Lys Ile Lys Ala His Leu Glu Asp
225                 230                 235                 240

Leu Arg Leu Ser Leu Glu Leu Ser Arg Val Arg Thr Asp Leu Pro Leu
                245                 250                 255

Glu Val Asp Leu Ala Gln Gly Arg Glu Pro Asp Arg Glu Gly Leu Arg
                260                 265                 270

Ala Phe Leu Glu Arg Leu Glu Phe Gly Ser Leu Leu His Glu Phe Gly
                275                 280                 285

Leu Leu Glu Ala Pro Ala Pro Leu Glu Glu Ala Pro Trp Pro Pro Pro
            290                 295                 300

Glu Gly Ala Phe Val Gly Phe Val Leu Ser Arg Pro Glu Pro Met Trp
305                 310                 315                 320

Ala Glu Leu Lys Ala Leu Ala Ala Cys Arg Asp Gly Arg Val His Arg
                325                 330                 335

Ala Ala Asp Pro Leu Ala Gly Leu Lys Asp Leu Lys Glu Val Arg Gly
                340                 345                 350

Leu Leu Ala Lys Asp Leu Ala Val Leu Ala Ser Arg Glu Gly Leu Asp
                355                 360                 365

Leu Val Pro Gly Asp Asp Pro Met Leu Leu Ala Tyr Leu Leu Asp Pro
370                 375                 380

Ser Asn Thr Thr Pro Glu Gly Val Ala Arg Arg Tyr Gly Gly Glu Trp
385                 390                 395                 400

Thr Glu Asp Ala Ala His Arg Ala Leu Leu Ser Glu Arg Leu His Arg
                405                 410                 415

Asn Leu Leu Lys Arg Leu Gln Gly Glu Glu Lys Leu Leu Trp Leu Tyr
                420                 425                 430

His Glu Val Glu Lys Pro Leu Ser Arg Val Leu Ala His Met Glu Ala
                435                 440                 445

Thr Gly Val Arg Leu Thr Asp Val Ala Tyr Leu Gln Ala Leu Ser Leu
            450                 455                 460

Glu Leu Ala Glu Glu Ile Arg Arg Leu Glu Glu Glu Val Phe Arg Leu
465                 470                 475                 480
```

```
Ala Gly His Pro Phe Asn Leu Asn Ser Arg Asp Gln Leu Glu Arg Val
            485                 490                 495

Leu Phe Asp Glu Leu Arg Leu Pro Ala Leu Gly Lys Thr Gln Lys Thr
        500                 505                 510

Gly Lys Arg Ser Thr Ser Ala Ala Val Leu Glu Ala Leu Arg Glu Ala
            515                 520                 525

His Pro Ile Val Glu Lys Ile Leu Gln His Arg Glu Leu Thr Lys Leu
        530                 535                 540

Lys Asn Thr Tyr Val Asp Pro Leu Pro Ser Leu Val His Pro Asn Thr
545                 550                 555                 560

Gly Arg Leu His Thr Arg Phe Asn Gln Thr Ala Thr Ala Thr Gly Arg
                565                 570                 575

Leu Ser Ser Ser Asp Pro Asn Leu Gln Asn Ile Pro Val Arg Thr Pro
            580                 585                 590

Leu Gly Gln Arg Ile Arg Arg Ala Phe Val Ala Glu Ala Gly Trp Ala
        595                 600                 605

Leu Val Ala Leu Asp Tyr Ser Gln Ile Glu Leu Arg Val Leu Ala His
            610                 615                 620

Leu Ser Gly Asp Glu Asn Leu Ile Arg Val Phe Gln Glu Gly Lys Asp
625                 630                 635                 640

Ile His Thr Gln Thr Ala Ser Trp Met Phe Gly Val Pro Pro Glu Ala
                645                 650                 655

Val Asp Pro Leu Met Arg Arg Ala Ala Lys Thr Val Asn Phe Gly Val
            660                 665                 670

Leu Tyr Gly Met Ser Ala His Arg Leu Ser Gln Glu Leu Ala Ile Pro
        675                 680                 685

Tyr Glu Glu Ala Val Ala Phe Ile Glu Arg Tyr Phe Gln Ser Pro Arg
            690                 695                 700

Lys Val Arg Ala Trp Ile Glu Lys Thr Leu Glu Glu Gly Arg Lys Arg
705                 710                 715                 720

Gly Tyr Val Glu Thr Leu Phe Gly Arg Arg Arg Tyr Val Pro Asp Leu
                725                 730                 735

Asn Ala Arg Val Lys Ser Val Arg Glu Ala Ala Glu Arg Met Ala Phe
            740                 745                 750

Asn Met Pro Val Gln Gly Thr Ala Ala Asp Leu Met Lys Leu Ala Met
        755                 760                 765

Val Lys Leu Phe Pro Arg Leu Arg Glu Met Gly Ala Arg Met Leu Leu
        770                 775                 780

Gln Val His Asp Glu Leu Leu Leu Glu Ala Pro Gln Ala Gly Ala Glu
785                 790                 795                 800

Glu Val Ala Ala Leu Ala Lys Glu Ala Met Glu Lys Ala Tyr Pro Leu
                805                 810                 815

Ala Val Pro Leu Glu Val Glu Val Gly Met Gly Glu Asp Trp Leu Ser
            820                 825                 830

Ala Lys Gly
        835

<210> SEQ ID NO 3
<211> LENGTH: 835
<212> TYPE: PRT
<213> ORGANISM: Thermus thermophilus HB27

<400> SEQUENCE: 3

Met Glu Ala Met Leu Pro Leu Phe Glu Ser Lys Gly Arg Val Leu Leu
1               5                   10                  15
```

```
Val Asp Gly His His Leu Ala Tyr Arg Thr Phe Phe Ala Leu Lys Gly
            20                  25                  30

Leu Thr Thr Ser Arg Gly Glu Pro Val Gln Ala Val Tyr Gly Phe Ala
        35                  40                  45

Lys Ser Leu Leu Lys Ala Leu Lys Glu Asp Gly Tyr Lys Ser Val Phe
50                  55                  60

Val Val Phe Asp Ala Lys Ala Pro Ser Phe Arg His Glu Ala Tyr Glu
65                  70                  75                  80

Ala Tyr Lys Ala Gly Arg Ala Pro Thr Pro Glu Asp Phe Pro Arg Gln
                85                  90                  95

Leu Ala Leu Ile Lys Glu Leu Val Asp Leu Leu Gly Phe Thr Arg Leu
            100                 105                 110

Glu Val Pro Gly Tyr Glu Ala Asp Asp Val Leu Ala Thr Leu Ala Lys
        115                 120                 125

Lys Ala Glu Lys Glu Gly Tyr Glu Val Arg Ile Leu Thr Ala Asp Arg
130                 135                 140

Asp Leu Tyr Gln Leu Val Ser Asp Arg Val Ala Val Leu His Pro Glu
145                 150                 155                 160

Gly His Leu Ile Thr Pro Glu Trp Leu Trp Glu Lys Tyr Gly Leu Arg
                165                 170                 175

Pro Glu Gln Trp Val Asp Phe Arg Ala Leu Val Gly Asp Pro Ser Asp
            180                 185                 190

Asn Leu Pro Gly Val Lys Gly Ile Gly Glu Lys Thr Ala Leu Lys Leu
        195                 200                 205

Leu Lys Glu Trp Gly Ser Leu Glu Ser Leu Leu Lys Asn Leu Asp Arg
210                 215                 220

Val Lys Pro Glu Asn Val Arg Glu Lys Ile Lys Ala His Leu Glu Asp
225                 230                 235                 240

Leu Arg Leu Ser Leu Glu Leu Ser Arg Val Arg Ala Asp Leu Pro Leu
                245                 250                 255

Glu Val Asp Leu Ala Gln Gly Arg Glu Pro Asp Arg Glu Gly Leu Arg
            260                 265                 270

Ala Phe Leu Glu Arg Leu Glu Phe Gly Ser Leu Leu His Glu Phe Gly
        275                 280                 285

Leu Leu Glu Ala Pro Thr Pro Leu Glu Glu Ala Pro Trp Pro Pro Pro
290                 295                 300

Glu Gly Ala Phe Val Gly Phe Val Leu Ser Arg Pro Glu Pro Met Trp
305                 310                 315                 320

Ala Glu Leu Lys Ala Leu Ala Ala Cys Arg Asp Gly Arg Val His Arg
                325                 330                 335

Ala Glu Asp Pro Leu Ala Gly Leu Gly Asp Leu Glu Glu Val Arg Gly
            340                 345                 350

Leu Leu Ala Lys Asp Leu Ala Val Leu Ala Leu Arg Glu Gly Leu Asp
        355                 360                 365

Leu Ala Pro Gly Asp Asp Pro Met Leu Leu Ala Tyr Leu Leu Asp Pro
370                 375                 380

Ser Asn Thr Thr Pro Glu Gly Val Ala Arg Arg Tyr Gly Gly Glu Trp
385                 390                 395                 400

Thr Glu Asp Ala Ala His Arg Ala Leu Leu Ser Glu Arg Leu His Arg
                405                 410                 415

Asn Leu Leu Lys Arg Leu Glu Gly Glu Glu Lys Leu Leu Trp Leu Tyr
            420                 425                 430
```

```
His Asp Val Glu Lys Pro Leu Ser Arg Val Leu Ala His Met Glu Ala
            435                 440                 445

Thr Gly Val Arg Leu Asp Val Ala Tyr Leu Gln Ala Leu Ser Leu Glu
    450                 455                 460

Leu Ala Glu Glu Ile Arg Arg Leu Glu Glu Val Phe Arg Leu Ala
465                 470                 475                 480

Gly His Pro Phe Asn Leu Asn Ser Arg Asp Gln Leu Glu Arg Val Leu
                485                 490                 495

Phe Asp Glu Arg Leu Arg Pro Ala Leu Gly Lys Thr Gln Lys Thr Gly
            500                 505                 510

Lys Arg Ser Thr Ser Ala Ala Val Leu Glu Ala Leu Arg Glu Ala His
        515                 520                 525

Pro Ile Val Glu Lys Ile Leu Gln His Arg Glu Leu Thr Lys Leu Lys
    530                 535                 540

Asn Thr Tyr Val Asp Pro Leu Pro Ser Arg Val His Pro Arg Thr Gly
545                 550                 555                 560

Arg Leu His Thr Arg Phe Asn Gln Thr Ala Thr Ala Thr Gly Arg Leu
                565                 570                 575

Ser Ser Ser Thr Pro Asn Leu Gln Asn Ile Pro Val Arg Thr Pro Leu
            580                 585                 590

Gly Gln Arg Ile Arg Arg Ala Phe Val Ala Glu Ala Gly Trp Ala Leu
        595                 600                 605

Val Ala Ala Leu Asp Tyr Ser Gln Ile Glu Leu Arg Val Leu Ala His
    610                 615                 620

Leu Ser Gly Asp Glu Asn Leu Ile Arg Val Phe Gln Glu Gly Lys Asp
625                 630                 635                 640

Ile His Thr Gln Thr Ala Ser Trp Met Phe Gly Val Pro Pro Glu Ala
                645                 650                 655

Val Asp Pro Leu Met Arg Arg Ala Ala Lys Thr Val Asn Phe Gly Val
            660                 665                 670

Leu Tyr Gly Met Ser Ala His Arg Leu Ser Gln Glu Leu Ala Ile Pro
        675                 680                 685

Tyr Glu Glu Ala Val Ala Phe Ile Glu Arg Tyr Phe Gln Ser Phe Pro
    690                 695                 700

Lys Val Arg Ala Trp Ile Glu Lys Thr Leu Glu Glu Gly Arg Lys Arg
705                 710                 715                 720

Gly Tyr Val Glu Thr Leu Phe Gly Arg Arg Arg Tyr Val Pro Asp Leu
                725                 730                 735

Asn Ala Arg Val Lys Ser Val Arg Glu Ala Ala Glu Arg Met Ala Phe
            740                 745                 750

Asn Met Pro Val Gln Gly Thr Ala Ala Asp Leu Met Lys Leu Ala Met
        755                 760                 765

Val Lys Leu Phe Pro Arg Leu Arg Glu Met Gly Ala Arg Met Leu Leu
    770                 775                 780

Gln Val His Asp Glu Leu Leu Leu Glu Ala Pro Gln Ala Arg Ala Glu
785                 790                 795                 800

Glu Val Ala Ala Leu Ala Lys Glu Ala Met Glu Lys Ala Tyr Pro Leu
                805                 810                 815

Ala Val Pro Leu Glu Val Glu Val Gly Ile Gly Glu Asp Trp Leu Ser
            820                 825                 830

Ala Lys Gly
        835
```

```
<210> SEQ ID NO 4
<211> LENGTH: 832
<212> TYPE: PRT
<213> ORGANISM: Thermus aquaticus

<400> SEQUENCE: 4

Met Arg Gly Met Leu Pro Leu Phe Glu Pro Lys Gly Arg Val Leu Leu
1               5                   10                  15

Val Asp Gly His His Leu Ala Tyr Arg Thr Phe His Ala Leu Lys Gly
            20                  25                  30

Leu Thr Thr Ser Arg Gly Glu Pro Val Gln Ala Val Tyr Gly Phe Ala
        35                  40                  45

Lys Ser Leu Leu Lys Ala Leu Lys Glu Asp Gly Asp Ala Val Ile Val
    50                  55                  60

Val Phe Asp Ala Lys Ala Pro Ser Phe Arg His Glu Ala Tyr Gly Gly
65                  70                  75                  80

Tyr Lys Ala Gly Arg Ala Pro Thr Pro Glu Asp Phe Pro Arg Gln Leu
                85                  90                  95

Ala Leu Ile Lys Glu Leu Val Asp Leu Leu Gly Leu Ala Arg Leu Glu
            100                 105                 110

Val Pro Gly Tyr Glu Ala Asp Asp Val Leu Ala Ser Leu Ala Lys Lys
        115                 120                 125

Ala Glu Lys Glu Gly Tyr Glu Val Arg Ile Leu Thr Ala Asp Lys Asp
    130                 135                 140

Leu Tyr Gln Leu Leu Ser Asp Arg Ile His Val Leu His Pro Glu Gly
145                 150                 155                 160

Tyr Leu Ile Thr Pro Ala Trp Leu Trp Glu Lys Tyr Gly Leu Arg Pro
                165                 170                 175

Asp Gln Trp Ala Asp Tyr Arg Ala Leu Thr Gly Asp Glu Ser Asp Asn
            180                 185                 190

Leu Pro Gly Val Lys Gly Ile Gly Glu Lys Thr Ala Arg Lys Leu Leu
        195                 200                 205

Glu Glu Trp Gly Ser Leu Glu Ala Leu Leu Lys Asn Leu Asp Arg Leu
    210                 215                 220

Lys Pro Ala Ile Arg Glu Lys Ile Leu Ala His Met Asp Asp Leu Lys
225                 230                 235                 240

Leu Ser Trp Asp Leu Ala Lys Val Arg Thr Asp Leu Pro Leu Glu Val
                245                 250                 255

Asp Phe Ala Lys Arg Arg Glu Pro Asp Arg Glu Arg Leu Arg Ala Phe
            260                 265                 270

Leu Glu Arg Leu Glu Phe Gly Ser Leu Leu His Glu Phe Gly Leu Leu
        275                 280                 285

Glu Ser Pro Lys Ala Leu Glu Glu Ala Pro Trp Pro Pro Pro Glu Gly
    290                 295                 300

Ala Phe Val Gly Phe Val Leu Ser Arg Lys Glu Pro Met Trp Ala Asp
305                 310                 315                 320

Leu Leu Ala Leu Ala Ala Ala Arg Gly Gly Arg Val His Arg Ala Pro
                325                 330                 335

Glu Pro Tyr Lys Ala Leu Arg Asp Leu Lys Glu Ala Arg Gly Leu Leu
            340                 345                 350

Ala Lys Asp Leu Ser Val Leu Ala Leu Arg Glu Gly Leu Gly Leu Pro
        355                 360                 365

Pro Gly Asp Asp Pro Met Leu Leu Ala Tyr Leu Leu Asp Pro Ser Asn
    370                 375                 380
```

-continued

Thr Thr Pro Glu Gly Val Ala Arg Arg Tyr Gly Glu Trp Thr Glu
385                 390                 395                 400

Glu Ala Gly Glu Arg Ala Ala Leu Ser Glu Arg Leu Phe Ala Asn Leu
            405                 410                 415

Trp Gly Arg Leu Glu Gly Glu Arg Leu Leu Trp Leu Tyr Arg Glu
        420                 425                 430

Val Glu Arg Pro Leu Ser Ala Val Leu Ala His Met Glu Ala Thr Gly
        435                 440                 445

Val Arg Leu Asp Val Ala Tyr Leu Arg Ala Leu Ser Leu Glu Val Ala
    450                 455                 460

Glu Glu Ile Ala Arg Leu Glu Ala Glu Val Phe Arg Leu Ala Gly His
465                 470                 475                 480

Pro Phe Asn Leu Asn Ser Arg Asp Gln Leu Glu Arg Val Leu Phe Asp
                485                 490                 495

Glu Leu Gly Leu Pro Ala Ile Gly Lys Thr Glu Lys Thr Gly Lys Arg
            500                 505                 510

Ser Thr Ser Ala Ala Val Leu Glu Ala Leu Arg Glu Ala His Pro Ile
        515                 520                 525

Val Glu Lys Ile Leu Gln Tyr Arg Glu Leu Thr Lys Leu Lys Ser Thr
530                 535                 540

Tyr Ile Asp Pro Leu Pro Asp Leu Ile His Pro Arg Thr Gly Arg Leu
545                 550                 555                 560

His Thr Arg Phe Asn Gln Thr Ala Thr Ala Thr Gly Arg Leu Ser Ser
                565                 570                 575

Ser Asp Pro Asn Leu Gln Asn Ile Pro Val Arg Thr Pro Leu Gly Gln
            580                 585                 590

Arg Ile Arg Arg Ala Phe Ile Ala Glu Glu Gly Trp Leu Leu Val Ala
    595                 600                 605

Leu Asp Tyr Ser Gln Ile Glu Leu Arg Val Leu Ala His Leu Ser Gly
    610                 615                 620

Asp Glu Asn Leu Ile Arg Val Phe Gln Glu Gly Arg Asp Ile His Thr
625                 630                 635                 640

Glu Thr Ala Ser Trp Met Phe Gly Val Pro Arg Glu Ala Val Asp Pro
                645                 650                 655

Leu Met Arg Arg Ala Ala Lys Thr Ile Asn Phe Gly Val Leu Tyr Gly
            660                 665                 670

Met Ser Ala His Arg Leu Ser Gln Glu Leu Ala Ile Pro Tyr Glu Glu
        675                 680                 685

Ala Gln Ala Phe Ile Glu Arg Tyr Phe Gln Ser Phe Pro Lys Val Arg
        690                 695                 700

Ala Trp Ile Glu Lys Thr Leu Glu Glu Gly Arg Arg Arg Gly Tyr Val
705                 710                 715                 720

Glu Thr Leu Phe Gly Arg Arg Arg Tyr Val Pro Asp Leu Glu Ala Arg
                725                 730                 735

Val Lys Ser Val Arg Glu Ala Ala Glu Arg Met Ala Phe Asn Met Pro
            740                 745                 750

Val Gln Gly Thr Ala Ala Asp Leu Met Lys Leu Ala Met Val Lys Leu
        755                 760                 765

Phe Pro Arg Leu Glu Glu Met Gly Ala Arg Met Leu Leu Gln Val His
        770                 775                 780

Asp Glu Leu Val Leu Glu Ala Pro Lys Glu Arg Ala Glu Ala Val Ala
785                 790                 795                 800

Arg Leu Ala Lys Glu Val Met Glu Gly Val Tyr Pro Leu Ala Val Pro

```
                    805                 810                 815
Leu Glu Val Glu Val Gly Ile Gly Glu Asp Trp Leu Ser Ala Lys Glu
            820                 825                 830

<210> SEQ ID NO 5
<211> LENGTH: 835
<212> TYPE: PRT
<213> ORGANISM: Thermus scotoductus

<400> SEQUENCE: 5

Met Arg Ala Met Leu Pro Leu Phe Glu Pro Lys Gly Arg Val Leu Leu
1               5                   10                  15

Val Asp Gly His His Leu Ala Tyr Arg Thr Phe Phe Ala Leu Lys Gly
            20                  25                  30

Leu Thr Thr Ser Arg Gly Glu Pro Val Gln Ala Val Tyr Gly Phe Ala
        35                  40                  45

Lys Ser Leu Leu Lys Ala Leu Arg Glu Asp Gly Asp Val Val Ile Val
    50                  55                  60

Val Phe Asp Ala Lys Ala Pro Ser Phe Arg His Gln Thr Tyr Glu Ala
65                  70                  75                  80

Tyr Lys Ala Gly Arg Ala Pro Thr Pro Glu Asp Phe Pro Arg Gln Leu
                85                  90                  95

Ala Leu Ile Lys Glu Met Val Asp Leu Leu Gly Leu Glu Arg Leu Glu
            100                 105                 110

Val Pro Gly Phe Glu Ala Asp Asp Val Leu Ala Thr Leu Ala Lys Lys
        115                 120                 125

Ala Glu Lys Glu Gly Tyr Glu Val Arg Ile Leu Thr Ala Asp Arg Asp
    130                 135                 140

Leu Tyr Gln Leu Leu Ser Glu Arg Ile Ser Ile Leu His Pro Glu Gly
145                 150                 155                 160

Tyr Leu Ile Thr Pro Glu Trp Leu Trp Glu Lys Tyr Gly Leu Lys Pro
                165                 170                 175

Ser Gln Trp Val Asp Tyr Arg Ala Leu Ala Gly Asp Pro Ser Asp Asn
            180                 185                 190

Ile Pro Gly Val Lys Gly Ile Gly Glu Lys Thr Ala Ala Lys Leu Ile
        195                 200                 205

Arg Glu Trp Gly Ser Leu Glu Asn Leu Leu Lys His Leu Glu Gln Val
    210                 215                 220

Lys Pro Ala Ser Val Arg Glu Lys Ile Leu Ser His Met Glu Asp Leu
225                 230                 235                 240

Lys Leu Ser Leu Glu Leu Ser Arg Val Arg Thr Asp Leu Pro Leu Gln
                245                 250                 255

Val Asp Phe Ala Arg Arg Glu Pro Asp Arg Glu Gly Leu Lys Ala
            260                 265                 270

Phe Leu Glu Arg Leu Glu Phe Gly Ser Leu Leu His Glu Phe Gly Leu
        275                 280                 285

Leu Glu Ser Pro Val Ala Ala Glu Glu Ala Pro Trp Pro Pro Pro Glu
    290                 295                 300

Gly Ala Phe Val Gly Tyr Val Leu Ser Arg Pro Glu Pro Met Trp Ala
305                 310                 315                 320

Glu Leu Asn Ala Leu Ala Ala Ala Trp Glu Gly Arg Val Tyr Arg Ala
                325                 330                 335

Glu Asp Pro Leu Glu Ala Leu Arg Gly Leu Gly Glu Val Arg Gly Leu
            340                 345                 350
```

```
Leu Ala Lys Asp Leu Ala Val Leu Ala Leu Arg Glu Gly Ile Ala Leu
            355                 360                 365
Ala Pro Gly Asp Pro Met Leu Leu Ala Tyr Leu Leu Asp Pro Ser
    370                 375                 380
Asn Thr Thr Ala Pro Glu Gly Val Ala Arg Arg Tyr Gly Gly Glu Trp
385                 390                 395                 400
Thr Glu Glu Ala Gly Glu Arg Ala Leu Leu Ser Glu Arg Leu Tyr Ala
                405                 410                 415
Ala Leu Leu Val Arg Leu Lys Gly Glu Arg Leu Leu Trp Leu Tyr
            420                 425                 430
Glu Glu Val Glu Lys Pro Leu Ser Arg Val Leu Ala His Met Glu Ala
                435                 440                 445
Thr Gly Val Arg Leu Asp Val Ala Tyr Leu Lys Ala Leu Ser Leu Glu
    450                 455                 460
Val Glu Ala Glu Leu Arg Arg Leu Glu Glu Val His Arg Leu Ala
465                 470                 475                 480
Gly His Pro Phe Asn Leu Asn Ser Arg Asp Gln Leu Glu Arg Val Leu
                485                 490                 495
Phe Asp Glu Leu Gly Leu Pro Ala Ile Gly Lys Thr Glu Lys Thr Gly
            500                 505                 510
Lys Arg Ser Thr Ser Ala Ala Val Leu Glu Ala Leu Arg Glu Ala His
    515                 520                 525
Pro Ile Val Asp Arg Ile Leu Gln Tyr Arg Glu Leu Ser Lys Leu Lys
    530                 535                 540
Gly Thr Tyr Ile Asp Pro Leu Pro Ala Leu Val His Pro Lys Thr Asn
545                 550                 555                 560
Arg Leu His Thr Arg Phe Asn Gln Thr Ala Thr Ala Thr Gly Arg Leu
                565                 570                 575
Ser Ser Ser Asp Pro Asn Leu Gln Asn Ile Pro Val Arg Thr Pro Leu
            580                 585                 590
Gly Gln Arg Ile Arg Arg Ala Phe Val Ala Glu Glu Gly Trp Arg Leu
    595                 600                 605
Val Val Leu Asp Tyr Ser Gln Ile Glu Leu Arg Val Leu Ala His Leu
    610                 615                 620
Ser Gly Asp Glu Asn Leu Ile Arg Val Phe Gln Glu Gly Gln Asp
625                 630                 635                 640
Ile His Thr Gln Thr Ala Ser Trp Met Phe Gly Val Pro Pro Glu Ala
                645                 650                 655
Val Asp Ser Leu Met Arg Arg Ala Ala Lys Thr Ile Asn Phe Gly Val
            660                 665                 670
Leu Tyr Gly Met Ser Ala His Arg Leu Ser Gly Glu Leu Ala Ile Pro
    675                 680                 685
Tyr Glu Glu Ala Val Ala Phe Ile Glu Arg Tyr Phe Gln Ser Tyr Pro
    690                 695                 700
Lys Val Arg Ala Trp Ile Glu Lys Thr Leu Ala Glu Gly Arg Glu Arg
705                 710                 715                 720
Gly Tyr Val Glu Thr Leu Phe Gly Arg Arg Tyr Val Pro Asp Leu
                725                 730                 735
Ala Ser Arg Val Lys Ser Ile Arg Glu Ala Ala Glu Arg Met Ala Phe
            740                 745                 750
Asn Met Pro Val Gln Gly Thr Ala Ala Asp Leu Met Lys Leu Ala Asn
    755                 760                 765
Val Lys Leu Phe Pro Arg Leu Gln Glu Leu Gly Ala Arg Met Leu Leu
```

```
                    770              775              780
Gln Val His Asp Glu Leu Val Leu Glu Ala Pro Lys Glu Gln Ala Glu
785                 790              795                  800

Glu Val Ala Gln Glu Ala Lys Arg Thr Met Glu Glu Val Trp Pro Leu
                    805              810                  815

Lys Val Pro Leu Glu Val Glu Val Gly Ile Gly Glu Asp Trp Leu Ser
                820              825                  830

Ala Lys Ala
        835

<210> SEQ ID NO 6
<211> LENGTH: 829
<212> TYPE: PRT
<213> ORGANISM: Thermus flavus

<400> SEQUENCE: 6

Met Ala Met Leu Pro Leu Phe Glu Pro Lys Gly Arg Val Leu Leu Val
1               5                   10                  15

Asp Gly His His Leu Ala Tyr Arg Thr Phe Phe Ala Leu Lys Gly Leu
                20                  25                  30

Thr Thr Ser Arg Gly Glu Pro Val Gln Ala Val Tyr Gly Phe Ala Lys
        35                  40                  45

Ser Leu Leu Lys Ala Leu Lys Glu Asp Gly Asp Val Val Val Val Val
50                  55                  60

Phe Asp Ala Lys Ala Pro Ser Phe Arg His Glu Ala Tyr Glu Ala Tyr
65                  70                  75                  80

Lys Ala Gly Arg Ala Pro Thr Pro Glu Asp Phe Pro Arg Gln Leu Ala
                85                  90                  95

Leu Ile Lys Glu Leu Val Asp Leu Leu Gly Leu Val Arg Leu Glu Val
            100                 105                 110

Pro Gly Phe Glu Ala Asp Asp Val Leu Ala Thr Leu Ala Lys Arg Ala
        115                 120                 125

Glu Lys Glu Gly Tyr Glu Val Arg Ile Leu Thr Ala Asp Arg Asp Leu
130                 135                 140

Tyr Gln Leu Leu Ser Glu Arg Ile Ala Ile Leu His Pro Glu Gly Tyr
145                 150                 155                 160

Leu Ile Thr Pro Ala Trp Leu Tyr Glu Lys Tyr Gly Leu Arg Pro Glu
                165                 170                 175

Gln Trp Val Asp Tyr Arg Ala Leu Ala Gly Asp Pro Ser Asp Asn Ile
            180                 185                 190

Pro Gly Val Lys Gly Ile Gly Glu Lys Thr Ala Gln Arg Leu Ile Arg
        195                 200                 205

Glu Trp Gly Ser Leu Glu Asn Leu Phe Gln His Leu Asp Gln Val Lys
210                 215                 220

Pro Ser Leu Arg Glu Lys Leu Gln Ala Gly Met Glu Ala Leu Ala Leu
225                 230                 235                 240

Ser Arg Lys Leu Ser Lys Val His Thr Asp Leu Pro Leu Glu Val Asp
                245                 250                 255

Phe Gly Arg Arg Arg Thr Pro Asn Leu Glu Gly Leu Arg Ala Phe Leu
            260                 265                 270

Glu Arg Leu Glu Phe Gly Ser Leu Leu His Glu Phe Gly Leu Leu Glu
        275                 280                 285

Gly Pro Lys Ala Ala Glu Glu Ala Pro Trp Pro Glu Gly Ala Phe
290                 295                 300
```

```
Leu Gly Phe Ser Phe Ser Arg Pro Glu Pro Met Trp Ala Glu Leu Leu
305                 310                 315                 320

Ala Leu Ala Gly Ala Trp Glu Gly Arg Leu Phe Arg Ala Gln Asp Pro
            325                 330                 335

Leu Arg Gly Leu Arg Asp Leu Lys Gly Val Arg Gly Ile Leu Ala Lys
        340                 345                 350

Asp Leu Ala Val Leu Ala Leu Arg Glu Gly Leu Asp Leu Phe Pro Glu
    355                 360                 365

Asp Asp Pro Met Leu Leu Ala Tyr Leu Leu Asp Pro Ser Asn Thr Thr
370                 375                 380

Pro Glu Gly Val Ala Arg Arg Tyr Gly Gly Glu Trp Thr Glu Asp Ala
385                 390                 395                 400

Gly Glu Arg Ala Leu Leu Ala Glu Arg Leu Phe Gln Thr Leu Lys Glu
                405                 410                 415

Arg Leu Tyr Gly Glu Glu Arg Leu Leu Trp Leu Tyr Glu Glu Val Glu
            420                 425                 430

Lys Pro Leu Ser Arg Val Leu Ala Arg Met Glu Ala Thr Gly Val Arg
        435                 440                 445

Leu Asp Val Ala Tyr Leu Gln Ala Leu Ser Leu Glu Val Glu Ala Glu
    450                 455                 460

Val Arg Gln Leu Glu Glu Val Phe Arg Leu Ala Gly His Pro Phe
465                 470                 475                 480

Asn Leu Asn Ser Arg Asp Gln Leu Glu Arg Val Leu Phe Asp Glu Leu
                485                 490                 495

Gly Leu Pro Ala Ile Gly Lys Thr Glu Lys Thr Gly Lys Arg Ser Thr
            500                 505                 510

Ser Ala Ala Val Leu Glu Ala Leu Arg Glu Ala His Pro Ile Val Asp
        515                 520                 525

Arg Ile Leu Gln Tyr Arg Glu Leu Thr Lys Leu Lys Asn Thr Tyr Ile
    530                 535                 540

Asp Pro Leu Pro Ala Leu Val His Pro Lys Thr Gly Arg Leu His Arg
545                 550                 555                 560

Arg Phe Asn Gln Thr Ala Thr Thr Gly Arg Leu Ser Ser Ser Asp Pro
                565                 570                 575

Asn Leu Gln Asn Ile Pro Val Arg Thr Val Leu Gly Gln Arg Ile Arg
            580                 585                 590

Arg Ala Phe Val Ala Glu Glu Gly Trp Val Leu Val Val Leu Asp Tyr
        595                 600                 605

Ser Gln Ile Glu Arg Leu Val Leu Ala His Leu Ser Gly Thr Glu Asn
    610                 615                 620

Leu Ile Arg Val Phe Gln Glu Gly Arg Glu Ile His Thr Gln Thr Ala
625                 630                 635                 640

Ser Trp Met Phe Gly Val Ser Pro Glu Gly Val Asp Pro Leu Met Arg
                645                 650                 655

Arg Ala Ala Lys Thr Ile Asn Phe Gly Val Leu Tyr Gly Met Ser Ala
            660                 665                 670

His Arg Leu Ser Gly Glu Leu Ser Ile Pro Tyr Glu Glu Ala Val Ala
        675                 680                 685

Phe Ile Glu Arg Tyr Phe Gln Ser Tyr Pro Lys Val Arg Ala Trp Ile
    690                 695                 700

Glu Gly Thr Leu Glu Glu Gly Arg Arg Gly Tyr Val Glu Thr Leu
705                 710                 715                 720

Phe Gly Arg Arg Arg Tyr Val Pro Asp Leu Asn Ala Arg Val Lys Ser
```

```
                    725                 730                 735
Val Arg Glu Ala Ala Glu Arg Met Ala Phe Asn Asn Pro Val Gln Gly
            740                 745                 750

Thr Ala Ala Asp Leu Met Lys Leu Ala Met Val Arg Leu Phe Pro Arg
            755                 760                 765

Leu Gln Glu Leu Gly Ala Arg Met Leu Leu Gln Val His Asp Glu Leu
    770                 775                 780

Val Leu Glu Ala Pro Lys Asp Arg Ala Glu Arg Val Ala Ala Leu Ala
785                 790                 795                 800

Lys Glu Val Met Glu Gly Val Trp Pro Leu Gln Val Pro Leu Glu Val
                805                 810                 815

Glu Val Gly Leu Gly Glu Asp Trp Leu Ser Ala Lys Glu
            820                 825

<210> SEQ ID NO 7
<211> LENGTH: 830
<212> TYPE: PRT
<213> ORGANISM: Thermus oshimai

<400> SEQUENCE: 7

Met Leu Pro Leu Phe Glu Pro Lys Gly Arg Val Leu Leu Val Asp Gly
1               5                   10                  15

His His Leu Ala Tyr Arg Thr Phe Phe Ala Leu Lys Gly Leu Thr Thr
            20                  25                  30

Ser Arg Gly Glu Pro Val Gln Ala Val Tyr Asp Phe Ala Lys Ser Leu
        35                  40                  45

Leu Lys Ala Leu Lys Glu Asp Gly Glu Val Ala Ile Val Val Phe Asp
    50                  55                  60

Ala Lys Ala Pro Ser Phe Arg His Glu Glu Ala Tyr Glu Ala Tyr Lys
65                  70                  75                  80

Ala Gly Arg Ala Pro Thr Pro Glu Asp Phe Pro Arg Gln Leu Ala Leu
                85                  90                  95

Ile Lys Glu Leu Val Asp Leu Leu Gly Leu Asp Arg Leu Glu Val Pro
            100                 105                 110

Gly Phe Glu Ala Asp Asp Val Leu Ala Thr Leu Ala Lys Lys Ala Glu
        115                 120                 125

Arg Glu Gly Tyr Glu Val Arg Ile Leu Ser Ala Asp Arg Asp Leu Tyr
    130                 135                 140

Gln Leu Leu Ser Asp Arg Ile His Leu Leu His Pro Glu Gly Glu Val
145                 150                 155                 160

Leu Thr Pro Gly Trp Leu Gln Glu Arg Tyr Gly Leu Ser Pro Glu Arg
                165                 170                 175

Trp Val Glu Tyr Arg Ala Leu Val Gly Asp Pro Ser Asp Asn Leu Pro
            180                 185                 190

Gly Val Pro Gly Ile Gly Glu Lys Thr Ala Leu Lys Leu Leu Lys Glu
        195                 200                 205

Trp Gly Ser Leu Glu Ala Ile Leu Lys Asn Leu Asp Gln Val Lys Pro
    210                 215                 220

Glu Arg Val Arg Glu Ala Ile Arg Asn Asn Leu Asp Lys Leu Gln Met
225                 230                 235                 240

Ser Leu Glu Leu Ser Arg Leu Arg Thr Asp Leu Pro Leu Glu Val Asp
                245                 250                 255

Phe Ala Lys Arg Arg Glu Pro Asp Trp Glu Gly Leu Lys Ala Phe Leu
            260                 265                 270
```

```
Glu Arg Leu Glu Phe Gly Ser Leu Leu His Gly Leu Leu Glu
            275                 280                 285

Ala Pro Lys Glu Ala Glu Ala Pro Trp Pro Pro Gly Gly Ala
        290                 295                 300

Phe Leu Gly Phe Leu Leu Ser Arg Pro Glu Pro Asn Trp Ala Glu Leu
305                 310                 315                 320

Leu Ala Leu Ala Gly Ala Lys Glu Gly Arg Phe His Arg Ala Glu Asp
                325                 330                 335

Pro Val Gly Ala Leu Lys Asp Leu Lys Glu Ile Arg Gly Leu Leu Ala
                340                 345                 350

Lys Asp Leu Ser Val Leu Ala Leu Arg Glu Gly Arg Glu Ile Pro Pro
            355                 360                 365

Gly Asp Asp Pro Met Leu Leu Ala Tyr Leu Leu Asp Pro Gly Asn Thr
        370                 375                 380

Asn Pro Glu Gly Val Ala Arg Arg Tyr Gly Gly Glu Trp Lys Glu Asp
385                 390                 395                 400

Ala Ala Ala Arg Ala Leu Leu Ser Glu Arg Leu Trp Gln Ala Leu Tyr
                405                 410                 415

Pro Arg Val Glu Glu Glu Arg Leu Leu Trp Leu Tyr Arg Glu Val Glu
            420                 425                 430

Arg Pro Leu Ala Gln Val Leu Ala His Met Glu Ala Thr Gly Val Arg
        435                 440                 445

Leu Asp Val Pro Tyr Leu Glu Ala Leu Ser Gln Glu Val Ala Phe Glu
        450                 455                 460

Leu Glu Arg Leu Glu Ala Glu Val His Arg Leu Ala Gly His Pro Phe
465                 470                 475                 480

Asn Leu Asn Ser Arg Asp Gln Leu Glu Arg Val Leu Phe Asp Glu Leu
                485                 490                 495

Gly Leu Pro Pro Ile Gly Lys Thr Glu Lys Thr Gly Lys Arg Ser Thr
            500                 505                 510

Ser Ala Ala Val Leu Glu Leu Leu Arg Glu Ala His Pro Ile Val Gly
        515                 520                 525

Arg Ile Leu Glu Tyr Arg Glu Leu Met Lys Leu Lys Ser Thr Tyr Ile
530                 535                 540

Val Pro Leu Pro Arg Leu Val His Pro Lys Thr Gly Arg Leu His Thr
545                 550                 555                 560

Arg Phe Asn Gln Thr Ala Thr Ala Thr Gly Arg Leu Ser Ser Ser Thr
                565                 570                 575

Pro Asn Leu Gln Asn Ile Pro Val Arg Thr Pro Leu Gly Gln Arg Ile
            580                 585                 590

Arg Lys Ala Phe Ile Ala Glu Glu Gly His Leu Leu Val Ala Leu Val
        595                 600                 605

Tyr Ser Gln Ile Glu Leu Arg Val Leu Ala His Leu Ser Gly Asp Glu
        610                 615                 620

Asn Leu Ile Arg Val Phe Arg Glu Gly Lys Asp Ile His Thr Glu Thr
625                 630                 635                 640

Ala Ala Trp Met Phe Gly Val Pro Pro Glu Gly Val Asp Gly Ala Met
                645                 650                 655

Arg Arg Ala Ala Lys Thr Val Asn Tyr Gly Val Leu Tyr Gly Met Ser
            660                 665                 670

Ala His Arg Leu Ser Gln Val Leu Ser Ile Pro Tyr Glu Glu Ala Ala
        675                 680                 685

Ala Phe Ile Glu Arg Tyr Phe Gln Ser Phe Pro Lys Val Arg Ala Trp
```

```
            690                 695                 700
Ile Ala Lys Thr Leu Glu Glu Gly Arg Lys Gly Tyr Val Glu Thr
705                 710                 715                 720

Leu Phe Gly Arg Arg Arg Tyr Val Pro Asp Leu Asn Ala Arg Val Lys
                725                 730                 735

Ser Val Arg Glu Ala Ala Glu Arg Met Ala Phe Asn Met Pro Val Gln
            740                 745                 750

Gly Thr Ala Ala Asp Leu Met Lys Leu Ala Met Val Lys Leu Phe Pro
                755                 760                 765

Arg Leu Arg Pro Leu Gly Val Arg Ile Leu Leu Gln Val His Asp Glu
770                 775                 780

Leu Val Leu Glu Ala Pro Lys Ala Arg Ala Glu Glu Ala Ala Gln Leu
785                 790                 795                 800

Ala Lys Glu Thr Met Glu Gly Val Tyr Pro Leu Ser Val Pro Leu Glu
                805                 810                 815

Val Glu Val Gly Met Gly Glu Asp Trp Leu Ser Ala Lys Ala
                820                 825                 830

<210> SEQ ID NO 8
<211> LENGTH: 831
<212> TYPE: PRT
<213> ORGANISM: Thermus filiformis

<400> SEQUENCE: 8

Met Thr Pro Leu Phe Asp Leu Glu Glu Pro Pro Lys Arg Val Leu Leu
1               5                   10                  15

Val Asp Gly His His Leu Ala Tyr Arg Thr Phe Tyr Ala Leu Ser Leu
                20                  25                  30

Thr Thr Ser Arg Gly Glu Pro Val Gln Met Val Tyr Gly Phe Ala Arg
            35                  40                  45

Ser Leu Leu Lys Ala Leu Lys Glu Asp Gly Gln Ala Val Val Val Val
50                  55                  60

Phe Asp Ala Lys Ala Pro Ser Phe Arg His Glu Ala Tyr Glu Ala Tyr
65                  70                  75                  80

Lys Ala Gly Arg Ala Pro Thr Pro Glu Asp Phe Pro Arg Gln Leu Ala
                85                  90                  95

Leu Val Lys Arg Leu Val Asp Leu Leu Gly Leu Val Arg Leu Glu Ala
            100                 105                 110

Pro Gly Tyr Glu Ala Asp Asp Val Leu Gly Thr Leu Ala Lys Lys Ala
        115                 120                 125

Glu Arg Glu Gly Met Glu Val Arg Ile Leu Thr Gly Asp Arg Asp Phe
130                 135                 140

Phe Gln Leu Leu Ser Lys Val Ser Val Leu Leu Pro Asp Gly Thr
145                 150                 155                 160

Leu Val Thr Pro Lys Val Gln Glu Lys Tyr Gly Val Pro Pro Glu Arg
                165                 170                 175

Trp Val Asp Phe Arg Ala Leu Thr Gly Asp Arg Ser Asp Asn Ile Pro
            180                 185                 190

Gly Val Ala Gly Ile Gly Glu Lys Thr Ala Leu Arg Leu Leu Ala Glu
        195                 200                 205

Trp Gly Ser Val Glu Asn Leu Leu Lys Asn Leu Asp Arg Val Lys Pro
210                 215                 220

Asp Ser Val Arg Arg Lys Ile Glu Ala His Leu Glu Asp Leu Arg Leu
225                 230                 235                 240
```

```
Ser Leu Asp Leu Ala Arg Ile Arg Thr Asp Leu Pro Leu Glu Val Asp
                245                 250                 255

Phe Lys Ala Leu Arg Arg Thr Pro Asp Leu Glu Gly Leu Arg Ala
            260                 265                 270

Phe Leu Glu Glu Leu Glu Phe Gly Ser Leu Leu His Glu Phe Gly Leu
            275                 280                 285

Leu Gly Gly Glu Lys Pro Arg Glu Glu Ala Pro Trp Pro Pro Glu
    290                 295                 300

Gly Ala Phe Val Gly Phe Leu Ser Arg Lys Glu Pro Met Trp Ala
305                 310                 315                 320

Glu Leu Leu Ala Leu Ala Ala Ala Glu Gly Arg Val His Arg Ala
                325                 330                 335

Thr Ser Pro Val Glu Ala Leu Ala Asp Leu Lys Glu Ala Arg Gly Phe
            340                 345                 350

Leu Ala Lys Asp Leu Ala Val Leu Ala Leu Arg Glu Gly Val Ala Leu
            355                 360                 365

Asp Pro Thr Asp Pro Leu Leu Val Ala Tyr Leu Leu Asp Pro Ala
    370                 375                 380

Asn Thr Asn Pro Glu Gly Val Ala Arg Arg Tyr Gly Gly Glu Phe Thr
385                 390                 395                 400

Glu Asp Ala Ala Glu Arg Ala Leu Leu Ser Glu Arg Leu Phe Gln Asn
                405                 410                 415

Leu Phe Glu Arg Leu Ser Glu Lys Leu Leu Trp Leu Tyr Gln Glu Val
            420                 425                 430

Glu Arg Pro Leu Ser Arg Val Leu Ala His Met Glu Ala Arg Gly Val
    435                 440                 445

Arg Leu Asp Val Pro Leu Leu Glu Ala Leu Ser Phe Glu Leu Glu Lys
450                 455                 460

Glu Met Glu Arg Leu Glu Gly Glu Val Phe Arg Leu Ala Gly His Pro
465                 470                 475                 480

Phe Asn Leu Asn Ser Arg Asp Gln Leu Glu Arg Val Leu Phe Asp Glu
                485                 490                 495

Leu Gly Leu Thr Pro Val Gly Arg Thr Glu Lys Thr Gly Arg Ser Thr
            500                 505                 510

Ala Gln Gly Ala Leu Glu Ala Leu Arg Gly Ala His Pro Ile Val Glu
            515                 520                 525

Leu Ile Leu Gln Tyr Arg Glu Leu Ser Lys Leu Lys Ser Thr Tyr Leu
    530                 535                 540

Asp Pro Leu Pro Arg Leu Val His Pro Arg Thr Gly Arg Leu His Thr
545                 550                 555                 560

Arg Phe Asn Gln Thr Ala Thr Ala Thr Gly Arg Leu Ser Ser Ser Thr
                565                 570                 575

Pro Asn Leu Gln Asn Ile Pro Val Arg Thr Pro Leu Gly Gln Arg Ile
            580                 585                 590

Arg Lys Ala Phe Val Ala Glu Glu Gly Trp Leu Leu Leu Ala Ala Asp
            595                 600                 605

Tyr Ser Gln Ile Glu Leu Arg Val Leu Ala His Leu Ser Gly Asp Glu
    610                 615                 620

Asn Leu Lys Arg Val Phe Arg Glu Gly Lys Asp Ile His Thr Glu Thr
625                 630                 635                 640

Ala Ala Trp Met Phe Gly Leu Asp Pro Ala Leu Val Asp Pro Lys Met
                645                 650                 655

Arg Arg Ala Ala Lys Thr Val Asn Phe Gly Val Leu Tyr Gly Met Ser
```

```
            660                 665                 670
Ala His Arg Leu Ser Gln Glu Leu Gly Ile Asp Tyr Lys Glu Ala Glu
                675                 680                 685

Ala Phe Ile Glu Arg Tyr Phe Gln Ser Phe Pro Lys Val Arg Ala Trp
            690                 695                 700

Ile Glu Arg Thr Leu Glu Gly Arg Thr Arg Gly Tyr Val Glu Thr
705                 710                 715                 720

Leu Phe Gly Arg Arg Tyr Val Pro Asp Leu Ala Ser Arg Val Arg
                725                 730                 735

Ser Val Arg Glu Ala Ala Glu Arg Met Ala Phe Asn Met Pro Val Gln
            740                 745                 750

Gly Thr Ala Ala Asp Leu Met Lys Ile Ala Met Val Lys Leu Phe Pro
            755                 760                 765

Arg Leu Lys Pro Leu Gly Ala His Leu Leu Gln Val His Asp Glu
                770                 775                 780

Leu Val Leu Glu Val Pro Glu Asp Arg Ala Glu Glu Ala Lys Ala Leu
785                 790                 795                 800

Val Lys Glu Val Met Glu Asn Thr Tyr Pro Leu Asp Val Pro Leu Glu
                805                 810                 815

Val Glu Val Gly Val Gly Arg Asp Trp Leu Glu Ala Lys Gly Asp
                820                 825                 830

<210> SEQ ID NO 9
<211> LENGTH: 889
<212> TYPE: PRT
<213> ORGANISM: Thermotoga maritima MSB8

<400> SEQUENCE: 9

Met Ala Arg Leu Phe Leu Phe Asp Gly Thr Ala Leu Ala Tyr Arg Ala
1               5                   10                  15

Tyr Tyr Ala Leu Asp Arg Ser Leu Ser Thr Ser Thr Gly Ile Pro Thr
                20                  25                  30

Asn Ala Thr Tyr Gly Val Ala Arg Met Leu Val Arg Phe Ile Lys Asp
            35                  40                  45

His Ile Ile Val Gly Lys Asp Tyr Val Ala Val Ala Phe Asp Lys Lys
    50                  55                  60

Ala Ala Thr Phe Arg His Lys Leu Leu Glu Thr Tyr Lys Ala Gln Arg
65                  70                  75                  80

Pro Lys Thr Pro Asp Leu Leu Ile Gln Gln Leu Pro Tyr Ile Lys Lys
                85                  90                  95

Leu Val Glu Ala Leu Gly Met Lys Val Leu Glu Val Glu Gly Tyr Glu
            100                 105                 110

Ala Asp Asp Ile Ile Ala Thr Leu Ala Val Lys Gly Leu Pro Leu Phe
        115                 120                 125

Asp Glu Ile Phe Ile Val Thr Gly Asp Lys Asp Met Leu Gln Leu Val
    130                 135                 140

Asn Glu Lys Ile Lys Val Trp Arg Ile Val Lys Gly Ile Ser Asp Leu
145                 150                 155                 160

Glu Leu Tyr Asp Ala Gln Lys Val Lys Glu Lys Tyr Gly Val Glu Pro
                165                 170                 175

Gln Gln Ile Pro Asp Leu Leu Ala Leu Thr Gly Glu Ile Asp Asn Ile
            180                 185                 190

Pro Gly Val Thr Gly Ile Gly Glu Lys Thr Ala Val Gln Leu Leu Glu
        195                 200                 205
```

-continued

```
Lys Tyr Lys Asp Leu Glu Asp Ile Leu Asn His Val Arg Glu Leu Pro
    210                 215                 220
Gln Lys Val Arg Lys Ala Leu Leu Arg Asp Arg Glu Asn Ala Ile Leu
225                 230                 235                 240
Ser Lys Lys Leu Ala Ile Leu Glu Thr Asn Val Pro Ile Glu Ile Asn
                245                 250                 255
Trp Glu Glu Leu Arg Tyr Gln Gly Tyr Asp Arg Glu Lys Leu Leu Pro
                260                 265                 270
Leu Leu Lys Glu Leu Glu Phe Ala Ser Ile Met Lys Glu Leu Gln Leu
            275                 280                 285
Tyr Glu Glu Ser Glu Pro Val Gly Tyr Arg Ile Val Lys Asp Leu Val
    290                 295                 300
Glu Phe Glu Lys Leu Ile Glu Lys Leu Arg Glu Ser Pro Ser Phe Ala
305                 310                 315                 320
Ile Asp Leu Glu Thr Ser Ser Leu Asp Pro Phe Asp Cys Asp Ile Val
                325                 330                 335
Gly Ile Ser Val Ser Phe Lys Pro Lys Glu Ala Tyr Tyr Ile Pro Leu
                340                 345                 350
His His Arg Asn Ala Gln Asn Leu Asp Glu Lys Glu Val Leu Lys Lys
            355                 360                 365
Leu Lys Glu Ile Leu Glu Asp Pro Gly Ala Lys Ile Val Gly Gln Asn
    370                 375                 380
Leu Lys Phe Asp Tyr Lys Val Leu Met Val Lys Gly Val Glu Pro Val
385                 390                 395                 400
Pro Pro Tyr Phe Asp Thr Met Ile Ala Ala Tyr Leu Leu Glu Pro Asn
                405                 410                 415
Glu Lys Lys Phe Asn Leu Asp Asp Leu Ala Leu Lys Phe Leu Gly Tyr
                420                 425                 430
Lys Met Thr Ser Tyr Gln Glu Leu Met Ser Phe Ser Phe Pro Leu Phe
            435                 440                 445
Gly Phe Ser Phe Ala Asp Val Pro Val Glu Lys Ala Asn Asn Tyr Ser
    450                 455                 460
Cys Glu Asp Ala Asp Ile Thr Tyr Arg Leu Tyr Lys Thr Leu Ser Leu
465                 470                 475                 480
Lys Leu His Glu Ala Asp Leu Glu Asn Val Phe Tyr Lys Ile Glu Asn
                485                 490                 495
Pro Leu Val Asn Val Leu Ala Arg Met Glu Leu Asn Gly Val Tyr Val
                500                 505                 510
Asp Thr Glu Phe Leu Lys Lys Leu Ser Glu Glu Gly Lys Lys Leu Glu
            515                 520                 525
Glu Leu Ala Lys Glu Ile Tyr Arg Ile Ala Gly Glu Pro Phe Asn Ile
    530                 535                 540
Asn Ser Pro Lys Gln Val Ser Arg Ile Leu Phe Glu Lys Leu Gly Ile
545                 550                 555                 560
Lys Pro Arg Gly Lys Thr Thr Lys Thr Gly Asp Tyr Ser Thr Arg Ile
                565                 570                 575
Glu Val Leu Glu Glu Leu Ala Gly Glu His Glu Ile Ile Pro Leu Ile
                580                 585                 590
Leu Glu Tyr Arg Lys Ile Gln Lys Leu Lys Ser Thr Tyr Ile Asp Leu
            595                 600                 605
Pro Lys Met Val Asn Pro Lys Thr Gly Arg Ile His Ala Ser Phe Asn
    610                 615                 620
Gln Thr Gly Thr Ala Thr Gly Arg Leu Ser Ser Ser Asp Pro Asn Leu
```

```
                625                 630                 635                 640
        Gln Asn Leu Pro Thr Lys Ser Glu Glu Gly Lys Glu Ile Arg Lys Ala
                        645                 650                 655

Ile Val Pro Gln Asp Pro Asn Trp Trp Ile Val Ser Ala Asp Tyr Ser
                        660                 665                 670

Gln Ile Glu Leu Arg Ile Leu Ala His Leu Ser Gly Asp Glu Asn Leu
                        675                 680                 685

Leu Arg Ala Phe Glu Glu Gly Ile Asp Val His Thr Leu Thr Ala Ser
                690                 695                 700

Arg Ile Phe Asn Val Lys Pro Glu Glu Val Thr Glu Glu Met Arg Arg
        705                 710                 715                 720

Ala Gly Lys Met Val Asn Phe Ser Ile Ile Tyr Gly Val Thr Pro Tyr
                        725                 730                 735

Gly Leu Ser Val Arg Leu Gly Val Pro Val Lys Glu Ala Glu Lys Met
                        740                 745                 750

Ile Val Asn Tyr Phe Val Leu Tyr Pro Lys Val Arg Asp Tyr Ile Gln
                        755                 760                 765

Arg Val Val Ser Glu Ala Lys Glu Lys Gly Tyr Val Arg Thr Leu Phe
                770                 775                 780

Gly Arg Lys Arg Asp Ile Pro Gln Leu Met Ala Arg Asp Arg Asn Thr
        785                 790                 795                 800

Gln Ala Glu Gly Glu Arg Ile Ala Ile Asn Thr Pro Gln Gly Thr Ala
                        805                 810                 815

Ala Asp Ile Ile Lys Leu Ala Asn Ile Glu Ile Asp Arg Glu Leu Lys
                        820                 825                 830

Glu Arg Lys Met Arg Ser Lys Met Ile Ile Gln Val His Asp Glu Leu
                        835                 840                 845

Val Phe Glu Val Pro Asn Glu Glu Lys Asp Ala Leu Val Glu Leu Val
                850                 855                 860

Lys Asp Arg Met Thr Asn Val Val Lys Leu Ser Val Pro Leu Glu Val
        865                 870                 875                 880

Asp Val Thr Ile Gly Lys Thr Trp Ser
                        885

<210> SEQ ID NO 10
<211> LENGTH: 892
<212> TYPE: PRT
<213> ORGANISM: Thermotoga neapolitana DSM4359

<400> SEQUENCE: 10

Met Ala Arg Leu Phe Leu Phe Asp Gly Thr Ala Leu Ala Tyr Arg Ala
1               5                   10                  15

Tyr Tyr Ala Leu Asp Arg Ser Leu Ser Thr Ser Thr Gly Ile Pro Thr
                20                  25                  30

Asn Ala Val Tyr Gly Val Ala Arg Met Leu Val Lys Phe Ile Lys Glu
                35                  40                  45

His Ile Ile Pro Glu Lys Asp Tyr Ala Ala Val Ala Phe Asp Lys Lys
                50                  55                  60

Ala Ala Thr Phe Arg His Lys Leu Leu Glu Ala Tyr Lys Ala Gln Arg
65                  70                  75                  80

Pro Lys Thr Pro Asp Leu Leu Val Gln Gln Leu Pro Tyr Ile Lys Arg
                85                  90                  95

Leu Ile Glu Ala Leu Gly Phe Lys Val Leu Glu Leu Glu Gly Tyr Glu
                100                 105                 110
```

-continued

Ala Asp Asp Ile Ile Ala Thr Leu Ala Val Lys Gly Cys Thr Phe Phe
        115                 120                 125

Asp Glu Ile Phe Ile Ile Thr Gly Asp Lys Asp Met Leu Gln Leu Val
        130                 135                 140

Asn Glu Lys Ile Lys Val Trp Arg Ile Val Lys Gly Ile Ser Asp Leu
145                 150                 155                 160

Glu Leu Tyr Asp Ser Lys Lys Val Lys Glu Arg Tyr Gly Val Glu Pro
            165                 170                 175

His Gln Ile Pro Asp Leu Leu Ala Leu Thr Gly Asp Glu Ile Asp Asn
        180                 185                 190

Ile Pro Gly Val Thr Gly Ile Gly Glu Lys Thr Ala Val Gln Leu Leu
        195                 200                 205

Gly Lys Tyr Arg Asn Leu Glu Asp Ile Leu Glu His Ala Arg Glu Leu
        210                 215                 220

Pro Gln Arg Val Arg Lys Ala Leu Leu Arg Asp Arg Glu Val Ala Ile
225                 230                 235                 240

Leu Ser Lys Lys Leu Ala Thr Leu Val Thr Asn Ala Pro Val Glu Val
            245                 250                 255

Asp Trp Glu Glu Met Lys Tyr Arg Gly Tyr Asp Lys Arg Lys Leu Leu
        260                 265                 270

Pro Ile Leu Lys Glu Leu Glu Phe Ala Ser Ile Asn Lys Glu Leu Gln
        275                 280                 285

Leu Tyr Glu Glu Ala Glu Pro Thr Gly Tyr Glu Ile Val Lys Asp His
        290                 295                 300

Lys Thr Phe Glu Asp Leu Ile Glu Lys Leu Lys Glu Val Pro Ser Phe
305                 310                 315                 320

Ala Leu Asp Leu Glu Thr Ser Ser Leu Asp Pro Phe Asn Cys Glu Ile
            325                 330                 335

Val Gly Ile Ser Val Ser Phe Lys Pro Lys Thr Ala Tyr Tyr Ile Pro
        340                 345                 350

Leu His His Arg Asn Ala Gln Asn Leu Asp Glu Thr Leu Val Leu Ser
        355                 360                 365

Lys Leu Lys Glu Ile Leu Glu Asp Pro Ser Ser Lys Ile Val Gly Gln
370                 375                 380

Asn Leu Lys Tyr Asp Tyr Lys Val Leu Met Val Lys Gly Ile Ser Pro
385                 390                 395                 400

Val Tyr Pro His Phe Asp Thr Met Ile Ala Ala Tyr Leu Leu Glu Pro
            405                 410                 415

Asn Glu Lys Lys Phe Asn Leu Glu Asp Leu Ser Leu Lys Phe Leu Gly
        420                 425                 430

Tyr Lys Met Thr Ser Tyr Gln Glu Leu Met Ser Phe Ser Ser Pro Leu
        435                 440                 445

Phe Gly Phe Ser Phe Ala Asp Val Pro Val Asp Lys Ala Ala Asn Tyr
    450                 455                 460

Ser Cys Glu Asp Ala Asp Ile Thr Tyr Arg Leu Tyr Lys Ile Leu Ser
465                 470                 475                 480

Met Lys Leu His Glu Ala Glu Leu Glu Asn Val Phe Tyr Arg Ile Glu
            485                 490                 495

Asn Pro Leu Val Asn Val Leu Ala Arg Met Glu Leu Asn Gly Val Tyr
        500                 505                 510

Val Asp Thr Glu Phe Leu Lys Lys Leu Ser Glu Glu Tyr Gly Lys Lys
        515                 520                 525

Leu Glu Glu Leu Ala Glu Lys Ile Tyr Gln Ile Ala Gly Glu Pro Phe

```
                    530              535              540
Asn Ile Asn Ser Pro Lys Gln Val Ser Lys Ile Leu Phe Glu Lys Leu
545                 550              555              560

Gly Ile Lys Pro Arg Gly Lys Thr Thr Lys Thr Gly Glu Tyr Ser Thr
                565              570              575

Arg Ile Glu Val Leu Glu Ile Ala Asn Glu His Glu Ile Val Pro
                580              585              590

Leu Ile Leu Glu Tyr Arg Lys Ile Gln Lys Leu Lys Ser Thr Tyr Ile
                595              600              605

Asp Thr Leu Pro Lys Leu Val Asn Pro Lys Thr Gly Arg Ile His Ala
                610              615              620

Ser Phe His Gln Thr Gly Thr Ala Thr Gly Arg Leu Ser Ser Ser Asp
625                 630              635              640

Pro Asn Leu Gln Asn Leu Pro Thr Lys Ser Val Glu Gly Lys Glu Ile
                645              650              655

Arg Lys Ala Ile Val Pro Gln Asp Pro Asp Trp Trp Ile Val Ser Ala
                660              665              670

Asp Tyr Ser Gln Ile Glu Leu Arg Ile Leu Ala His Leu Ser Gly Asp
                675              680              685

Glu Asn Leu Val Lys Ala Phe Glu Glu Gly Ile Asp Val His Thr Leu
690                 695              700

Thr Ala Ser Arg Ile Tyr Asn Val Lys Pro Glu Glu Val Asn Glu Glu
705                 710              715              720

Met Arg Arg Val Gly Lys Met Val Asn Phe Ser Ile Ile Tyr Gly Val
                725              730              735

Thr Pro Tyr Gly Leu Ser Val Arg Leu Gly Ile Pro Val Lys Glu Ala
                740              745              750

Glu Lys Met Ile Ile Ser Tyr Phe Thr Leu Tyr Pro Lys Val Arg Ser
                755              760              765

Tyr Ile Gln Gln Val Val Ala Glu Ala Lys Lys Gly Tyr Val Arg
770                 775              780

Thr Leu Phe Gly Arg Lys Arg Asp Ile Pro Gln Leu Met Ala Arg Asp
785                 790              795              800

Lys Asn Thr Gln Ser Glu Gly Glu Arg Ile Ala Ile Asn Thr Pro Ile
                805              810              815

Gln Gly Thr Ala Ala Asp Ile Lys Leu Ala Met Ile Asp Ile Asp Glu
                820              825              830

Glu Leu Arg Lys Arg Asn Met Lys Ser Arg Met Ile Ile Gln Val His
                835              840              845

Asp Glu Leu Val Phe Glu Val Pro Asp Glu Glu Lys Glu Glu Leu Val
850                 855              860

Asp Leu Val Lys Asn Lys Asn Thr Asn Val Val Lys Leu Ser Val Pro
865                 870              875              880

Leu Glu Val Asp Ile Ser Ile Gly Lys Ser Trp Ser
                885              890
```

<210> SEQ ID NO 11
<211> LENGTH: 2499
<212> TYPE: DNA
<213> ORGANISM: Thermus aquaticus

<400> SEQUENCE: 11
atgcgtggca tgcttcctct ttttgagccc aagggccggg tcctcctggt ggacggccac    60 caccGtggcct accgcacctt ccacgccctg aagggcctca ccaccagccg gggggagccg    120

```
gtgcaggcgg tctacggctt cgccaagagc ctcctcaagg ccctcaagga ggacggggac    180
gcggtgatcg tggtctttga cgccaaggcc ccctccttcc gccacgaggc ctacgggggg    240
tacaaggcgg gccgggcccc cacgccggag gactttcccc ggcaactcgc cctcatcaag    300
gagctggtgg acctcctggg gctggcgcgc ctcgaggtcc cgggctacga ggcggacgac    360
gtcctggcca gctggccaa gaaggcggaa aaggagggct acgaggtccg catcctcacc    420
gccgacaaag acctttacca gctccttccc gaccgcatcc acgtcctcca ccccgagggg    480
tacctcatca ccccggcctg gctttgggaa aagtacggcc tgaggcccga ccagtgggcc    540
gactaccggg ccctgaccgg ggacgagtcc gacaaccttc cggggtcaa gggcatcggg    600 gagaagacgg cgaggaagct tctggaggag tgggggagcc tggaagccct cctcaagaac    660
ctggaccggg tgaagcccgc catccgggag aagatcctgg cccacatgga cgatctgaag    720
ctctcctggg acctggccaa ggtgcgcacc gacctgcccc tggaggtgga cttcgccaaa    780
aggcgggagc ccgaccggga gaggcttagg gcctttctgg agaggcttga gtttggcagc    840
ctcctccacg agttcggcct tctggaaagc cccaaggccc tggaggaggc cccctggccc    900
ccgccggaag gggccttcgt gggctttgtg ctttcccgca aggagcccat gtgggccgat    960
cttctggccc tggccgccgc caggggggc cgggtccacc gggcccccga gccttataaa    1020
gccctcaggg acctgaagga ggcgcgggggg cttctcgcca aagacctgag cgttctggcc    1080
ctgagggaag gccttggcct cccgcccggc gacgacccca tgctcctcgc ctacctcctg    1140
gaccctccca caccaccccc cgaggggggt gcccggcgct acggcgggga gtggacggag    1200
gaggcggggg agcgggccgc cctttccgag aggctcttcg ccaacctgtg ggggaggctt    1260 gaggggggagg agaggctcct ttggctttac cgggaggtgg agaggcccct ttccgctgtc    1320
ctggcccaca tggaggccac gggggtgcgc ctggacgtgg cctatctcag ggccttgtcc    1380
ctggaggtgg ccgaggagat cgcccgcctc gaggccgagg tcttccgcct ggccggccac    1440
cccttcaacc tcaactcccg ggaccagctg gaaagggtcc tctttgacga gctagggctt    1500
cccgccatcg gcaagacgga gaagaccggc aagcgctcca ccagcgccgc cgtcctggag    1560
gccctccgcg aggcccaccc catcgtggag aagatcctgc agtaccggga gctcaccaag    1620
ctgaagagca cctacattga cccccttgccg gacctcatcc accccaggac gggccgcctc    1680
cacacccgct caaccagac ggccacggcc acgggcaggc taagtagctc cgatcccaac    1740
ctccagaaca tccccgtccg caccccgctt gggcagagga ccgccgggc cttcatcgcc    1800 gaggaggggt ggctattggt ggccctggac tatagccaga tagagctcag ggtgctggcc    1860
cacctctccg gcgacgagaa cctgatccgg gtcttccagg aggggcggga catccacacg    1920
gagaccgcca gctggatgtt cggcgtcccc cgggaggcc tggacccct gatgcgccgg    1980 gcggccaaga ccatcaactt cggggtcctc tacggcatgt cggcccaccg cctctcccag    2040
gagctagcca tcccttacga ggaggccagg gccttcattg agcgctactt tcagagcttc    2100
cccaaggtgc gggcctggat tgagaagacc ctggaggagg caggaggcg gggtacgtg    2160 gagaccctct tcggccgccg ccgctacgtg ccagacctag aggcccgggt gaagagcgtg    2220
cgggaggcgg ccgagcgcat ggccttcaac atgcccgtcc agggcaccgc cgccgacctc    2280
atgaagctgg ctatggtgaa gctcttcccc aggctggagg aaatgggggc caggatgctc    2340
cttcaggtcc acgacgagct ggtcctcgag gccccaaaag agagggcgga ggccgtggcc    2400
cggctggcca aggaggtcat ggaggggtg tatcccctgg ccgtgccct ggaggtggag    2460
```

```
gtggggatag gggaggactg gctctccgcc aaggagtaa                    2499
```

<210> SEQ ID NO 12
<211> LENGTH: 832
<212> TYPE: PRT
<213> ORGANISM: Thermus aquaticus
<220> FEATURE:
<221> NAME/KEY: MISC_FEATURE
<222> LOCATION: (1)..(832)
<223> OTHER INFORMATION: X can be any amino acid except the wild-type
      residue

<400> SEQUENCE: 12

Met Arg Gly Met Leu Pro Leu Phe Glu Pro Lys Gly Arg Val Leu Leu
1               5                   10                  15

Val Asp Gly His His Leu Ala Tyr Arg Thr Phe His Ala Leu Lys Gly
            20                  25                  30

Leu Thr Thr Ser Arg Gly Glu Pro Val Gln Ala Val Tyr Gly Phe Ala
        35                  40                  45

Lys Ser Leu Leu Lys Ala Leu Lys Glu Asp Xaa Asp Ala Val Ile Val
    50                  55                  60

Val Phe Asp Ala Lys Ala Pro Ser Phe Arg His Glu Ala Tyr Gly Gly
65                  70                  75                  80

Tyr Lys Ala Gly Arg Ala Pro Thr Pro Glu Asp Phe Pro Arg Gln Leu
                85                  90                  95

Ala Leu Ile Lys Glu Leu Val Asp Leu Leu Gly Leu Ala Arg Leu Glu
            100                 105                 110

Val Pro Gly Tyr Glu Ala Asp Asp Val Leu Ala Ser Leu Ala Lys Lys
        115                 120                 125

Ala Glu Lys Glu Gly Tyr Glu Val Arg Ile Leu Thr Ala Asp Lys Asp
    130                 135                 140

Leu Tyr Gln Leu Leu Ser Asp Arg Ile His Val Leu His Pro Glu Gly
145                 150                 155                 160

Tyr Leu Ile Thr Pro Ala Trp Leu Trp Glu Lys Tyr Gly Leu Arg Pro
                165                 170                 175

Asp Gln Trp Ala Asp Tyr Arg Ala Leu Thr Gly Asp Glu Ser Asp Asn
            180                 185                 190

Leu Pro Gly Val Lys Gly Ile Gly Glu Lys Thr Ala Arg Lys Leu Leu
        195                 200                 205

Glu Glu Trp Gly Ser Leu Glu Ala Leu Leu Lys Asn Leu Asp Arg Leu
    210                 215                 220

Lys Pro Ala Ile Arg Glu Lys Ile Leu Ala His Met Asp Asp Leu Lys
225                 230                 235                 240

Leu Ser Trp Asp Xaa Ala Lys Val Arg Thr Asp Leu Pro Leu Glu Val
                245                 250                 255

Asp Phe Ala Lys Arg Arg Glu Pro Asp Arg Glu Arg Leu Arg Ala Phe
            260                 265                 270

Leu Glu Arg Leu Glu Phe Gly Ser Leu Leu His Glu Phe Gly Leu Leu
        275                 280                 285

Glu Ser Pro Lys Ala Leu Glu Glu Ala Pro Trp Pro Pro Pro Glu Gly
    290                 295                 300

Ala Phe Val Gly Phe Val Leu Ser Arg Lys Glu Pro Met Trp Ala Asp
305                 310                 315                 320

Leu Leu Ala Leu Ala Ala Ala Arg Gly Gly Arg Val His Arg Ala Pro
                325                 330                 335

Glu Pro Tyr Lys Ala Leu Arg Asp Leu Lys Glu Ala Arg Gly Leu Leu

```
            340                 345                 350
Ala Lys Asp Leu Ser Val Leu Ala Leu Arg Glu Gly Leu Gly Leu Pro
            355                 360                 365

Pro Gly Asp Asp Pro Met Xaa Leu Ala Tyr Leu Leu Asp Pro Ser Asn
            370                 375                 380

Thr Thr Pro Glu Gly Val Ala Arg Arg Tyr Gly Gly Glu Trp Thr Glu
385                 390                 395                 400

Glu Ala Gly Glu Arg Ala Ala Leu Ser Glu Arg Leu Phe Ala Asn Leu
            405                 410                 415

Trp Gly Arg Leu Glu Gly Glu Arg Leu Leu Trp Leu Tyr Arg Glu
            420                 425                 430

Val Glu Arg Pro Leu Ser Ala Val Leu Ala His Met Glu Ala Thr Gly
            435                 440                 445

Val Arg Leu Asp Val Ala Tyr Leu Arg Ala Leu Ser Leu Glu Val Ala
            450                 455                 460

Glu Glu Ile Ala Arg Leu Glu Ala Glu Val Phe Arg Leu Ala Gly His
465                 470                 475                 480

Pro Phe Asn Leu Asn Ser Arg Asp Gln Leu Glu Arg Val Leu Phe Asp
            485                 490                 495

Glu Leu Gly Leu Pro Ala Ile Gly Lys Thr Xaa Lys Thr Gly Lys Arg
            500                 505                 510

Ser Thr Ser Ala Ala Val Leu Glu Ala Leu Arg Glu Ala His Pro Ile
            515                 520                 525

Val Glu Lys Ile Leu Gln Tyr Arg Glu Leu Thr Lys Leu Lys Ser Thr
            530                 535                 540

Tyr Ile Asp Pro Leu Pro Asp Leu Ile His Pro Arg Thr Gly Arg Leu
545                 550                 555                 560

His Thr Arg Phe Asn Gln Thr Ala Thr Ala Thr Gly Arg Leu Ser Ser
            565                 570                 575

Ser Asp Pro Asn Leu Gln Asn Ile Pro Val Arg Thr Pro Leu Gly Gln
            580                 585                 590

Arg Ile Arg Arg Ala Phe Ile Ala Glu Glu Gly Trp Leu Leu Val Ala
            595                 600                 605

Leu Asp Tyr Ser Gln Ile Glu Leu Arg Val Leu Ala His Leu Ser Gly
            610                 615                 620

Asp Glu Asn Leu Ile Arg Val Phe Gln Glu Gly Arg Asp Ile His Thr
625                 630                 635                 640

Glu Thr Ala Ser Trp Met Phe Gly Val Pro Arg Glu Ala Val Asp Pro
            645                 650                 655

Leu Met Arg Arg Ala Ala Lys Thr Ile Asn Phe Gly Val Leu Tyr Gly
            660                 665                 670

Met Ser Ala His Arg Leu Ser Gln Glu Leu Ala Ile Pro Tyr Glu Glu
            675                 680                 685

Ala Gln Ala Phe Ile Glu Arg Tyr Phe Gln Ser Phe Pro Lys Val Arg
            690                 695                 700

Ala Trp Ile Glu Lys Thr Leu Glu Glu Gly Arg Arg Arg Gly Tyr Val
705                 710                 715                 720

Glu Thr Leu Phe Gly Arg Arg Arg Tyr Val Pro Asp Leu Xaa Ala Arg
            725                 730                 735

Val Lys Ser Val Arg Glu Ala Ala Glu Arg Met Ala Xaa Asn Met Pro
            740                 745                 750

Val Gln Gly Thr Ala Ala Asp Leu Met Lys Leu Ala Met Val Lys Leu
            755                 760                 765
```

```
Phe Pro Arg Leu Glu Glu Met Gly Ala Arg Met Leu Leu Gln Val His
    770                 775                 780

Asp Glu Leu Val Leu Glu Ala Pro Lys Glu Arg Ala Glu Ala Val Ala
785                 790                 795                 800

Arg Leu Ala Lys Glu Val Met Glu Gly Val Tyr Pro Leu Ala Val Pro
                805                 810                 815

Leu Glu Val Glu Val Gly Ile Gly Glu Asp Trp Leu Ser Ala Lys Glu
            820                 825                 830

<210> SEQ ID NO 13
<211> LENGTH: 2499
<212> TYPE: DNA
<213> ORGANISM: Thermus aquaticus
<220> FEATURE:
<221> NAME/KEY: misc_feature
<222> LOCATION: (1)..(2499)
<223> OTHER INFORMATION: nnn can encode for any amino acid except the
      wild-type residue

<400> SEQUENCE: 13
```

| | |
|---|---|
| atgcgtggca tgcttcctct ttttgagccc aagggccggg tcctcctggt ggacggccac | 60 |
| cacctggcct accgcacctt ccacgccctg aagggcctca ccaccagccg gggggagccg | 120 |
| gtgcaggcgg tctacggctt cgccaagagc ctcctcaagg ccctcaagga ggacnnngac | 180 |
| gcggtgatcg tggtctttga cgccaaggcc cctccttcc gccacgaggc ctacgggggg | 240 |
| tacaaggcgg gccggccccc cacgccggag gactttcccc ggcaactcgc cctcatcaag | 300 |
| gagctggtgg acctcctggg gctggcgcgc tcgaggtcc gggctacga gcggacgac | 360 |
| gtcctggcca gctggccaa gaaggcggaa aaggagggct acgaggtccg catcctcacc | 420 |
| gccgacaaag acctttacca gctcctttcc gaccgcatcc acgtcctcca ccccgagggg | 480 |
| tacctcatca ccccggcctg gctttgggaa aagtacggcc tgaggcccga ccagtgggcc | 540 |
| gactaccggg ccctgaccgg ggacgagtcc gacaaccttc cgggggtcaa gggcatcggg | 600 |
| gagaagacgg cgaggaagct tctggaggag tgggggagcc tggaagccct cctcaagaac | 660 |
| ctggaccggg tgaagcccgc catccggga aagatcctgg cccacatgga cgatctgaag | 720 |
| ctctcctggg acnnngccaa ggtgcgcacc gacctgcccc tggaggtgga cttcgccaaa | 780 |
| aggcgggagc ccgaccggga gaggcttagg gcctttctgg agaggcttga gtttggcagc | 840 |
| ctcctccacg agttcggcct tctggaaagc cccaaggccc tggaggaggc ccctggccc | 900 |
| ccgccggaag gggccttcgt gggctttgtg ctttcccgca aggagcccat gtgggccgat | 960 |
| cttctggccc tggccgccgc caggggggc cgggtccacc gggccccga gccttataaa | 1020 |
| gccctcaggg acctgaagga ggcgggggg cttctcgcca aagacctgag cgttctggcc | 1080 |
| ctgagggaag gccttggcct cccgcccggc gacgaccca tgnnnctcgc ctacctcctg | 1140 |
| gaccccttcca acaccacccc cgaggggtg gccggcgct acggcgggga gtggacggag | 1200 |
| gaggcggggg agcgggccgc cctttccgag aggctcttcg ccaacctgtg ggggaggctt | 1260 |
| gaggggagg agaggctcct ttggctttac cgggaggtgg agaggcccct ttccgctgtc | 1320 |
| ctggcccaca tggaggccac ggggtgcgc ctggacgtgg cctatctcag ggccttgtcc | 1380 |
| ctggaggtgg ccgaggagat cgcccgcctc gaggccgagg tcttccgcct ggccggccac | 1440 |
| cccttcaacc tcaactcccg ggaccagctg gaaagggtcc tctttgacga gctagggctt | 1500 |
| cccgccatcg gcaagacgnn naagaccggc aagcgctcca ccagcgccgc cgtcctggag | 1560 |
| gccctccgcg aggcccaccc catcgtggag aagatcctgc agtaccggga gctcaccaag | 1620 |

-continued

```
ctgaagagca cctacattga ccccttgccg gacctcatcc accccaggac gggccgcctc    1680
cacacccgct tcaaccagac ggccacggcc acgggcaggc taagtagctc cgatcccaac    1740
ctccagaaca tccccgtccg cacccgctt gggcagagga tccgccgggc cttcatcgcc    1800
gaggaggggt ggctattggt ggccctggac tatagccaga tagagctcag ggtgctggcc    1860
cacctctccg gcgacgagaa cctgatccgg gtcttccagg aggggcggga catccacacg    1920
gagaccgcca gctggatgtt cggcgtcccc cgggaggccg tggaccccct gatgcgccgg    1980
gcggccaaga ccatcaactt cggggtcctc tacggcatgt cggcccaccg cctctcccag    2040
gagctagcca tcccttacga ggaggcccag gccttcattg agcgctactt tcagagcttc    2100
cccaaggtgc gggcctggat tgagaagacc ctggaggagg caggaggcg ggggtacgtg    2160 gagaccctct tcggccgccg ccgctacgtg ccagacctan nngcccgggt gaagagcgtg    2220
cgggaggcgg ccgagcgcat ggccnnnaac atgcccgtcc agggcaccgc cgccgacctc    2280
atgaagctgg ctatggtgaa gctcttcccc aggctggagg aaatgggggc caggatgctc    2340
cttcaggtcc acgacgagct ggtcctcgag gccccaaaag agagggcgga ggccgtggcc    2400
cggctggcca aggaggtcat ggaggggtg tatcccctgg ccgtgcccct ggaggtggag    2460
gtggggatag gggaggactg gctctccgcc aaggagtaa                          2499
```

<210> SEQ ID NO 14
<211> LENGTH: 832
<212> TYPE: PRT
<213> ORGANISM: Thermus aquaticus
<220> FEATURE:
<221> NAME/KEY: MISC_FEATURE
<222> LOCATION: (1)..(832)
<223> OTHER INFORMATION: X can be any amino acid except for the
      wild-type residue

<400> SEQUENCE: 14

```
Met Arg Gly Met Leu Pro Leu Phe Glu Pro Lys Gly Arg Val Leu Leu
1               5                   10                  15

Val Asp Gly His His Leu Ala Tyr Arg Thr Phe His Ala Leu Lys Gly
                20                  25                  30

Leu Thr Thr Ser Arg Gly Glu Pro Val Gln Ala Val Tyr Gly Phe Ala
            35                  40                  45

Lys Ser Leu Leu Lys Ala Leu Lys Glu Asp Xaa Asp Ala Val Ile Val
        50                  55                  60

Val Phe Asp Ala Lys Ala Pro Ser Phe Arg His Glu Ala Tyr Gly Gly
65                  70                  75                  80

Tyr Lys Ala Gly Arg Ala Pro Thr Pro Glu Asp Phe Pro Arg Gln Leu
                85                  90                  95

Ala Leu Ile Lys Glu Leu Val Asp Leu Leu Gly Leu Ala Arg Leu Glu
            100                 105                 110

Val Pro Gly Tyr Glu Ala Asp Asp Val Leu Ala Ser Leu Ala Lys Lys
        115                 120                 125

Ala Glu Lys Glu Gly Tyr Glu Val Arg Ile Leu Thr Ala Asp Lys Asp
    130                 135                 140

Leu Tyr Gln Leu Leu Ser Asp Arg Ile His Xaa Leu His Pro Glu Gly
145                 150                 155                 160

Tyr Leu Ile Thr Pro Ala Trp Leu Trp Glu Lys Tyr Gly Leu Arg Pro
                165                 170                 175

Asp Gln Trp Ala Asp Tyr Arg Ala Leu Thr Gly Asp Glu Ser Asp Asn
            180                 185                 190
```

```
Leu Pro Gly Val Lys Gly Ile Gly Glu Lys Thr Ala Arg Lys Leu Leu
            195                 200                 205

Glu Glu Trp Gly Ser Leu Glu Ala Leu Leu Lys Asn Leu Asp Arg Leu
210                 215                 220

Lys Pro Ala Ile Arg Glu Lys Ile Leu Ala His Met Asp Asp Leu Lys
225                 230                 235                 240

Leu Ser Trp Asp Xaa Ala Lys Val Arg Thr Asp Leu Pro Leu Glu Val
                245                 250                 255

Asp Phe Ala Lys Arg Arg Glu Pro Asp Arg Glu Arg Leu Arg Ala Phe
                260                 265                 270

Leu Glu Arg Leu Glu Phe Gly Ser Leu Leu His Glu Phe Gly Leu Leu
            275                 280                 285

Glu Ser Pro Lys Ala Leu Glu Glu Ala Pro Trp Pro Pro Pro Glu Gly
290                 295                 300

Ala Phe Val Gly Phe Val Leu Ser Arg Lys Glu Pro Met Trp Ala Asp
305                 310                 315                 320

Leu Leu Ala Leu Ala Ala Ala Arg Gly Gly Arg Val His Arg Ala Pro
                325                 330                 335

Glu Pro Tyr Lys Ala Leu Arg Asp Leu Lys Glu Ala Arg Gly Leu Leu
            340                 345                 350

Ala Lys Asp Leu Ser Val Leu Ala Leu Arg Glu Gly Leu Gly Leu Pro
            355                 360                 365

Pro Gly Asp Asp Pro Met Xaa Leu Ala Tyr Leu Leu Asp Pro Ser Asn
370                 375                 380

Thr Thr Pro Glu Gly Val Ala Arg Arg Tyr Gly Gly Glu Trp Thr Glu
385                 390                 395                 400

Glu Ala Gly Glu Arg Ala Ala Leu Ser Glu Arg Leu Phe Ala Asn Leu
                405                 410                 415

Trp Gly Arg Leu Glu Gly Glu Glu Arg Leu Leu Trp Leu Tyr Arg Glu
                420                 425                 430

Val Glu Arg Pro Leu Ser Ala Val Leu Ala His Met Glu Ala Thr Gly
            435                 440                 445

Val Arg Leu Asp Val Ala Tyr Leu Arg Ala Leu Ser Leu Glu Val Ala
            450                 455                 460

Glu Glu Ile Ala Arg Leu Glu Ala Glu Val Phe Arg Leu Ala Gly His
465                 470                 475                 480

Pro Phe Asn Leu Asn Ser Arg Asp Gln Leu Glu Arg Val Leu Phe Asp
                485                 490                 495

Glu Leu Gly Leu Pro Ala Ile Gly Lys Thr Xaa Xaa Thr Gly Lys Arg
            500                 505                 510

Ser Thr Ser Ala Ala Val Leu Glu Ala Leu Arg Glu Ala His Pro Ile
            515                 520                 525

Val Glu Lys Ile Leu Gln Tyr Arg Glu Leu Thr Lys Leu Lys Ser Thr
530                 535                 540

Tyr Ile Asp Pro Leu Pro Asp Leu Ile His Pro Arg Thr Gly Arg Leu
545                 550                 555                 560

His Thr Arg Phe Asn Gln Thr Ala Thr Ala Thr Gly Arg Leu Ser Ser
                565                 570                 575

Ser Asp Pro Asn Leu Gln Asn Ile Pro Val Arg Thr Pro Leu Gly Gln
                580                 585                 590

Arg Ile Arg Arg Ala Phe Ile Ala Glu Glu Gly Trp Leu Leu Val Ala
            595                 600                 605
```

```
Leu Asp Tyr Ser Gln Ile Glu Leu Arg Val Leu Ala His Leu Ser Gly
    610                 615                 620

Asp Glu Asn Leu Ile Arg Val Phe Gln Glu Gly Arg Asp Ile His Thr
625                 630                 635                 640

Glu Thr Ala Ser Trp Met Phe Gly Val Pro Arg Glu Ala Val Asp Pro
                645                 650                 655

Leu Met Arg Arg Ala Ala Lys Thr Ile Asn Phe Gly Val Leu Tyr Gly
                660                 665                 670

Met Ser Ala His Arg Leu Ser Gln Glu Leu Ala Ile Pro Tyr Glu Glu
                675                 680                 685

Ala Gln Ala Phe Ile Glu Arg Tyr Phe Gln Ser Phe Pro Lys Val Arg
690                 695                 700

Ala Trp Ile Glu Lys Thr Leu Glu Glu Gly Arg Arg Arg Gly Tyr Val
705                 710                 715                 720

Glu Thr Leu Phe Gly Arg Arg Arg Tyr Val Pro Asp Leu Xaa Ala Arg
                725                 730                 735

Val Lys Ser Val Arg Glu Ala Ala Glu Arg Met Ala Xaa Asn Met Pro
            740                 745                 750

Val Gln Gly Thr Ala Ala Asp Leu Met Lys Leu Ala Met Val Lys Leu
                755                 760                 765

Phe Pro Arg Leu Glu Glu Met Gly Ala Arg Met Leu Leu Gln Val His
        770                 775                 780

Asp Glu Leu Val Leu Glu Ala Pro Lys Glu Arg Ala Glu Ala Val Ala
785                 790                 795                 800

Arg Leu Ala Lys Glu Val Met Glu Gly Val Tyr Pro Leu Ala Val Pro
                805                 810                 815

Leu Glu Val Glu Val Gly Ile Gly Glu Asp Trp Leu Ser Ala Lys Glu
                820                 825                 830

<210> SEQ ID NO 15
<211> LENGTH: 2499
<212> TYPE: DNA
<213> ORGANISM: Thermus aquaticus
<220> FEATURE:
<221> NAME/KEY: misc_feature
<222> LOCATION: (1)..(2499)
<223> OTHER INFORMATION: nnn can encode for any amino acid except for
      the wild-type residue

<400> SEQUENCE: 15
atgcgtggca tgcttcctct ttttgagccc aagggccggg tcctcctggt ggacggccac      60
cacctggcct accgcacctt ccacgccctg aagggcctca ccaccagccg ggggagccg      120 gtgcaggcgg tctacggctt cgccaagagc ctcctcaagg ccctcaagga ggacnnngac     180
gcggtgatcg tggtctttga cgccaaggcc cctccttcc gccacgaggc ctacggggg       240 tacaaggcgg ccgggcccc cacgccggag gactttcccc ggcaactcgc cctcatcaag      300
gagctggtgg acctcctggg gctggcgcgc ctcgaggtcc cggctacga gcggacgac       360 gtcctggcca gcctggccaa gaaggcggaa aaggagggct acgaggtccg catcctcacc    420
gccgacaaag accttttacca gctcctttcc gaccgcatcc acnnnctcca ccccgagggg    480
tacctcatca ccccggcctg gctttgggaa agtacggcc tgaggcccga ccagtgggcc     540
gactaccggg ccctgaccgg ggacgagtcc gacaaccttc cggggtcaa gggcatcggg     600 gagaagacgc gaggaagct tctggaggag tggggagcc tggaagccct cctcaagaac      660
ctggaccggc tgaagcccgc catccgggag aagatcctgg cccacatgga cgatctgaag     720
```

-continued

| | |
|---|---|
| ctctcctggg acnnngccaa ggtgcgcacc gacctgcccc tggaggtgga cttcgccaaa | 780 |
| aggcgggagc ccgaccggga gaggcttagg gcctttctgg agaggcttga gtttggcagc | 840 |
| ctcctccacg agttcggcct tctggaaagc cccaaggccc tggaggaggc ccctggccc | 900 |
| ccgccggaag gggccttcgt gggctttgtg ctttcccgca aggagcccat gtgggccgat | 960 |
| cttctggccc tggccgccgc caggggggc cgggtccacc gggcccccga gccttataaa | 1020 |
| gccctcaggg acctgaagga ggcgcggggg cttctcgcca agacctgag cgttctggcc | 1080 |
| ctgagggaag gccttggcct cccgcccggc gacgacccca tgnnnctcgc ctacctcctg | 1140 |
| gaccctccca acaccacccc cgagggggtg gcccggcgct acggcgggga gtggacggag | 1200 |
| gaggcggggg agcgggccgc cctttccgag aggctcttcg ccaacctgtg ggggaggctt | 1260 |
| gaggggagg agaggctcct ttggctttac cgggaggtgg agaggcccct ttccgctgtc | 1320 |
| ctggcccaca tggaggccac ggggtgcgc ctggacgtgg cctatctcag ggccttgtcc | 1380 |
| ctggaggtgg ccgaggagat cgcccgcctc gaggccgagg tcttccgcct ggccggccac | 1440 |
| cccttcaacc tcaactcccg ggaccagctg gaaagggtcc tctttgacga gctagggctt | 1500 |
| cccgccatcg gcaagacgnn nnnnaccggc aagcgctcca ccagcgccgc cgtcctggag | 1560 |
| gccctccgcg aggcccaccc catcgtggag aagatcctgc agtaccggga gctcaccaag | 1620 |
| ctgaagagca cctacattga ccccttgccg gacctcatcc accccaggac gggccgcctc | 1680 |
| cacacccgct tcaaccagac ggccacggcc acgggcaggc taagtagctc cgatcccaac | 1740 |
| ctccagaaca tccccgtccg caccccgctt gggcagagga tccgccgggc cttcatcgcc | 1800 |
| gaggaggggt ggctattggt ggccctggac tatagccaga tagagctcag ggtgctggcc | 1860 |
| cacctctccg gcgacgagaa cctgatccgg gtcttccagg aggggcggga catccacacg | 1920 |
| gagaccgcca gctggatgtt cggcgtcccc cgggaggccg tggaccccct gatgcgccgg | 1980 |
| gcggccaaga ccatcaactt cggggtcctc tacggcatgt cggcccaccg cctctcccag | 2040 |
| gagctagcca tcccttacga ggaggcccag gccttcattg agcgctactt tcagagcttc | 2100 |
| cccaaggtgc gggcctggat tgagaagacc ctggaggagg gcaggaggcg ggggtacgtg | 2160 |
| gagaccctct cggccgccg ccgctacgtg ccagacctan nngcccgggt gaagagcgtg | 2220 |
| cgggaggcgg ccgagcgcat ggccnnnaac atgcccgtcc agggcaccgc cgccgacctc | 2280 |
| atgaagctgg ctatggtgaa gctcttcccc aggctggagg aaatggggc caggatgctc | 2340 |
| cttcaggtcc acgacgagct ggtcctcgag gccccaaaag agagggcgga ggccgtggcc | 2400 |
| cggctggcca aggaggtcat ggaggggtg tatcccctgg ccgtgcccct ggaggtggag | 2460 |
| gtggggatag gggaggactg gctctccgcc aaggagtaa | 2499 |

<210> SEQ ID NO 16
<211> LENGTH: 832
<212> TYPE: PRT
<213> ORGANISM: Thermus aquaticus
<220> FEATURE:
<221> NAME/KEY: MISC_FEATURE
<222> LOCATION: (1)..(832)
<223> OTHER INFORMATION: X can be any amino acid except for the
      wild-type residue

<400> SEQUENCE: 16

Met Arg Gly Met Leu Pro Leu Phe Glu Pro Lys Gly Arg Val Leu Leu
1               5                   10                  15

Val Asp Gly His His Leu Ala Tyr Arg Thr Phe His Ala Leu Lys Gly
            20                  25                  30

-continued

```
Leu Thr Thr Ser Arg Gly Glu Pro Val Gln Ala Val Tyr Gly Phe Ala
         35                  40                  45

Lys Ser Leu Leu Lys Ala Leu Lys Glu Asp Xaa Asp Ala Val Ile Val
 50                  55                  60

Val Phe Asp Ala Lys Ala Pro Ser Phe Arg His Glu Ala Tyr Gly Gly
 65                  70                  75                  80

Tyr Lys Ala Gly Arg Ala Pro Thr Pro Glu Asp Phe Pro Arg Gln Leu
                 85                  90                  95

Ala Leu Ile Lys Glu Leu Val Asp Leu Gly Leu Ala Arg Leu Glu
                100                 105                 110

Val Pro Gly Tyr Glu Ala Asp Asp Val Leu Ala Ser Leu Ala Lys Lys
            115                 120                 125

Ala Glu Lys Glu Gly Tyr Glu Val Arg Ile Leu Thr Ala Asp Lys Asp
    130                 135                 140

Leu Tyr Gln Leu Leu Ser Asp Arg Ile His Val Leu His Pro Glu Gly
145                 150                 155                 160

Tyr Leu Ile Thr Pro Ala Trp Leu Trp Glu Lys Tyr Gly Leu Arg Pro
                165                 170                 175

Asp Gln Trp Ala Asp Tyr Arg Ala Leu Thr Gly Asp Glu Ser Asp Asn
            180                 185                 190

Leu Pro Gly Val Lys Gly Ile Gly Glu Lys Thr Ala Arg Lys Leu Leu
        195                 200                 205

Glu Glu Trp Gly Ser Leu Glu Ala Leu Leu Lys Asn Leu Asp Arg Leu
    210                 215                 220

Lys Pro Ala Ile Arg Glu Lys Ile Leu Ala His Met Asp Asp Leu Lys
225                 230                 235                 240

Leu Ser Trp Asp Xaa Ala Lys Val Arg Thr Asp Leu Pro Leu Glu Val
                245                 250                 255

Asp Phe Ala Lys Arg Arg Glu Pro Asp Arg Glu Arg Leu Arg Ala Phe
            260                 265                 270

Leu Glu Arg Leu Glu Phe Gly Ser Leu Leu His Glu Phe Gly Leu Leu
        275                 280                 285

Glu Ser Pro Lys Ala Leu Glu Glu Ala Pro Trp Pro Pro Pro Glu Gly
    290                 295                 300

Ala Phe Val Gly Phe Val Leu Ser Arg Lys Glu Pro Met Trp Ala Asp
305                 310                 315                 320

Leu Leu Ala Leu Ala Ala Ala Arg Gly Gly Arg Val His Arg Ala Pro
                325                 330                 335

Glu Pro Tyr Lys Ala Leu Arg Asp Leu Lys Glu Ala Arg Gly Leu Leu
            340                 345                 350

Ala Lys Asp Leu Ser Val Leu Ala Leu Arg Glu Gly Leu Gly Leu Pro
        355                 360                 365

Pro Gly Asp Asp Pro Met Xaa Leu Ala Tyr Leu Leu Asp Pro Ser Asn
    370                 375                 380

Thr Thr Pro Glu Gly Val Ala Arg Arg Tyr Gly Gly Glu Trp Thr Glu
385                 390                 395                 400

Glu Ala Gly Glu Arg Ala Ala Leu Ser Glu Arg Leu Phe Ala Asn Leu
                405                 410                 415

Trp Gly Arg Leu Glu Gly Glu Glu Arg Leu Leu Trp Leu Tyr Arg Glu
            420                 425                 430

Val Glu Arg Pro Leu Ser Ala Val Leu Ala His Met Glu Ala Thr Gly
        435                 440                 445

Val Arg Leu Asp Val Ala Tyr Leu Arg Ala Leu Ser Leu Glu Val Ala
```

```
                450                 455                 460
Glu Ile Ala Arg Leu Glu Ala Glu Val Phe Arg Leu Ala Gly His
465                 470                 475                 480

Pro Phe Asn Leu Asn Ser Arg Asp Gln Leu Glu Arg Val Leu Phe Asp
                485                 490                 495

Glu Leu Gly Leu Pro Ala Ile Gly Lys Thr Xaa Xaa Thr Gly Lys Arg
                500                 505                 510

Ser Thr Ser Ala Ala Val Leu Glu Ala Leu Arg Glu Ala His Pro Ile
                515                 520                 525

Val Glu Lys Ile Leu Gln Tyr Arg Glu Leu Thr Lys Leu Lys Ser Thr
530                 535                 540

Tyr Ile Asp Pro Leu Pro Asp Leu Ile His Pro Arg Thr Gly Arg Leu
545                 550                 555                 560

His Thr Arg Phe Asn Gln Thr Ala Thr Ala Thr Gly Arg Leu Ser Ser
                565                 570                 575

Ser Asp Pro Asn Leu Gln Asn Ile Pro Val Arg Thr Pro Leu Gly Gln
                580                 585                 590

Arg Ile Arg Arg Ala Phe Ile Ala Glu Glu Gly Trp Leu Leu Val Ala
                595                 600                 605

Leu Asp Tyr Ser Gln Ile Glu Leu Arg Val Leu Ala His Leu Ser Gly
                610                 615                 620

Asp Glu Asn Leu Ile Arg Val Phe Gln Glu Gly Arg Asp Ile His Thr
625                 630                 635                 640

Glu Thr Ala Ser Trp Met Phe Gly Val Pro Arg Glu Ala Val Asp Pro
                645                 650                 655

Leu Met Arg Arg Ala Ala Lys Thr Ile Asn Phe Gly Val Leu Tyr Gly
                660                 665                 670

Met Ser Ala His Arg Leu Ser Gln Glu Leu Ala Ile Pro Tyr Glu Glu
                675                 680                 685

Ala Gln Ala Phe Ile Glu Arg Tyr Phe Gln Ser Phe Pro Lys Val Arg
                690                 695                 700

Ala Trp Ile Glu Lys Thr Leu Glu Glu Gly Arg Arg Arg Gly Tyr Val
705                 710                 715                 720

Glu Thr Leu Phe Gly Arg Arg Arg Tyr Val Pro Asp Leu Xaa Ala Arg
                725                 730                 735

Val Lys Ser Val Arg Glu Ala Ala Glu Arg Met Ala Xaa Asn Met Pro
                740                 745                 750

Val Gln Gly Thr Ala Ala Asp Leu Met Lys Leu Ala Met Val Lys Leu
                755                 760                 765

Phe Pro Arg Leu Glu Glu Met Gly Ala Arg Met Leu Leu Gln Val His
                770                 775                 780

Asp Glu Leu Val Leu Glu Ala Pro Lys Glu Arg Ala Glu Ala Val Ala
785                 790                 795                 800

Arg Leu Ala Lys Glu Val Met Glu Gly Val Tyr Pro Leu Ala Val Pro
                805                 810                 815

Leu Glu Val Glu Val Gly Ile Gly Glu Asp Trp Leu Ser Ala Lys Glu
                820                 825                 830

<210> SEQ ID NO 17
<211> LENGTH: 2499
<212> TYPE: DNA
<213> ORGANISM: Thermus aquaticus
<220> FEATURE:
<221> NAME/KEY: misc_feature
<222> LOCATION: (1)..(2499)
```

<223> OTHER INFORMATION: X can encode for any amino acid except for the
     wild-type residue

<400> SEQUENCE: 17

```
atgcgtggca tgcttcctct ttttgagccc aagggccggg tcctcctggt ggacggccac     60
cacctggcct accgcacctt ccacgccctg aagggcctca ccaccagccg gggggagccg    120
gtgcaggcgg tctacggctt cgccaagagc ctcctcaagg ccctcaagga ggacnnngac    180
gcggtgatcg tggtctttga cgccaaggcc cctccttcc gccacgaggc ctacgggggg     240
tacaaggcgg gccggccccc cacgccggag gactttcccc ggcaactcgc cctcatcaag    300
gagctggtgg acctcctggg gctggcgcgc ctcgaggtcc cgggctacga ggcggacgac    360
gtcctggcca gctggccaa gaaggcggaa aaggagggct acgaggtccg catcctcacc    420
gccgacaaag acctttacca gctcctttcc gaccgcatcc acgtcctcca ccccgagggg    480
tacctcatca ccccggcctg gctttgggaa aagtacggcc tgaggcccga ccagtgggcc    540
gactaccggg ccctgaccgg ggacgagtcc gacaaccttc cggggtcaa gggcatcggg     600
gagaagacgg cgaggaagct tctggaggag tggggagcc tggaagccct cctcaagaac    660
ctggaccggt tgaagcccgc catccgggag aagatcctgg cccacatgga cgatctgaag    720
ctctcctggg acnnngccaa ggtgcgcacc gacctgcccc tggaggtgga cttcgccaaa    780
aggcgggagc ccgaccggga gaggcttagg gcctttctgg agaggcttga gtttggcagc    840
ctcctccacg agttcggcct tctggaaagc cccaaggccc tggaggaggc ccctggccc    900
ccgccggaag gggccttcgt gggctttgtg ctttcccgca aggagcccat gtgggccgat    960
cttctggccc tggccgccgc cagggggggc cgggtccacc gggcccccga gccttataaa   1020
gccctcaggg acctgaagga ggcgcgggg cttctcgcca aagacctgag cgttctggcc   1080
ctgagggaag gccttggcct cccgcccggc gacgaccca tgnnnctcgc ctacctcctg   1140
gacccttcca acaccacccc cgaggggtg gccggcgct acggcgggga gtggacggag   1200
gaggcggggg agcgggccgc cctttccgag aggctcttcg ccaacctgtg ggggaggctt   1260
gaggggagg agaggctcct ttggctttac cgggaggtgg agaggcccct ttccgctgtc   1320
ctggcccaca tggaggccac ggggggtgcgc ctggacgtgg cctatctcag ggccttgtcc   1380
ctggaggtgg ccgaggagat cgcccgcctc gaggccgagg tcttccgcct ggccggccac   1440
cccttcaacc tcaactcccg ggaccagctg gaaagggtcc tctttgacga gctagggctt   1500
cccgccatcg gcaagacgnn nnnnaccggc aagcgctcca ccagcgccgc cgtcctggag   1560
gccctccgcg aggcccaccc catcgtggag aagatcctgc agtaccggga gctcaccaag   1620
ctgaagagca cctacattga ccccttgccg gacctcatcc accccaggac gggccgcctc   1680
cacacccgct tcaaccagac ggccacggcc acgggcaggt aagtagctc cgatcccaac   1740
ctccagaaca tccccgtccg caccccgctt gggcagagga tccgccgggc cttcatcgcc   1800
gaggaggggt ggctattggt ggccctggac tatagccaga tagagctcag ggtgctggcc   1860
cacctctccg gcgacgagaa cctgatccgg gtcttccagg aggggcggga catccacacg   1920
gagaccgcca gctggatgtt cggcgtcccc cgggaggccg tggacccct gatgcgccgg   1980
gcggccaaga ccatcaactt cggggtcctc tacggcatgt cggcccaccg cctctcccag   2040
gagctagcca tcccttacga ggaggcccag gccttcattg agcgctactt tcagagcttc   2100
cccaaggtgc gggcctggat tgagaagacc ctggaggagg caggaggcg ggggtacgtg   2160
gagaccctct tcggccgccg ccgctacgtg ccagacctan nngcccgggt gaagagcgtg   2220
```

```
cgggaggcgg ccgagcgcat ggccnnnaac atgcccgtcc agggcaccgc cgccgacctc      2280
atgaagctgg ctatggtgaa gctcttcccc aggctggagg aaatggggc caggatgctc       2340 cttcaggtcc acgacgagct ggtcctcgag gccccaaaag agagggcgga ggccgtggcc      2400
cggctggcca aggaggtcat ggaggggtg tatcccctgg ccgtgcccct ggaggtggag       2460
gtggggatag ggaggactg gctctccgcc aaggagtaa                              2499
```

<210> SEQ ID NO 18
<211> LENGTH: 832
<212> TYPE: PRT
<213> ORGANISM: Thermus aquaticus
<220> FEATURE:
<221> NAME/KEY: MISC_FEATURE
<222> LOCATION: (1)..(832)
<223> OTHER INFORMATION: X can be any amino acid except for the
      wild-type residue

<400> SEQUENCE: 18

```
Met Arg Gly Met Leu Pro Leu Phe Glu Pro Lys Gly Arg Val Leu Leu
1               5                   10                  15

Val Asp Gly His His Leu Ala Tyr Arg Thr Phe His Ala Leu Lys Gly
                20                  25                  30

Leu Thr Thr Ser Arg Gly Glu Pro Val Gln Ala Val Tyr Gly Phe Ala
            35                  40                  45

Lys Ser Leu Leu Lys Ala Leu Lys Glu Asp Xaa Asp Ala Val Ile Val
        50                  55                  60

Val Phe Asp Ala Lys Ala Pro Ser Phe Arg His Glu Ala Tyr Gly Gly
65                  70                  75                  80

Tyr Lys Ala Gly Arg Ala Pro Thr Pro Glu Asp Phe Pro Arg Gln Leu
                85                  90                  95

Ala Leu Ile Lys Glu Leu Val Asp Leu Leu Gly Leu Ala Arg Leu Glu
            100                 105                 110

Val Pro Gly Tyr Glu Ala Asp Asp Val Leu Ala Ser Leu Ala Lys Lys
        115                 120                 125

Ala Glu Lys Glu Gly Tyr Glu Val Arg Ile Leu Thr Ala Asp Lys Asp
    130                 135                 140

Leu Tyr Gln Leu Leu Ser Asp Arg Ile His Xaa Leu His Pro Glu Gly
145                 150                 155                 160

Tyr Leu Ile Thr Pro Ala Trp Leu Trp Glu Lys Tyr Gly Leu Arg Pro
                165                 170                 175

Asp Gln Trp Ala Asp Tyr Arg Ala Leu Thr Gly Asp Glu Ser Asp Asn
            180                 185                 190

Leu Pro Gly Val Lys Gly Ile Gly Glu Lys Thr Ala Arg Lys Leu Leu
        195                 200                 205

Glu Glu Trp Gly Ser Leu Glu Ala Leu Leu Lys Asn Leu Asp Arg Leu
    210                 215                 220

Lys Pro Ala Ile Arg Glu Lys Ile Leu Ala His Met Asp Asp Leu Lys
225                 230                 235                 240

Leu Ser Trp Asp Xaa Ala Lys Val Arg Thr Asp Leu Pro Leu Glu Val
                245                 250                 255

Asp Phe Ala Lys Arg Arg Glu Pro Asp Arg Glu Arg Leu Arg Ala Phe
            260                 265                 270

Leu Glu Arg Leu Glu Phe Gly Ser Leu Leu His Glu Phe Gly Leu Leu
        275                 280                 285

Glu Ser Pro Lys Ala Leu Glu Glu Ala Pro Trp Pro Pro Glu Gly
    290                 295                 300
```

```
Ala Phe Val Gly Phe Val Leu Ser Arg Lys Glu Pro Met Trp Ala Asp
305                 310                 315                 320

Leu Leu Ala Leu Ala Ala Arg Gly Gly Arg Val His Arg Ala Pro
            325                 330                 335

Glu Pro Tyr Lys Ala Leu Arg Asp Leu Lys Glu Ala Arg Gly Leu Leu
            340                 345                 350

Ala Lys Asp Leu Ser Val Leu Ala Leu Arg Glu Gly Leu Gly Leu Pro
            355                 360                 365

Pro Gly Asp Asp Pro Met Xaa Leu Ala Tyr Leu Leu Asp Pro Ser Asn
370                 375                 380

Thr Thr Pro Glu Gly Val Ala Arg Arg Tyr Gly Gly Glu Trp Thr Glu
385                 390                 395                 400

Glu Ala Gly Glu Arg Ala Ala Leu Ser Glu Arg Leu Phe Ala Asn Leu
            405                 410                 415

Trp Gly Arg Leu Glu Gly Glu Arg Leu Leu Trp Leu Tyr Arg Glu
            420                 425                 430

Val Glu Arg Pro Leu Ser Ala Val Leu Ala His Met Glu Ala Thr Gly
            435                 440                 445

Val Arg Leu Asp Val Ala Tyr Leu Arg Ala Leu Ser Leu Glu Val Ala
            450                 455                 460

Glu Glu Ile Ala Arg Leu Glu Ala Glu Val Phe Arg Leu Ala Gly His
465                 470                 475                 480

Pro Phe Asn Leu Asn Ser Arg Asp Gln Leu Glu Arg Val Leu Phe Asp
            485                 490                 495

Glu Leu Gly Leu Pro Ala Ile Gly Lys Thr Xaa Lys Thr Gly Lys Arg
            500                 505                 510

Ser Thr Ser Ala Ala Val Leu Glu Ala Leu Arg Glu Ala His Pro Ile
            515                 520                 525

Val Glu Lys Ile Leu Gln Tyr Arg Glu Leu Thr Lys Leu Lys Ser Thr
530                 535                 540

Tyr Ile Asp Pro Leu Pro Asp Leu Ile His Pro Arg Thr Gly Arg Leu
545                 550                 555                 560

His Thr Arg Phe Asn Gln Thr Ala Thr Ala Thr Gly Arg Leu Ser Ser
            565                 570                 575

Ser Asp Pro Asn Leu Gln Asn Ile Pro Val Arg Thr Pro Leu Gly Gln
            580                 585                 590

Arg Ile Arg Arg Ala Phe Ile Ala Glu Glu Gly Trp Leu Leu Val Ala
            595                 600                 605

Leu Asp Tyr Ser Gln Ile Glu Leu Arg Val Leu Ala His Leu Ser Gly
            610                 615                 620

Asp Glu Asn Leu Ile Arg Val Phe Gln Glu Gly Arg Asp Ile His Thr
625                 630                 635                 640

Glu Thr Ala Ser Trp Met Phe Gly Val Pro Arg Glu Ala Val Asp Pro
            645                 650                 655

Leu Met Arg Arg Ala Ala Lys Thr Ile Asn Phe Gly Val Leu Tyr Gly
            660                 665                 670

Met Ser Ala His Arg Leu Ser Gln Glu Leu Ala Ile Pro Tyr Glu Glu
            675                 680                 685

Ala Gln Ala Phe Ile Glu Arg Tyr Phe Gln Ser Phe Pro Lys Val Arg
            690                 695                 700

Ala Trp Ile Glu Lys Thr Leu Glu Glu Gly Arg Arg Arg Gly Tyr Val
705                 710                 715                 720
```

```
Glu Thr Leu Phe Gly Arg Arg Arg Tyr Val Pro Asp Leu Xaa Ala Arg
            725                 730                 735

Val Lys Ser Val Arg Glu Ala Ala Glu Arg Met Ala Xaa Asn Met Pro
        740                 745                 750

Val Gln Gly Thr Ala Ala Asp Leu Met Lys Leu Ala Met Val Lys Leu
    755                 760                 765

Phe Pro Arg Leu Glu Glu Met Gly Ala Arg Met Leu Leu Gln Val His
770                 775                 780

Asp Glu Leu Val Leu Glu Ala Pro Lys Glu Arg Ala Glu Ala Val Ala
785                 790                 795                 800

Arg Leu Ala Lys Glu Val Met Glu Gly Val Tyr Pro Leu Ala Val Pro
                805                 810                 815

Leu Glu Val Glu Val Gly Ile Gly Glu Asp Trp Leu Ser Ala Lys Glu
            820                 825                 830

<210> SEQ ID NO 19
<211> LENGTH: 2499
<212> TYPE: DNA
<213> ORGANISM: Thermus aquaticus
<220> FEATURE:
<221> NAME/KEY: misc_feature
<222> LOCATION: (1)..(2499)
<223> OTHER INFORMATION: nnn can encode for any amino acid except for
      the wild-type residue

<400> SEQUENCE: 19
atgcgtggca tgcttcctct ttttgagccc aagggccggg tcctcctggt ggacggccac      60
cacctggcct accgcacctt ccacgccctg aagggcctca ccaccagccg ggggagccg      120 gtgcaggcgg tctacggctt cgccaagagc ctcctcaagg ccctcaagga ggacnnngac     180
gcggtgatcg tggtctttga cgccaaggcc cctccttcc gccacgaggc ctacgggggg      240
tacaaggcgg ccgggccccc cacgccggag gactttcccc ggcaactcgc cctcatcaag      300
gagctggtgg acctcctggg gctggcgcgc tcgaggtcc cgggctacga ggcggacgac      360
gtcctggcca gcctggccaa gaaggcggaa aaggagggct acgaggtccg catcctcacc      420
gccgacaaag acctttacca gctcctttcc gaccgcatcc acnnnctcca ccccgagggg      480
tacctcatca cccccggcct gctttgggaa agtacggcc tgaggcccga ccagtgggcc      540
gactaccggg ccctgaccgg ggacgagtcc gacaaccttc ccgggtcaa gggcatcggg      600 gagaagacgg cgaggaagct tctggaggag tgggggagcc tggaagcct cctcaagaac      660 ctggaccggc tgaagcccgc catccggag aagatcctgg cccacatgga cgatctgaag      720
ctctcctggg acnnngccaa ggtgcgcacc gacctgcccc tggaggtgga cttcgccaaa      780
aggcgggagc ccgaccggga gaggcttagg gcctttctgg agaggcttga gtttggcagc      840
ctcctccacg agttcggcct tctggaaagc cccaaggccc tggaggaggc ccctggccc      900 ccgccggaag gggccttcgt gggctttgtg ctttcccgca aggagcccat gtgggccgat      960
cttctggccc tggccgccgc caggggggc cgggtccacc gggcccccga gccttataaa     1020
gccctcaggg acctgaagga ggcgcggggg cttctcgcca agacctgag cgttctggcc     1080 ctgagggaag gccttggcct cccgcccggc gacgacccca tgnnnctcgc ctacctcctg     1140
gacccttcca acaccacccc cgaggggtg gcccggcgct acggcgggga gtggacggag     1200
gaggcggggg agcggccgc cctttccgag aggctcttcg ccaacctgtg ggggaggctt     1260 gaggggagg agaggctcct ttggctttac cggaggtgg agaggcccct ttccgctgtc     1320
ctggcccaca tggaggccac gggggtgcgc ctggacgtgg cctatctcag ggccttgtcc     1380
```

```
ctggaggtgg ccgaggagat cgcccgcctc gaggccgagg tcttccgcct ggccggccac    1440
cccttcaacc tcaactcccg ggaccagctg gaaagggtcc tctttgacga gctagggctt    1500
cccgccatcg gcaagacgnn naagaccggc aagcgctcca ccagcgccgc cgtcctggag    1560
gccctccgcg aggcccaccc catcgtggag aagatcctgc agtaccggga gctcaccaag    1620
ctgaagagca cctacattga ccccttgccg gacctcatcc accccaggac gggccgcctc    1680
cacacccgct tcaaccagac ggccacggcc acgggcaggc taagtagctc cgatcccaac    1740
ctccagaaca tccccgtccg caccccgctt gggcagagga tccgccgggc cttcatcgcc    1800
gaggaggggt ggctattggt ggccctggac tatagccaga tagagctcag ggtgctggcc    1860
cacctctccg gcgacgagaa cctgatccgg gtcttccagg aggggcggga catccacacg    1920
gagaccgcca gctggatgtt cggcgtcccc cgggaggccg tggacccccc tgatgcgccg    1980
gcggccaaga ccatcaactt cggggtcctc tacggcatgt cggcccaccg cctctcccag    2040
gagctagcca tcccttacga ggaggcccag gccttcattg agcgctactt tcagagcttc    2100
cccaaggtgc gggcctggat tgagaagacc ctggaggagg caggaggcg ggggtacgtg    2160 gagaccctct tcggccgccg ccgctacgtg ccagacctan nngcccgggt gaagagcgtg    2220
cgggaggcgg ccgagcgcat ggccnnnaac atgcccgtcc agggcaccgc cgccgacctc    2280
atgaagctgg ctatggtgaa gctcttcccc aggctggagg aaatgggggc caggatgctc    2340
cttcaggtcc acgacgagct ggtcctcgag gccccaaaag agagggcgga ggccgtggcc    2400
cggctggcca aggaggtcat ggaggggggtg tatccccctgg ccgtgccccct ggaggtggag    2460 gtggggatag gggaggactg gctctccgcc aaggagtaa                            2499
```

<210> SEQ ID NO 20
<211> LENGTH: 832
<212> TYPE: PRT
<213> ORGANISM: Thermus aquaticus
<220> FEATURE:
<221> NAME/KEY: MISC_FEATURE
<222> LOCATION: (1)..(832)
<223> OTHER INFORMATION: X can be any amino acid except for Q or E

<400> SEQUENCE: 20

```
Met Arg Gly Met Leu Pro Leu Phe Glu Pro Lys Gly Arg Val Leu Leu
1               5                   10                  15

Val Asp Gly His His Leu Ala Tyr Arg Thr Phe His Ala Leu Lys Gly
                20                  25                  30

Leu Thr Thr Ser Arg Gly Glu Pro Val Gln Ala Val Tyr Gly Phe Ala
        35                  40                  45

Lys Ser Leu Leu Lys Ala Leu Lys Glu Asp Gly Asp Ala Val Ile Val
    50                  55                  60

Val Phe Asp Ala Lys Ala Pro Ser Phe Arg His Glu Ala Tyr Gly Gly
65                  70                  75                  80

Tyr Lys Ala Gly Arg Ala Pro Thr Pro Glu Asp Phe Pro Arg Gln Leu
                85                  90                  95

Ala Leu Ile Lys Glu Leu Val Asp Leu Leu Gly Leu Ala Arg Leu Glu
            100                 105                 110

Val Pro Gly Tyr Glu Ala Asp Asp Val Leu Ala Ser Leu Ala Lys Lys
        115                 120                 125

Ala Glu Lys Glu Gly Tyr Glu Val Arg Ile Leu Thr Ala Asp Lys Asp
    130                 135                 140

Leu Tyr Gln Leu Leu Ser Asp Arg Ile His Val Leu His Pro Glu Gly
```

```
            145                 150                 155                 160
Tyr Leu Ile Thr Pro Ala Trp Leu Trp Glu Lys Tyr Gly Leu Arg Pro
                    165                 170                 175
Asp Gln Trp Ala Asp Tyr Arg Ala Leu Thr Gly Asp Glu Ser Asp Asn
                    180                 185                 190
Leu Pro Gly Val Lys Gly Ile Gly Glu Lys Thr Ala Arg Lys Leu Leu
                    195                 200                 205
Glu Glu Trp Gly Ser Leu Glu Ala Leu Lys Asn Leu Asp Arg Leu
                    210                 215                 220
Lys Pro Ala Ile Arg Glu Lys Ile Leu Ala His Met Asp Asp Leu Lys
225                 230                 235                 240
Leu Ser Trp Asp Leu Ala Lys Val Arg Thr Asp Leu Pro Leu Glu Val
                    245                 250                 255
Asp Phe Ala Lys Arg Arg Glu Pro Asp Arg Glu Arg Leu Arg Ala Phe
                    260                 265                 270
Leu Glu Arg Leu Glu Phe Gly Ser Leu Leu His Glu Phe Gly Leu Leu
                    275                 280                 285
Glu Ser Pro Lys Ala Leu Glu Glu Ala Pro Trp Pro Pro Glu Gly
                    290                 295                 300
Ala Phe Val Gly Phe Val Leu Ser Arg Lys Glu Pro Met Trp Ala Asp
305                 310                 315                 320
Leu Leu Ala Leu Ala Ala Ala Arg Gly Gly Arg Val His Arg Ala Pro
                    325                 330                 335
Glu Pro Tyr Lys Ala Leu Arg Asp Leu Lys Glu Ala Arg Gly Leu Leu
                    340                 345                 350
Ala Lys Asp Leu Ser Val Leu Ala Leu Arg Glu Gly Leu Gly Leu Pro
                    355                 360                 365
Pro Gly Asp Asp Pro Met Leu Leu Ala Tyr Leu Leu Asp Pro Ser Asn
                    370                 375                 380
Thr Thr Pro Glu Gly Val Ala Arg Arg Tyr Gly Gly Glu Trp Thr Glu
385                 390                 395                 400
Glu Ala Gly Glu Arg Ala Ala Leu Ser Glu Arg Leu Phe Ala Asn Leu
                    405                 410                 415
Trp Gly Arg Leu Glu Gly Glu Glu Arg Leu Leu Trp Leu Tyr Arg Glu
                    420                 425                 430
Val Glu Arg Pro Leu Ser Ala Val Leu Ala His Met Glu Ala Thr Gly
                    435                 440                 445
Val Arg Leu Asp Val Ala Tyr Leu Arg Ala Leu Ser Leu Glu Val Ala
                    450                 455                 460
Glu Glu Ile Ala Arg Leu Glu Ala Glu Val Phe Arg Leu Ala Gly His
465                 470                 475                 480
Pro Phe Asn Leu Asn Ser Arg Asp Gln Leu Glu Arg Val Leu Phe Asp
                    485                 490                 495
Glu Leu Gly Leu Pro Ala Ile Gly Lys Thr Xaa Lys Thr Gly Lys Arg
                    500                 505                 510
Ser Thr Ser Ala Ala Val Leu Glu Ala Leu Arg Glu Ala His Pro Ile
                    515                 520                 525
Val Glu Lys Ile Leu Gln Tyr Arg Glu Leu Thr Lys Leu Lys Ser Thr
                    530                 535                 540
Tyr Ile Asp Pro Leu Pro Asp Leu Ile His Pro Arg Thr Gly Arg Leu
545                 550                 555                 560
His Thr Arg Phe Asn Gln Thr Ala Thr Ala Thr Gly Arg Leu Ser Ser
                    565                 570                 575
```

Ser Asp Pro Asn Leu Gln Asn Ile Pro Val Arg Thr Pro Leu Gly Gln
            580                 585                 590

Arg Ile Arg Arg Ala Phe Ile Ala Glu Glu Gly Trp Leu Val Ala
            595                 600                 605

Leu Asp Tyr Ser Gln Ile Glu Leu Arg Val Leu Ala His Leu Ser Gly
            610                 615                 620

Asp Glu Asn Leu Ile Arg Val Phe Gln Glu Gly Arg Asp Ile His Thr
625                 630                 635                 640

Glu Thr Ala Ser Trp Met Phe Gly Val Pro Arg Glu Ala Val Asp Pro
                645                 650                 655

Leu Met Arg Ala Ala Lys Thr Ile Asn Phe Gly Val Leu Tyr Gly
            660                 665                 670

Met Ser Ala His Arg Leu Ser Gln Glu Leu Ala Ile Pro Tyr Glu Glu
            675                 680                 685

Ala Gln Ala Phe Ile Glu Arg Tyr Phe Gln Ser Phe Pro Lys Val Arg
            690                 695                 700

Ala Trp Ile Glu Lys Thr Leu Glu Glu Gly Arg Arg Arg Gly Tyr Val
705                 710                 715                 720

Glu Thr Leu Phe Gly Arg Arg Tyr Val Pro Asp Leu Glu Ala Arg
                725                 730                 735

Val Lys Ser Val Arg Glu Ala Ala Glu Arg Met Ala Phe Asn Met Pro
            740                 745                 750

Val Gln Gly Thr Ala Ala Asp Leu Met Lys Leu Ala Met Val Lys Leu
            755                 760                 765

Phe Pro Arg Leu Glu Glu Met Gly Ala Arg Met Leu Leu Gln Val His
            770                 775                 780

Asp Glu Leu Val Leu Glu Ala Pro Lys Glu Arg Ala Glu Ala Val Ala
785                 790                 795                 800

Arg Leu Ala Lys Glu Val Met Glu Gly Val Tyr Pro Leu Ala Val Pro
                805                 810                 815

Leu Glu Val Glu Val Gly Ile Gly Glu Asp Trp Leu Ser Ala Lys Glu
            820                 825                 830

<210> SEQ ID NO 21
<211> LENGTH: 2499
<212> TYPE: DNA
<213> ORGANISM: Thermus aquaticus
<220> FEATURE:
<221> NAME/KEY: misc_feature
<222> LOCATION: (1)..(2499)
<223> OTHER INFORMATION: nnn can encode for any amino acid except for
      Q or E

<400> SEQUENCE: 21

| | | |
|---|---|---|
| atgcgtggca tgcttcctct ttttgagccc aagggccggg tcctcctggt ggacggccac | 60 |
| cacctggcct accgcacctt ccacgccctg aagggcctca ccaccagccg gggggagccg | 120 |
| gtgcaggcgg tctacggctt cgccaagagc ctcctcaagg ccctcaagga ggacggggac | 180 |
| gcggtgatcg tggtctttga cgccaaggcc cctccttcc gccacgaggc ctacgggggg | 240 |
| tacaaggcgg gccgggcccc cacgccggag ctttccccc ggcaactcgc cctcatcaag | 300 |
| gagctggtgg acctcctggg gctggcgcgc tcgaggtcc cgggctacga ggcggacgac | 360 |
| gtcctggcca gctggccaa gaaggcggaa aaggagggct acgaggtccg catcctcacc | 420 |
| gccgacaaag acctttacca gctcctttcc gaccgcatcc acgtcctcca ccccgagggg | 480 |
| tacctcatca ccccggcctg gctttgggaa agtacggcc tgaggcccga ccagtgggcc | 540 |

```
gactaccggg ccctgaccgg ggacgagtcc gacaaccttc ccggggtcaa gggcatcggg      600
gagaagacgg cgaggaagct tctggaggag tgggggagcc tggaagccct cctcaagaac      660
ctggaccggc tgaagcccgc catccgggag aagatcctgg cccacatgga cgatctgaag      720
ctctcctggg acctggccaa ggtgcgcacc gacctgcccc tggaggtgga cttcgccaaa      780
aggcgggagc ccgaccggga gaggcttagg gcctttctgg agaggcttga gtttggcagc      840
ctcctccacg agttcggcct tctggaaagc cccaaggccc tggaggaggc ccctggccc       900 ccgccggaag gggccttcgt gggctttgtg ctttcccgca aggagcccat gtgggccgat      960
cttctggccc tggccgccgc cagggggggc cgggtccacc gggcccccga gccttataaa     1020
gccctcaggg acctgaagga ggcgcggggg cttctcgcca agacctgag cgttctggcc      1080 ctgagggaag gccttggcct cccgccggc gacgacccca tgctcctcgc ctacctcctg      1140
gacccttcca acaccacccc cgagggggtg gcccggcgct acggcgggga gtggacggag     1200
gaggcggggg agcgggccgc cctttccgag aggctcttcg ccaacctgtg ggggaggctt     1260 gaggggagg agaggctcct ttggctttac cgggaggtgg agaggcccct ttccgctgtc      1320
ctggcccaca tggaggccac ggggggtgcgc ctggacgtgg cctatctcag ggccttgtcc     1380
ctggaggtgg ccgaggagat cgcccgcctc gaggccgagg tcttccgcct ggccggccac     1440
cccttcaacc tcaactcccg ggaccagctg gaaagggtcc tctttgacga gctagggctt     1500
cccgccatcg gcaagacgnn naagaccggc aagcgctcca ccagcgccgc cgtcctggag     1560
gccctccgcg aggcccaccc catcgtggag aagatcctgc agtaccggga gctcaccaag     1620
ctgaagagca cctacattga cccccttgccg gacctcatcc accccaggac gggccgcctc     1680
cacacccgct tcaaccagac ggccacggcc acgggcaggc taagtagctc cgatcccaac     1740
ctccagaaca tccccgtccg cacccccgctt gggcagagga tccgccgggc cttcatcgcc     1800 gaggagggt ggctattggt ggccctggac tatagccaga tagagctcag ggtgctggcc     1860
cacctctccg gcgacgagaa cctgatccgg gtcttccagg aggggcggga catccacacg     1920
gagaccgcca gctggatgtt cggcgtcccc cgggaggccg tggacccct gatgcgccgg     1980 gcggccaaga ccatcaactt cggggtcctc tacggcatgt cggcccaccg cctctcccag     2040
gagctagcca tcccttacga ggaggccag gccttcattg agcgctactt tcagagcttc     2100
cccaaggtgc gggcctggat tgagaagacc ctggaggagg caggaggcg gggtacgtg      2160 gagaccctct tcggccgccg ccgctacgtg ccagacctag aggcccgggt gaagagcgtg     2220
cgggaggcgg ccgagcgcat ggccttcaac atgcccgtcc agggcaccgc cgccgacctc     2280
atgaagctgg ctatggtgaa gctcttcccc aggctggagg aaatgggggc caggatgctc     2340
cttcaggtcc acgacgagct ggtcctcgag gccccaaaag agagggcgga ggccgtggcc     2400
cggctggcca aggaggtcat ggaggggggtg tatcccctgg ccgtgccct ggaggtggag     2460 gtggggatag gggaggactg gctctccgcc aaggagtaa                           2499
```

<210> SEQ ID NO 22
<211> LENGTH: 832
<212> TYPE: PRT
<213> ORGANISM: Thermus aquaticus

<400> SEQUENCE: 22

```
Met Arg Gly Met Leu Pro Leu Phe Glu Pro Lys Gly Arg Val Leu Leu
1               5                   10                  15

Val Asp Gly His His Leu Ala Tyr Arg Thr Phe His Ala Leu Lys Gly
```

```
            20                  25                  30
Leu Thr Thr Ser Arg Gly Glu Pro Val Gln Ala Val Tyr Gly Phe Ala
            35                  40                  45
Lys Ser Leu Leu Lys Ala Leu Lys Glu Asp Gly Asp Ala Val Ile Val
        50                  55                  60
Val Phe Asp Ala Lys Ala Pro Ser Phe Arg His Glu Ala Tyr Gly Gly
65                  70                  75                  80
Tyr Lys Ala Gly Arg Ala Pro Thr Pro Glu Asp Phe Pro Arg Gln Leu
                85                  90                  95
Ala Leu Ile Lys Glu Leu Val Asp Leu Gly Leu Ala Arg Leu Glu
                100                 105                 110
Val Pro Gly Tyr Glu Ala Asp Asp Val Leu Ala Ser Leu Ala Lys Lys
            115                 120                 125
Ala Glu Lys Glu Gly Tyr Glu Val Arg Ile Leu Thr Ala Asp Lys Asp
            130                 135                 140
Leu Tyr Gln Leu Leu Ser Asp Arg Ile His Val Leu His Pro Glu Gly
145                 150                 155                 160
Tyr Leu Ile Thr Pro Ala Trp Leu Trp Glu Lys Tyr Gly Leu Arg Pro
                165                 170                 175
Asp Gln Trp Ala Asp Tyr Arg Ala Leu Thr Gly Asp Glu Ser Asp Asn
                180                 185                 190
Leu Pro Gly Val Lys Gly Ile Gly Glu Lys Thr Ala Arg Lys Leu Leu
            195                 200                 205
Glu Glu Trp Gly Ser Leu Glu Ala Leu Leu Lys Asn Leu Asp Arg Leu
            210                 215                 220
Lys Pro Ala Ile Arg Glu Lys Ile Leu Ala His Met Asp Asp Leu Lys
225                 230                 235                 240
Leu Ser Trp Asp Leu Ala Lys Val Arg Thr Asp Leu Pro Leu Glu Val
                245                 250                 255
Asp Phe Ala Lys Arg Arg Glu Pro Asp Arg Glu Arg Leu Arg Ala Phe
                260                 265                 270
Leu Glu Arg Leu Glu Phe Gly Ser Leu Leu His Glu Phe Gly Leu Leu
            275                 280                 285
Glu Ser Pro Lys Ala Leu Glu Glu Ala Pro Trp Pro Pro Pro Glu Gly
            290                 295                 300
Ala Phe Val Gly Phe Val Leu Ser Arg Lys Glu Pro Met Trp Ala Asp
305                 310                 315                 320
Leu Leu Ala Leu Ala Ala Ala Arg Gly Gly Arg Val His Arg Ala Pro
                325                 330                 335
Glu Pro Tyr Lys Ala Leu Arg Asp Leu Lys Glu Ala Arg Gly Leu Leu
                340                 345                 350
Ala Lys Asp Leu Ser Val Leu Ala Leu Arg Glu Gly Leu Gly Leu Pro
            355                 360                 365
Pro Gly Asp Asp Pro Met Leu Leu Ala Tyr Leu Leu Asp Pro Ser Asn
            370                 375                 380
Thr Thr Pro Glu Gly Val Ala Arg Arg Tyr Gly Gly Glu Trp Thr Glu
385                 390                 395                 400
Glu Ala Gly Glu Arg Ala Ala Leu Ser Glu Arg Leu Phe Ala Asn Leu
                405                 410                 415
Trp Gly Arg Leu Glu Gly Glu Glu Arg Leu Leu Trp Leu Tyr Arg Glu
                420                 425                 430
Val Glu Arg Pro Leu Ser Ala Val Leu Ala His Met Glu Ala Thr Gly
            435                 440                 445
```

Val Arg Leu Asp Val Ala Tyr Leu Arg Ala Leu Ser Leu Glu Val Ala
    450                 455                 460

Glu Glu Ile Ala Arg Leu Glu Ala Glu Val Phe Arg Leu Ala Gly His
465                 470                 475                 480

Pro Phe Asn Leu Asn Ser Arg Asp Gln Leu Glu Arg Val Leu Phe Asp
                485                 490                 495

Glu Leu Gly Leu Pro Ala Ile Gly Lys Thr Lys Thr Gly Lys Arg
            500                 505                 510

Ser Thr Ser Ala Ala Val Leu Glu Ala Leu Arg Glu Ala His Pro Ile
        515                 520                 525

Val Glu Lys Ile Leu Gln Tyr Arg Glu Leu Thr Lys Leu Lys Ser Thr
    530                 535                 540

Tyr Ile Asp Pro Leu Pro Asp Leu Ile His Pro Arg Thr Gly Arg Leu
545                 550                 555                 560

His Thr Arg Phe Asn Gln Thr Ala Thr Ala Thr Gly Arg Leu Ser Ser
                565                 570                 575

Ser Asp Pro Asn Leu Gln Asn Ile Pro Val Arg Thr Pro Leu Gly Gln
            580                 585                 590

Arg Ile Arg Arg Ala Phe Ile Ala Glu Glu Gly Trp Leu Leu Val Ala
    595                 600                 605

Leu Asp Tyr Ser Gln Ile Glu Leu Arg Val Leu Ala His Leu Ser Gly
    610                 615                 620

Asp Glu Asn Leu Ile Arg Val Phe Gln Glu Gly Arg Asp Ile His Thr
625                 630                 635                 640

Glu Thr Ala Ser Trp Met Phe Gly Val Pro Arg Glu Ala Val Asp Pro
                645                 650                 655

Leu Met Arg Arg Ala Ala Lys Thr Ile Asn Phe Gly Val Leu Tyr Gly
            660                 665                 670

Met Ser Ala His Arg Leu Ser Gln Glu Leu Ala Ile Pro Tyr Glu Glu
        675                 680                 685

Ala Gln Ala Phe Ile Glu Arg Tyr Phe Gln Ser Phe Pro Lys Val Arg
    690                 695                 700

Ala Trp Ile Glu Lys Thr Leu Glu Glu Gly Arg Arg Arg Gly Tyr Val
705                 710                 715                 720

Glu Thr Leu Phe Gly Arg Arg Arg Tyr Val Pro Asp Leu Glu Ala Arg
                725                 730                 735

Val Lys Ser Val Arg Glu Ala Ala Glu Arg Met Ala Phe Asn Met Pro
            740                 745                 750

Val Gln Gly Thr Ala Ala Asp Leu Met Lys Leu Ala Met Val Lys Leu
        755                 760                 765

Phe Pro Arg Leu Glu Glu Met Gly Ala Arg Met Leu Leu Gln Val His
    770                 775                 780

Asp Glu Leu Val Leu Glu Ala Pro Lys Glu Arg Ala Glu Ala Val Ala
785                 790                 795                 800

Arg Leu Ala Lys Glu Val Met Glu Gly Val Tyr Pro Leu Ala Val Pro
                805                 810                 815

Leu Glu Val Glu Val Gly Ile Gly Glu Asp Trp Leu Ser Ala Lys Glu
            820                 825                 830

<210> SEQ ID NO 23
<211> LENGTH: 2499
<212> TYPE: DNA
<213> ORGANISM: Thermus aquaticus

```
<400> SEQUENCE: 23
atgcgtggca tgcttcctct ttttgagccc aagggccggg tcctcctggt ggacggccac      60
cacctggcct accgcaccttc ccacgccctg aagggcctca ccaccagccg ggggagccg     120 gtgcaggcgg tctacggctt cgccaagagc ctcctcaagg ccctcaagga ggacggggac    180
gcggtgatcg tggtctttga cgccaaggcc ccctccttcc gccacgaggc ctacgggggg    240
tacaaggcgg gccgggcccc cacgccgagc gactttcccc ggcaactcgc cctcatcaag    300
gagctggtgg acctcctggg gctggcgcgc ctcgaggtcc cgggctacga ggcggacgac    360
gtcctggcca gcctggccaa gaaggcggaa aaggagggct acgaggtccg catcctcacc    420
gccgacaaag acctttacca gctcctttcc gaccgcatcc acgtcctcca ccccgagggg    480
tacctcatca ccccggcctg gctttgggaa aagtacggcc tgaggcccga ccagtgggcc    540
gactaccggg ccctgaccgg ggacgagtcc gacaacctcc ccggggtcaa gggcatcggg    600
gagaagacgg cgaggaagct tctggaggag tgggggagcc tggaagcccct cctcaagaac    660 ctggaccggc tgaagcccgc catccgggag aagatcctgg cccacatgga cgatctgaag    720
ctctcctggg acctggccaa ggtgcgcacc gacctgcccc tggaggtgga cttcgccaaa    780
aggcgggagc ccgaccggga gaggcttagg gcctttctgg agaggcttga gtttggcagc    840
ctcctccacg agttcggcct tctgaaaagc cccaaggccc tggaggaggc ccctggccc     900 ccgccggaag gggccttcgt gggctttgtg ctttcccgca aggagcccat gtgggccgat    960
cttctggccc tggccgccgc cagggggggc cgggtccacc gggcccccga gccttataaa   1020
gccctcaggg acctgaagga ggcgcggggg cttctcgcca agacctgag cgttctggcc    1080 ctgagggaag gccttggcct cccgcccggc gacgaccca tgctcctcgc ctacctcctg    1140
gacccttcca acaccacccc cgaggggtg gcccggcgct acggcgggga gtggacggag    1200
gaggcggggg agcgggccgc cctttccgag aggctcttcg ccaacctgtg ggggaggctt    1260 gaggggggagg agaggctcct ttggctttac cgggaggtgg agaggcccct ttccgctgtc    1320
ctggcccaca tggaggccac gggggtgcgc ctggacgtgg cctatctcag ggccttgtcc    1380
ctggaggtgg ccgaggagat cgcccgcctc gaggccgagg tcttccgcct ggccggccac    1440
cccttcaacc tcaactcccg ggaccagctg gaaagggtcc tctttgacga gctagggctt    1500
cccgccatcg gcaagacgaa gaagaccggc aagcgctcca ccagcgccgc cgtcctggag    1560
gccctccgcg aggcccaccc catcgtggag aagatcctgc agtaccggga gctcaccaag    1620
ctgaagagca cctacattga ccccttgccg gacctcatcc accccaggac gggccgcctc    1680
cacacccgct tcaaccagac ggccacggcc acgggcaggc taagtagctc cgatcccaac    1740
ctccagaaca tccccgtccg caccccgctt gggcagagga tccgccgggc cttcatcgcc    1800
gaggaggggt ggctattggt ggccctggac tatagccaga tagagctcag ggtgctggcc    1860
cacctctccg gcgacgagaa cctgatccgg gtcttccagg aggggcggga catccacacg    1920
gagaccgcca gctggatgtt cggcgtcccc cgggaggcct ggaccccct gatgcgccgg    1980 gcggccaaga ccatcaactt cggggtcctc tacggcatgt cggcccaccg cctctcccag    2040
gagctagcca tcccttacga ggaggccag gccttcattg agcgctactt tcagagcttc    2100
cccaaggtgc gggcctggat tgagaagacc ctggaggagg caggaggcg ggggtacgtg    2160 gagacccctct tcggccgccg ccgctacgtg ccagacctag aggcccgggt gaagagcgtg    2220 cgggaggcg ccgagcgcat ggccttcaac atgcccgtcc agggcaccgc cgccgacctc    2280
atgaagctgg ctatggtgaa gctcttcccc aggctggagg aaatgggggc caggatgctc    2340
```

-continued

```
cttcaggtcc acgacgagct ggtcctcgag gccccaaaag agagggcgga ggccgtggcc    2400
cggctggcca aggaggtcat ggaggggtg tatcccctgg ccgtgcccct ggaggtggag     2460
gtggggatag ggaggactg gctctccgcc aaggagtaa                            2499
```

<210> SEQ ID NO 24
<211> LENGTH: 832
<212> TYPE: PRT
<213> ORGANISM: Thermus aquaticus

<400> SEQUENCE: 24

```
Met Arg Gly Met Leu Pro Leu Phe Glu Pro Lys Gly Arg Val Leu Leu
1               5                   10                  15

Val Asp Gly His His Leu Ala Tyr Arg Thr Phe His Ala Leu Lys Gly
                20                  25                  30

Leu Thr Thr Ser Arg Gly Glu Pro Val Gln Ala Val Tyr Gly Phe Ala
            35                  40                  45

Lys Ser Leu Leu Lys Ala Leu Lys Glu Asp Gly Asp Ala Val Ile Val
    50                  55                  60

Val Phe Asp Ala Lys Ala Pro Ser Phe Arg His Glu Ala Tyr Gly Gly
65                  70                  75                  80

Tyr Lys Ala Gly Arg Ala Pro Thr Pro Glu Asp Phe Pro Arg Gln Leu
                85                  90                  95

Ala Leu Ile Lys Glu Leu Val Asp Leu Leu Gly Leu Ala Arg Leu Glu
            100                 105                 110

Val Pro Gly Tyr Glu Ala Asp Asp Val Leu Ala Ser Leu Ala Lys Lys
        115                 120                 125

Ala Glu Lys Glu Gly Tyr Glu Val Arg Ile Leu Thr Ala Asp Lys Asp
    130                 135                 140

Leu Tyr Gln Leu Leu Ser Asp Arg Ile His Val Leu His Pro Glu Gly
145                 150                 155                 160

Tyr Leu Ile Thr Pro Ala Trp Leu Trp Glu Lys Tyr Gly Leu Arg Pro
                165                 170                 175

Asp Gln Trp Ala Asp Tyr Arg Ala Leu Thr Gly Asp Glu Ser Asp Asn
            180                 185                 190

Leu Pro Gly Val Lys Gly Ile Gly Glu Lys Thr Ala Arg Lys Leu Leu
        195                 200                 205

Glu Glu Trp Gly Ser Leu Glu Ala Leu Leu Lys Asn Leu Asp Arg Leu
    210                 215                 220

Lys Pro Ala Ile Arg Glu Lys Ile Leu Ala His Met Asp Asp Leu Lys
225                 230                 235                 240

Leu Ser Trp Asp Met Ala Lys Val Arg Thr Asp Leu Pro Leu Glu Val
                245                 250                 255

Asp Phe Ala Lys Arg Arg Glu Pro Asp Arg Glu Arg Leu Arg Ala Phe
            260                 265                 270

Leu Glu Arg Leu Glu Phe Gly Ser Leu Leu His Glu Phe Gly Leu Leu
        275                 280                 285

Glu Ser Pro Lys Ala Leu Glu Glu Ala Pro Trp Pro Pro Pro Glu Gly
    290                 295                 300

Ala Phe Val Gly Phe Val Leu Ser Arg Lys Glu Pro Met Trp Ala Asp
305                 310                 315                 320

Leu Leu Ala Leu Ala Ala Ala Arg Gly Gly Arg Val His Arg Ala Pro
                325                 330                 335

Glu Pro Tyr Lys Ala Leu Arg Asp Leu Lys Glu Ala Arg Gly Leu Leu
```

```
              340                 345                 350
Ala Lys Asp Leu Ser Val Leu Ala Leu Arg Glu Gly Leu Gly Leu Pro
            355                 360                 365

Pro Gly Asp Asp Pro Met Leu Leu Ala Tyr Leu Leu Asp Pro Ser Asn
        370                 375                 380

Thr Thr Pro Glu Gly Val Ala Arg Arg Tyr Gly Gly Glu Trp Thr Glu
385                 390                 395                 400

Glu Ala Gly Glu Arg Ala Ala Leu Ser Glu Arg Leu Phe Ala Asn Leu
                405                 410                 415

Trp Gly Arg Leu Glu Gly Glu Arg Leu Leu Trp Leu Tyr Arg Glu
            420                 425                 430

Val Glu Arg Pro Leu Ser Ala Val Leu Ala His Met Glu Ala Thr Gly
            435                 440                 445

Val Arg Leu Asp Val Ala Tyr Leu Arg Ala Leu Ser Leu Glu Val Ala
        450                 455                 460

Glu Glu Ile Ala Arg Leu Glu Ala Glu Val Phe Arg Leu Ala Gly His
465                 470                 475                 480

Pro Phe Asn Leu Asn Ser Arg Asp Gln Leu Glu Arg Val Leu Phe Asp
                485                 490                 495

Glu Leu Gly Leu Pro Ala Ile Gly Lys Thr Lys Thr Gly Lys Arg
            500                 505                 510

Ser Thr Ser Ala Ala Val Leu Glu Ala Leu Arg Glu Ala His Pro Ile
        515                 520                 525

Val Glu Lys Ile Leu Gln Tyr Arg Glu Leu Thr Lys Leu Lys Ser Thr
    530                 535                 540

Tyr Ile Asp Pro Leu Pro Asp Leu Ile His Pro Arg Thr Gly Arg Leu
545                 550                 555                 560

His Thr Arg Phe Asn Gln Thr Ala Thr Ala Thr Gly Arg Leu Ser Ser
                565                 570                 575

Ser Asp Pro Asn Leu Gln Asn Ile Pro Val Arg Thr Pro Leu Gly Gln
            580                 585                 590

Arg Ile Arg Arg Ala Phe Ile Ala Glu Glu Gly Trp Leu Leu Val Ala
        595                 600                 605

Leu Asp Tyr Ser Gln Ile Glu Leu Arg Val Leu Ala His Leu Ser Gly
    610                 615                 620

Asp Glu Asn Leu Ile Arg Val Phe Gln Glu Gly Arg Asp Ile His Thr
625                 630                 635                 640

Glu Thr Ala Ser Trp Met Phe Gly Val Pro Arg Glu Ala Val Asp Pro
                645                 650                 655

Leu Met Arg Arg Ala Ala Lys Thr Ile Asn Phe Gly Val Leu Tyr Gly
            660                 665                 670

Met Ser Ala His Arg Leu Ser Gln Glu Leu Ala Ile Pro Tyr Glu Glu
        675                 680                 685

Ala Gln Ala Phe Ile Glu Arg Tyr Phe Gln Ser Phe Pro Lys Val Arg
    690                 695                 700

Ala Trp Ile Glu Lys Thr Leu Glu Glu Gly Arg Arg Arg Gly Tyr Val
705                 710                 715                 720

Glu Thr Leu Phe Gly Arg Arg Arg Tyr Val Pro Asp Leu Glu Ala Arg
                725                 730                 735

Val Lys Ser Val Arg Glu Ala Glu Arg Met Ala Ile Asn Met Pro
            740                 745                 750

Val Gln Gly Thr Ala Ala Asp Leu Met Lys Leu Ala Met Val Lys Leu
        755                 760                 765
```

```
        Phe Pro Arg Leu Glu Glu Met Gly Ala Arg Met Leu Leu Gln Val His
            770                 775                 780

Asp Glu Leu Val Leu Glu Ala Pro Lys Glu Arg Ala Glu Ala Val Ala
        785                 790                 795                 800

Arg Leu Ala Lys Glu Val Met Glu Gly Val Tyr Pro Leu Ala Val Pro
                        805                 810                 815

Leu Glu Val Glu Val Gly Ile Gly Glu Asp Trp Leu Ser Ala Lys Glu
                    820                 825                 830

<210> SEQ ID NO 25
<211> LENGTH: 2499
<212> TYPE: DNA
<213> ORGANISM: Thermus aquaticus

<400> SEQUENCE: 25
```

| | | |
|---|---|---|
| atgcgtggca tgcttcctct ttttgagccc aagggccggg tcctcctggt ggacggccac | 60 |
| cacctggcct accgcacctt ccacgccctg aagggcctca ccaccagccg ggggagccg | 120 |
| gtgcaggcgg tctacggctt cgccaagagc ctcctcaagg ccctcaagga ggacggggac | 180 |
| gcggtgatcg tggtctttga cgccaaggcc cctccttcc gccacgaggc ctacggggg | 240 |
| tacaaggcgg ccgggcccc cacgccggag gactttcccc ggcaactcgc cctcatcaag | 300 |
| gagctggtgg acctcctggg gctggcgcgc ctcgaggtcc cgggctacga ggcggacgac | 360 |
| gtcctggcca gctggccaa gaaggcggaa aaggagggct acgaggtccg catcctcacc | 420 |
| gccgacaaag acctttacca gctcctttcc gaccgcatcc acgtcctcca ccccgagggg | 480 |
| tacctcatca ccccggcctg gctttgggaa agtacggcc tgaggcccga ccagtgggcc | 540 |
| gactaccggg ccctgaccgg ggacgagtcc gacaaccttc ccggggtcaa gggcatcggg | 600 |
| gagaagacgg cgaggaagct tctggaggag tggggagcc tggaagccct cctcaagaac | 660 |
| ctggaccggc tgaagcccgc catccggag aagatcctgg cccacatgga cgatctgaag | 720 |
| ctctcctggg acatggccaa ggtgcgcacc gacctgcccc tggaggtgga cttcgccaaa | 780 |
| aggcgggagc ccgaccggga gaggcttagg gcctttctgg agaggcttga gtttggcagc | 840 |
| ctcctccacg agttcggcct tctggaaagc cccaaggccc tggaggaggc ccctggcc | 900 |
| ccgccggaag ggcccttcgt gggctttgtg cttccccgca aggagcccat gtgggccgat | 960 |
| cttctggccc tggccgccgc cagggggggc cgggtccacc gggcccccga gccttataaa | 1020 |
| gccctcaggg acctgaagga ggcgcgggg cttctcgcca agacctgag cgttctggcc | 1080 |
| ctgagggaag gccttggcct cccgcccggc gacgacccca tgctcctcgc ctacctcctg | 1140 |
| gacccttcca acaccacccc cgaggggtg gcccggcgct acggcgggga gtggacggag | 1200 |
| gaggcggggg agcgggccgc cctttccgag aggctcttcg ccaacctgtg ggggaggctt | 1260 |
| gaggggagg agaggctcct ttggctttac cgggaggtgg agaggcccct ttccgctgtc | 1320 |
| ctggcccaca tggaggccac gggggtgcgc ctggacgtgg cctatctcag ggccttgtcc | 1380 |
| ctggaggtgg ccgaggagat cgcccgcctc gaggccgagg tcttccgcct ggccggccac | 1440 |
| cccttcaacc tcaactcccg ggaccagctg gaaagggtcc tctttgacga gctagggctt | 1500 |
| cccgccatcg gcaagacgaa gaagaccggc aagcgctcca ccagcgccgc cgtcctggag | 1560 |
| gcctccgcg aggcccaccc catcgtggag aagatcctgc agtaccggga gctcaccaag | 1620 |
| ctgaagagca cctacattga ccccttgccg gacctcatcc accccaggac gggccgcctc | 1680 |
| cacacccgct tcaaccagac ggccacggcc acgggcaggc taagtagctc cgatcccaac | 1740 |

```
ctccagaaca tccccgtccg caccccgctt gggcagagga tccgccgggc cttcatcgcc    1800
gaggaggggt ggctattggt ggccctggac tatagccaga tagagctcag ggtgctggcc    1860
cacctctccg gcgacgagaa cctgatccgg gtcttccagg aggggcggga catccacacg    1920
gagaccgcca gctggatgtt cggcgtcccc cgggaggccg tggacccct gatgcgccgg     1980 gcggccaaga ccatcaactt cggggtcctc tacggcatgt cggcccaccg cctctcccag    2040
gagctagcca tcccttacga ggaggcccag gccttcattg agcgctactt tcagagcttc    2100
cccaaggtgc gggcctggat tgagaagacc ctggaggagg caggaggcg ggggtacgtg     2160 gagaccctct tcggccgccg ccgctacgtg ccagacctag aggcccgggt gaagagcgtg    2220
cgggaggcgg ccgagcgcat ggccatcaac atgcccgtcc agggcaccgc cgccgacctc    2280
atgaagctgg ctatggtgaa gctcttcccc aggctggagg aaatgggggc caggatgctc    2340
cttcaggtcc acgacgagct ggtcctcgag gccccaaaag agagggcgga ggccgtggcc    2400
cggctggcca aggaggtcat ggaggggtg tatcccctgg ccgtgcccct ggaggtggag     2460
gtggggatag ggaggactg gctctccgcc aaggagtaa                            2499
```

<210> SEQ ID NO 26
<211> LENGTH: 832
<212> TYPE: PRT
<213> ORGANISM: Thermus aquaticus
<220> FEATURE:
<221> NAME/KEY: MISC_FEATURE
<222> LOCATION: (1)..(832)
<223> OTHER INFORMATION: X can be any amino acid except for the wild-type residue

<400> SEQUENCE: 26

```
Met Arg Gly Met Leu Pro Leu Phe Glu Pro Lys Gly Arg Val Leu Leu
1               5                   10                  15

Val Asp Gly His His Leu Ala Tyr Arg Thr Phe His Ala Leu Lys Gly
            20                  25                  30

Leu Thr Thr Ser Arg Gly Glu Pro Val Gln Ala Val Tyr Gly Phe Ala
        35                  40                  45

Lys Ser Leu Leu Lys Ala Leu Lys Glu Asp Gly Asp Ala Val Ile Val
    50                  55                  60

Val Phe Asp Ala Lys Ala Pro Ser Phe Arg His Glu Ala Tyr Gly Gly
65                  70                  75                  80

Tyr Lys Ala Gly Arg Ala Pro Thr Pro Glu Asp Phe Pro Arg Gln Leu
                85                  90                  95

Ala Leu Ile Lys Glu Leu Val Asp Leu Leu Gly Leu Ala Arg Leu Glu
            100                 105                 110

Val Pro Gly Tyr Glu Ala Asp Asp Val Leu Ala Ser Leu Ala Lys Lys
        115                 120                 125

Ala Glu Lys Glu Gly Tyr Glu Val Arg Ile Leu Thr Ala Asp Lys Asp
    130                 135                 140

Leu Tyr Gln Leu Leu Ser Asp Arg Ile His Val Leu His Pro Glu Gly
145                 150                 155                 160

Tyr Leu Ile Thr Pro Ala Trp Leu Trp Glu Lys Tyr Gly Leu Arg Pro
                165                 170                 175

Asp Gln Trp Ala Asp Tyr Arg Ala Leu Thr Gly Asp Glu Ser Asp Asn
            180                 185                 190

Leu Pro Gly Val Lys Gly Ile Gly Glu Lys Thr Ala Arg Lys Leu Leu
        195                 200                 205

Glu Glu Trp Gly Ser Leu Glu Ala Leu Leu Lys Asn Leu Asp Arg Leu
```

```
            210                 215                 220
Lys Pro Ala Ile Arg Glu Lys Ile Leu Ala His Met Asp Asp Leu Lys
225                 230                 235                 240

Leu Ser Trp Asp Xaa Ala Lys Val Arg Thr Asp Leu Pro Leu Glu Val
                245                 250                 255

Asp Phe Ala Lys Arg Arg Glu Pro Asp Arg Glu Arg Leu Arg Ala Phe
                260                 265                 270

Leu Glu Arg Leu Glu Phe Gly Ser Leu Leu His Glu Phe Gly Leu Leu
            275                 280                 285

Glu Ser Pro Lys Ala Leu Glu Ala Pro Trp Pro Pro Glu Gly
290                 295                 300

Ala Phe Val Gly Phe Val Leu Ser Arg Lys Glu Pro Met Trp Ala Asp
305                 310                 315                 320

Leu Leu Ala Leu Ala Ala Arg Gly Gly Arg Val His Arg Ala Pro
                325                 330                 335

Glu Pro Tyr Lys Ala Leu Arg Asp Leu Lys Glu Ala Arg Gly Leu Leu
                340                 345                 350

Ala Lys Asp Leu Ser Val Leu Ala Leu Arg Glu Gly Leu Gly Leu Pro
            355                 360                 365

Pro Gly Asp Asp Pro Met Leu Leu Ala Tyr Leu Leu Asp Pro Ser Asn
            370                 375                 380

Thr Thr Pro Glu Gly Val Ala Arg Arg Tyr Gly Gly Glu Trp Thr Glu
385                 390                 395                 400

Glu Ala Gly Glu Arg Ala Ala Leu Ser Glu Arg Leu Phe Ala Asn Leu
                405                 410                 415

Trp Gly Arg Leu Glu Gly Glu Arg Leu Leu Trp Leu Tyr Arg Glu
                420                 425                 430

Val Glu Arg Pro Leu Ser Ala Val Leu Ala His Met Glu Ala Thr Gly
                435                 440                 445

Val Arg Leu Asp Val Ala Tyr Leu Arg Ala Leu Ser Leu Glu Val Ala
            450                 455                 460

Glu Glu Ile Ala Arg Leu Glu Ala Glu Val Phe Arg Leu Ala Gly His
465                 470                 475                 480

Pro Phe Asn Leu Asn Ser Arg Asp Gln Leu Glu Arg Val Leu Phe Asp
                485                 490                 495

Glu Leu Gly Leu Pro Ala Ile Gly Lys Thr Xaa Lys Thr Gly Lys Arg
                500                 505                 510

Ser Thr Ser Ala Ala Val Leu Glu Ala Leu Arg Glu Ala His Pro Ile
            515                 520                 525

Val Glu Lys Ile Leu Gln Tyr Arg Glu Leu Thr Lys Leu Lys Ser Thr
            530                 535                 540

Tyr Ile Asp Pro Leu Asp Leu Ile His Pro Arg Thr Gly Arg Leu
545                 550                 555                 560

His Thr Arg Phe Asn Gln Thr Ala Thr Ala Thr Gly Arg Leu Ser Ser
                565                 570                 575

Ser Asp Pro Asn Leu Gln Asn Ile Pro Val Arg Thr Pro Leu Gly Gln
            580                 585                 590

Arg Ile Arg Arg Ala Phe Ile Ala Glu Glu Gly Trp Leu Leu Val Ala
            595                 600                 605

Leu Asp Tyr Ser Gln Ile Glu Leu Arg Val Leu Ala His Leu Ser Gly
            610                 615                 620

Asp Glu Asn Leu Ile Arg Val Phe Gln Glu Gly Arg Asp Ile His Thr
625                 630                 635                 640
```

```
Glu Thr Ala Ser Trp Met Phe Gly Val Pro Arg Ala Val Asp Pro
                645                 650                 655
Leu Met Arg Arg Ala Ala Lys Thr Ile Asn Phe Gly Val Leu Tyr Gly
            660                 665                 670
Met Ser Ala His Arg Leu Ser Gln Glu Leu Ala Ile Pro Tyr Glu Glu
        675                 680                 685
Ala Gln Ala Phe Ile Glu Arg Tyr Phe Gln Ser Phe Pro Lys Val Arg
    690                 695                 700
Ala Trp Ile Glu Lys Thr Leu Glu Glu Gly Arg Arg Arg Gly Tyr Val
705                 710                 715                 720
Glu Thr Leu Phe Gly Arg Arg Arg Tyr Val Pro Asp Leu Glu Ala Arg
                725                 730                 735
Val Lys Ser Val Arg Glu Ala Ala Glu Arg Met Ala Ile Asn Met Pro
            740                 745                 750
Val Gln Gly Thr Ala Ala Asp Leu Met Lys Leu Ala Met Val Lys Leu
        755                 760                 765
Phe Pro Arg Leu Glu Glu Met Gly Ala Arg Met Leu Leu Gln Val His
    770                 775                 780
Asp Glu Leu Val Leu Glu Ala Pro Lys Glu Arg Ala Glu Ala Val Ala
785                 790                 795                 800
Arg Leu Ala Lys Glu Val Met Glu Gly Val Tyr Pro Leu Ala Val Pro
                805                 810                 815
Leu Glu Val Glu Val Gly Ile Gly Glu Asp Trp Leu Ser Ala Lys Glu
            820                 825                 830

<210> SEQ ID NO 27
<211> LENGTH: 2499
<212> TYPE: DNA
<213> ORGANISM: Thermus aquaticus
<220> FEATURE:
<221> NAME/KEY: misc_feature
<222> LOCATION: (1)..(2499)
<223> OTHER INFORMATION: nnn can encode for any amino acid except for
      the wild-type residue

<400> SEQUENCE: 27
atgcgtggca tgcttcctct ttttgagccc aagggccggg tcctcctggt ggacggccac        60
cacctggcct accgcacctt ccacgccctg aagggcctca ccaccagccg ggggagccg        120 gtgcaggcgg tctacggctt cgccaagagc ctcctcaagg ccctcaagga ggacggggac       180
gcggtgatcg tggtctttga cgccaaggcc cctccttcc gccacgaggc ctacggggg         240 tacaaggcgg ccgggcccc cacgccggag actttcccc ggcaactcgc cctcatcaag         300
gagctggtgg acctcctggg gctggcgcgc ctcgaggtcc cgggctacga ggcggacgac       360
gtcctggcca gctggccaa gaaggcggaa aaggagggct acgaggtccg catcctcacc        420
gccgacaaag accttaccac agctcctttcc gaccgcatcc acgtcctcca ccccgagggg      480
tacctcatca ccccggcctg ctttgggaa agtacggcc tgaggcccga ccagtgggcc         540
gactaccggg ccctgaccgg ggacgagtcc gacaaccttc cggggtcaa gggcatcggg        600 gagaagacgc gaggaagct tctggaggag tggggagcc tggaagccct cctcaagaac        660
ctggaccggc tgaagcccgc catccgggag aagatcctgg cccacatgga cgatctgaag       720
ctctcctggg acnnngccaa ggtgcgcacc gacctgcccc tggaggtgga cttcgccaaa      780
aggcgggagc cgaccgggga gaggcttagg gcctttctgg agaggcttga gtttggcagc      840
ctcctccacg agttcggcct tctggaaagc ccaaggccc tggaggaggc ccctggcccc      900
```

-continued

```
ccgccggaag gggccttcgt gggctttgtg cttccccgca aggagcccat gtgggccgat      960
cttctggccc tggccgccgc caggggggc cgggtccacc gggcccccga gccttataaa     1020
gccctcaggg acctgaagga ggcgcggggg cttctcgcca aagacctgag cgttctggcc     1080
ctgagggaag gccttggcct cccgcccggc gacgacccca tgctcctcgc ctacctcctg     1140
gaccttcca acaccaccc cgaggggtg gcccggcgct acggcgggga gtggacggag       1200
gaggcgggg agcgggccgc cctttccgag aggctcttcg ccaacctgtg ggggaggctt     1260
gaggggagg agaggctcct ttggctttac cgggaggtgg agaggcccct ttccgctgtc     1320
ctggcccaca tggaggccac gggggtgcgc ctggacgtgg cctatctcag ggccttgtcc     1380
ctggaggtgg ccgaggagat cgcccgcctc gaggccgagg tcttccgcct ggccggccac     1440
cccttcaacc tcaactcccg ggaccagctg aaagggtcc tctttgacga gctagggctt     1500
cccgccatcg gcaagacgnn naagaccggc aagcgctcca ccagcgccgc cgtcctggag     1560
gccctccgcg aggcccaccc catcgtggag aagatcctgc agtaccggga gctcaccaag     1620
ctgaagagca cctacattga ccccttgccg gacctcatcc accccaggac gggccgcctc     1680
cacacccgct tcaaccagac ggccacggcc acgggcaggc taagtagctc cgatcccaac     1740
ctccagaaca tccccgtccg caccccgctt gggcagagga tccgccgggc cttcatcgcc     1800
gaggaggggt ggctattggt ggccctggac tatagccaga tagagctcag ggtgctggcc     1860
cacctctccg gcgacgagaa cctgatccgg gtcttccagg aggggcggga catccacacg     1920
gagaccgcca gctggatgtt cggcgtcccc cgggaggccg tggaccccct gatgcgccgg     1980
gcggccaaga ccatcaactt cggggtcctc tacggcatgt cggcccaccg cctctcccag     2040
gagctagcca tcccttacga ggaggcccag gccttcattg agcgctactt tcagagcttc     2100
cccaaggtgc gggcctggat tgagaagacc ctggaggagg caggaggcg ggggtacgtg     2160
gagaccctct tcggccgccg ccgctacgtg ccagacctag aggcccgggt gaagagcgtg     2220
cgggaggcgg ccgagcgcat ggccnnnaac atgcccgtcc agggcaccgc cgccgacctc     2280
atgaagctgg ctatggtgaa gctcttcccc aggctggagg aaatgggggc caggatgctc     2340
cttcaggtcc acgacgagct ggtcctcgag gccccaaaag agagggcgga ggccgtggcc     2400
cggctggcca aggaggtcat ggagggggtg tatcccctgg ccgtgcccct ggaggtggag     2460
gtggggatag ggaggactg gctctccgcc aaggagtaa                            2499
```

<210> SEQ ID NO 28
<211> LENGTH: 832
<212> TYPE: PRT
<213> ORGANISM: Thermus aquaticus

<400> SEQUENCE: 28

```
Met Arg Gly Met Leu Pro Leu Phe Glu Pro Lys Gly Arg Val Leu Leu
1               5                   10                  15

Val Asp Gly His His Leu Ala Tyr Arg Thr Phe His Ala Leu Lys Gly
            20                  25                  30

Leu Thr Thr Ser Arg Gly Glu Pro Val Gln Ala Val Tyr Gly Phe Ala
        35                  40                  45

Lys Ser Leu Leu Lys Ala Leu Lys Glu Asp Gly Asp Ala Val Ile Val
    50                  55                  60

Val Phe Asp Ala Lys Ala Pro Ser Phe Arg His Glu Ala Tyr Gly Gly
65                  70                  75                  80

Tyr Lys Ala Gly Arg Ala Pro Thr Pro Glu Asp Phe Pro Arg Gln Leu
```

-continued

```
                85                  90                  95
Ala Leu Ile Lys Glu Leu Val Asp Leu Gly Leu Ala Arg Leu Glu
                100                 105                 110
Val Pro Gly Tyr Glu Ala Asp Val Leu Ala Ser Leu Ala Lys Lys
                115                 120                 125
Ala Glu Lys Glu Gly Tyr Glu Val Arg Ile Leu Thr Ala Asp Lys Asp
            130                 135                 140
Leu Tyr Gln Leu Leu Ser Asp Arg Ile His Ile Leu His Pro Glu Gly
145                 150                 155                 160
Tyr Leu Ile Thr Pro Ala Trp Leu Trp Glu Lys Tyr Gly Leu Arg Pro
                165                 170                 175
Asp Gln Trp Ala Asp Tyr Arg Ala Leu Thr Gly Asp Glu Ser Asp Asn
            180                 185                 190
Leu Pro Gly Val Lys Gly Ile Gly Glu Lys Thr Ala Arg Lys Leu Leu
                195                 200                 205
Glu Glu Trp Gly Ser Leu Glu Ala Leu Leu Lys Asn Leu Asp Arg Leu
        210                 215                 220
Lys Pro Ala Ile Arg Glu Lys Ile Leu Ala His Met Asp Asp Leu Lys
225                 230                 235                 240
Leu Ser Trp Asp Met Ala Lys Val Arg Thr Asp Leu Pro Leu Glu Val
                245                 250                 255
Asp Phe Ala Lys Arg Arg Glu Pro Asp Arg Glu Arg Leu Arg Ala Phe
            260                 265                 270
Leu Glu Arg Leu Glu Phe Gly Ser Leu Leu His Glu Phe Gly Leu Leu
        275                 280                 285
Glu Ser Pro Lys Ala Leu Glu Glu Ala Pro Trp Pro Pro Glu Gly
        290                 295                 300
Ala Phe Val Gly Phe Val Leu Ser Arg Lys Glu Pro Met Trp Ala Asp
305                 310                 315                 320
Leu Leu Ala Leu Ala Ala Arg Gly Gly Arg Val His Arg Ala Pro
            325                 330                 335
Glu Pro Tyr Lys Ala Leu Arg Asp Leu Lys Glu Ala Arg Gly Leu Leu
            340                 345                 350
Ala Lys Asp Leu Ser Val Leu Ala Leu Arg Glu Gly Leu Gly Leu Pro
        355                 360                 365
Pro Gly Asp Asp Pro Met Leu Leu Ala Tyr Leu Leu Asp Pro Ser Asn
        370                 375                 380
Thr Thr Pro Glu Gly Val Ala Arg Arg Tyr Gly Gly Glu Trp Thr Glu
385                 390                 395                 400
Glu Ala Gly Glu Arg Ala Ala Leu Ser Glu Arg Leu Phe Ala Asn Leu
                405                 410                 415
Trp Gly Arg Leu Glu Gly Glu Glu Arg Leu Leu Trp Leu Tyr Arg Glu
            420                 425                 430
Val Glu Arg Pro Leu Ser Ala Val Leu Ala His Met Glu Ala Thr Gly
            435                 440                 445
Val Arg Leu Asp Val Ala Tyr Leu Arg Ala Leu Ser Leu Glu Val Ala
        450                 455                 460
Glu Glu Ile Ala Arg Leu Glu Ala Glu Val Phe Arg Leu Ala Gly His
465                 470                 475                 480
Pro Phe Asn Leu Asn Ser Arg Asp Gln Leu Glu Arg Val Leu Phe Asp
            485                 490                 495
Glu Leu Gly Leu Pro Ala Ile Gly Lys Thr Lys Thr Gly Lys Arg
        500                 505                 510
```

```
Ser Thr Ser Ala Ala Val Leu Glu Ala Leu Arg Glu Ala His Pro Ile
            515                 520                 525

Val Glu Lys Ile Leu Gln Tyr Arg Glu Leu Thr Lys Leu Lys Ser Thr
        530                 535                 540

Tyr Ile Asp Pro Leu Pro Asp Leu Ile His Pro Arg Thr Gly Arg Leu
545                 550                 555                 560

His Thr Arg Phe Asn Gln Thr Ala Thr Ala Thr Gly Arg Leu Ser Ser
                565                 570                 575

Ser Asp Pro Asn Leu Gln Asn Ile Pro Val Arg Thr Pro Leu Gly Gln
            580                 585                 590

Arg Ile Arg Arg Ala Phe Ile Ala Glu Glu Gly Trp Leu Leu Val Ala
        595                 600                 605

Leu Asp Tyr Ser Gln Ile Glu Leu Arg Val Leu Ala His Leu Ser Gly
            610                 615                 620

Asp Glu Asn Leu Ile Arg Val Phe Gln Glu Gly Arg Asp Ile His Thr
625                 630                 635                 640

Glu Thr Ala Ser Trp Met Phe Gly Val Pro Arg Glu Ala Val Asp Pro
                645                 650                 655

Leu Met Arg Arg Ala Ala Lys Thr Ile Asn Phe Gly Val Leu Tyr Gly
        660                 665                 670

Met Ser Ala His Arg Leu Ser Gln Glu Leu Ala Ile Pro Tyr Glu Glu
            675                 680                 685

Ala Gln Ala Phe Ile Glu Arg Tyr Phe Gln Ser Phe Pro Lys Val Arg
        690                 695                 700

Ala Trp Ile Glu Lys Thr Leu Glu Glu Gly Arg Arg Arg Gly Tyr Val
705                 710                 715                 720

Glu Thr Leu Phe Gly Arg Arg Arg Tyr Val Pro Asp Leu Glu Ala Arg
                725                 730                 735

Val Lys Ser Val Arg Glu Ala Ala Glu Arg Met Ala Ile Asn Met Pro
            740                 745                 750

Val Gln Gly Thr Ala Ala Asp Leu Met Lys Leu Ala Met Val Lys Leu
        755                 760                 765

Phe Pro Arg Leu Glu Glu Met Gly Ala Arg Met Leu Leu Gln Val His
    770                 775                 780

Asp Glu Leu Val Leu Glu Ala Pro Lys Glu Arg Ala Glu Ala Val Ala
785                 790                 795                 800

Arg Leu Ala Lys Glu Val Met Glu Gly Val Tyr Pro Leu Ala Val Pro
                805                 810                 815

Leu Glu Val Glu Val Gly Ile Gly Glu Asp Trp Leu Ser Ala Lys Glu
            820                 825                 830

<210> SEQ ID NO 29
<211> LENGTH: 2499
<212> TYPE: DNA
<213> ORGANISM: Thermus aquaticus

<400> SEQUENCE: 29
atgcgtggca tgcttcctct ttttgagccc aagggccggg tcctcctggt ggacggccac      60
cacctggcct accgcacctt ccacgccctg aaggcctca ccaccagccg ggggagccg      120 gtgcaggcgg tctacggctt cgccaagagc ctcctcaagg ccctcaagga ggacggggac      180
gcggtgatcg tggtctttga cgccaaggcc cctccttcc gccacgaggc ctacggggg      240 tacaaggcgg gccgggcccc cacgccggag gactttcccc ggcaactcgc cctcatcaag      300
```

```
gagctggtgg aacctcctggg gctggcgcgc ctcgaggtcc cgggctacga ggcggacgac    360
gtcctggcca gcctggccaa gaaggcggaa aaggagggct acgaggtccg catcctcacc    420
gccgacaaag acctttacca gctccttttc gaccgcatcc acatcctcca ccccgagggg    480
tacctcatca ccccggcctg gctttgggaa aagtacggcc tgaggcccga ccagtgggcc    540
gactaccggg ccctgaccgg ggacgagtcc gacaaccttc cggggtcaa gggcatcggg    600
gagaagacgc gaggaagct tctggaggag tggggagcc tggaagccct cctcaagaac    660
ctggaccggc tgaagcccgc catccgggag aagatcctgg cccacatgga cgatctgaag    720
ctctcctggg acatggccaa ggtgcgcacc gacctgcccc tggaggtgga cttcgccaaa    780
aggcgggagc ccgaccggga gaggcttagg gcctttctgg agaggcttga gtttggcagc    840
ctcctccacg agttcggcct tctggaaagc cccaaggccc tggaggaggc ccctggccc    900
ccgccggaag gggccttcgt gggctttgtg cttccccgca aggagcccat gtgggccgat    960
cttctggccc tggccgccgc caggggggc cgggtccacc gggcccccga gccttataaa    1020
gccctcaggg acctgaagga ggcgcggggg cttctcgcca aagacctgag cgttctggcc    1080
ctgagggaag gccttggcct cccgcccggc gacgaccccca tgctcctcgc ctacctcctg    1140
gacccttcca acaccacccc cgaggggtg gcccggcgct acggcggga gtggacggag    1200
gaggcggggg agcgggccgc cctttccgag aggctcttcg ccaacctgtg ggggaggctt    1260
gaggggggagg agaggctcct ttggctttac cgggaggtgg agaggcccct ttccgctgtc    1320
ctggcccaca tggaggccac gggggtgcgc ctggacgtgg cctatctcag ggccttgtcc    1380
ctggaggtgg ccgaggagat cgcccgcctc gaggccgagg tcttccgcct ggccggccac    1440
cccttcaacc tcaactcccg ggaccagctg gaaagggtcc tctttgacga gctagggctt    1500
cccgccatcg gcaagacgaa gaagaccggc aagcgctcca ccagcgccgc cgtcctggag    1560
gccctccgcg aggcccaccc catcgtggag aagatcctgc agtaccggga gctcaccaag    1620
ctgaagagca cctacattga ccccttgccg gacctcatcc accccaggac gggccgcctc    1680
cacacccgct tcaaccagac ggccacggcc acgggcaggc taagtagctc cgatcccaac    1740
ctccagaaca tccccgtccg caccccgctt gggcagagga tccgccgggc cttcatcgcc    1800
gaggaggggt ggctattggt ggccctggac tatagccaga tagagctcag ggtgctggcc    1860
cacctctccg cgacgagaa cctgatccgg gtcttccagg aggggcggga catccacacg    1920
gagaccgcca gctggatgtt cggcgtcccc cgggaggccg tggaccccct gatgcgccgg    1980
gcggccaaga ccatcaactt cggggtcctc tacggcatgt cggcccaccg cctctcccag    2040
gagctagcca tcccttacga ggaggcccag gccttcattg agcgctactt tcagagcttc    2100
cccaaggtgc gggcctggat tgagaagacc ctggaggagg caggaggcg ggggtacgtg    2160
gagaccctct tcggccgccg ccgctacgtg ccagacctag aggcccgggt gaagagcgtg    2220
cgggaggcgg ccgagcgcat ggccatcaac atgcccgtcc agggcaccgc cgccgacctc    2280
atgaagctgg ctatggtgaa gctcttcccc aggctggagg aaatgggggc caggatgctc    2340
cttcaggtcc acgacgagct ggtcctcgag gccccaaaag agagggcgga ggccgtggcc    2400
cggctggcca aggaggtcat ggaggggtg tatcccctgg ccgtgcccct ggaggtggag    2460
gtggggatag ggaggactg gctctccgcc aaggagtaa            2499
```

<210> SEQ ID NO 30
<211> LENGTH: 832
<212> TYPE: PRT
<213> ORGANISM: Thermus aquaticus

```
<220> FEATURE:
<221> NAME/KEY: MISC_FEATURE
<222> LOCATION: (1)..(832)
<223> OTHER INFORMATION: X can be any amino acid except for the
      wild-type residue

<400> SEQUENCE: 30

Met Arg Gly Met Leu Pro Leu Phe Glu Pro Lys Gly Arg Val Leu Leu
1               5                   10                  15

Val Asp Gly His His Leu Ala Tyr Arg Thr Phe His Ala Leu Lys Gly
            20                  25                  30

Leu Thr Thr Ser Arg Gly Glu Pro Val Gln Ala Val Tyr Gly Phe Ala
        35                  40                  45

Lys Ser Leu Leu Lys Ala Leu Lys Glu Asp Gly Asp Ala Val Ile Val
50                  55                  60

Val Phe Asp Ala Lys Ala Pro Ser Phe Arg His Glu Ala Tyr Gly Gly
65                  70                  75                  80

Tyr Lys Ala Gly Arg Ala Pro Thr Pro Glu Asp Phe Pro Arg Gln Leu
                85                  90                  95

Ala Leu Ile Lys Glu Leu Val Asp Leu Leu Gly Leu Ala Arg Leu Glu
            100                 105                 110

Val Pro Gly Tyr Glu Ala Asp Asp Val Leu Ala Ser Leu Ala Lys Lys
        115                 120                 125

Ala Glu Lys Glu Gly Tyr Glu Val Arg Ile Leu Thr Ala Asp Lys Asp
130                 135                 140

Leu Tyr Gln Leu Leu Ser Asp Arg Ile His Xaa Leu His Pro Glu Gly
145                 150                 155                 160

Tyr Leu Ile Thr Pro Ala Trp Leu Trp Glu Lys Tyr Gly Leu Arg Pro
                165                 170                 175

Asp Gln Trp Ala Asp Tyr Arg Ala Leu Thr Gly Asp Glu Ser Asp Asn
            180                 185                 190

Leu Pro Gly Val Lys Gly Ile Gly Glu Lys Thr Ala Arg Lys Leu Leu
        195                 200                 205

Glu Glu Trp Gly Ser Leu Glu Ala Leu Leu Lys Asn Leu Asp Arg Leu
210                 215                 220

Lys Pro Ala Ile Arg Glu Lys Ile Leu Ala His Met Asp Asp Leu Lys
225                 230                 235                 240

Leu Ser Trp Asp Xaa Ala Lys Val Arg Thr Asp Leu Pro Leu Glu Val
                245                 250                 255

Asp Phe Ala Lys Arg Arg Glu Pro Asp Arg Glu Arg Leu Arg Ala Phe
            260                 265                 270

Leu Glu Arg Leu Glu Phe Gly Ser Leu Leu His Glu Phe Gly Leu Leu
        275                 280                 285

Glu Ser Pro Lys Ala Leu Glu Glu Ala Pro Trp Pro Pro Pro Glu Gly
290                 295                 300

Ala Phe Val Gly Phe Val Leu Ser Arg Lys Glu Pro Met Trp Ala Asp
305                 310                 315                 320

Leu Leu Ala Leu Ala Ala Ala Arg Gly Gly Arg Val His Arg Ala Pro
                325                 330                 335

Glu Pro Tyr Lys Ala Leu Arg Asp Leu Lys Glu Ala Arg Gly Leu Leu
            340                 345                 350

Ala Lys Asp Leu Ser Val Leu Ala Leu Arg Glu Gly Leu Gly Leu Pro
        355                 360                 365

Pro Gly Asp Asp Pro Met Leu Leu Ala Tyr Leu Leu Asp Pro Ser Asn
370                 375                 380
```

Thr Thr Pro Glu Gly Val Ala Arg Arg Tyr Gly Gly Glu Trp Thr Glu
385                 390                 395                 400

Glu Ala Gly Glu Arg Ala Ala Leu Ser Glu Arg Leu Phe Ala Asn Leu
            405                 410                 415

Trp Gly Arg Leu Glu Gly Glu Arg Leu Leu Trp Leu Tyr Arg Glu
        420                 425                 430

Val Glu Arg Pro Leu Ser Ala Val Leu Ala His Met Glu Ala Thr Gly
            435                 440                 445

Val Arg Leu Asp Val Ala Tyr Leu Arg Ala Leu Ser Leu Glu Val Ala
    450                 455                 460

Glu Glu Ile Ala Arg Leu Glu Ala Glu Val Phe Arg Leu Ala Gly His
465                 470                 475                 480

Pro Phe Asn Leu Asn Ser Arg Asp Gln Leu Glu Arg Val Leu Phe Asp
            485                 490                 495

Glu Leu Gly Leu Pro Ala Ile Gly Lys Thr Xaa Lys Thr Gly Lys Arg
        500                 505                 510

Ser Thr Ser Ala Ala Val Leu Glu Ala Leu Arg Glu Ala His Pro Ile
        515                 520                 525

Val Glu Lys Ile Leu Gln Tyr Arg Glu Leu Thr Lys Leu Lys Ser Thr
    530                 535                 540

Tyr Ile Asp Pro Leu Pro Asp Leu Ile His Pro Arg Thr Gly Arg Leu
545                 550                 555                 560

His Thr Arg Phe Asn Gln Thr Ala Thr Ala Thr Gly Arg Leu Ser Ser
            565                 570                 575

Ser Asp Pro Asn Leu Gln Asn Ile Pro Val Arg Thr Pro Leu Gly Gln
        580                 585                 590

Arg Ile Arg Arg Ala Phe Ile Ala Glu Glu Gly Trp Leu Leu Val Ala
        595                 600                 605

Leu Asp Tyr Ser Gln Ile Glu Leu Arg Val Leu Ala His Leu Ser Gly
    610                 615                 620

Asp Glu Asn Leu Ile Arg Val Phe Gln Glu Gly Arg Asp Ile His Thr
625                 630                 635                 640

Glu Thr Ala Ser Trp Met Phe Gly Val Pro Arg Glu Ala Val Asp Pro
            645                 650                 655

Leu Met Arg Arg Ala Ala Lys Thr Ile Asn Phe Gly Val Leu Tyr Gly
        660                 665                 670

Met Ser Ala His Arg Leu Ser Gln Glu Leu Ala Ile Pro Tyr Glu Glu
        675                 680                 685

Ala Gln Ala Phe Ile Glu Arg Tyr Phe Gln Ser Phe Pro Lys Val Arg
    690                 695                 700

Ala Trp Ile Glu Lys Thr Leu Glu Glu Gly Arg Arg Gly Tyr Val
705                 710                 715                 720

Glu Thr Leu Phe Gly Arg Arg Tyr Val Pro Asp Leu Glu Ala Arg
            725                 730                 735

Val Lys Ser Val Arg Glu Ala Ala Glu Arg Met Ala Xaa Asn Met Pro
        740                 745                 750

Val Gln Gly Thr Ala Ala Asp Leu Met Lys Leu Ala Met Val Lys Leu
    755                 760                 765

Phe Pro Arg Leu Glu Glu Met Gly Ala Arg Met Leu Leu Gln Val His
    770                 775                 780

Asp Glu Leu Val Leu Glu Ala Pro Lys Glu Arg Ala Glu Ala Val Ala
785                 790                 795                 800

```
        Arg Leu Ala Lys Glu Val Met Glu Gly Val Tyr Pro Leu Ala Val Pro
                    805                 810                 815

Leu Glu Val Glu Val Gly Ile Gly Glu Asp Trp Leu Ser Ala Lys Glu
                820                 825                 830

<210> SEQ ID NO 31
<211> LENGTH: 2499
<212> TYPE: DNA
<213> ORGANISM: Thermus aquaticus
<220> FEATURE:
<221> NAME/KEY: misc_feature
<222> LOCATION: (1)..(2499)
<223> OTHER INFORMATION: nnn can encode for any amino acid except for
      the wild-type residue

<400> SEQUENCE: 31
atgcgtggca tgcttcctct ttttgagccc aagggccggg tcctcctggt ggacggccac      60
cacctggcct accgcacctt ccacgccctg aagggcctca ccaccagccg gggggagccg     120
gtgcaggcgg tctacggctt cgccaagagc ctcctcaagg ccctcaagga ggacgggga     180 gcggtgatcg tggtctttga cgccaaggcc ccctccttcc gccacgaggc ctacgggggg     240
tacaaggcgg ccgggccccc cacgcggag gactttcccc ggcaactcgc cctcatcaag     300
gagctggtgg acctcctggg gctggcgcgc ctcgaggtcc cgggctacga ggcggacgac     360
gtcctggcca gcctggccaa gaaggcggaa aaggagggct acgaggtccg catcctcacc     420
gccgacaaag acctttacca gctcctttcc gaccgcatcc acnnnctcca ccccgagggg     480
tacctcatca cccccgcctg gctttgggaa aagtacggcc tgaggcccga ccagtgggcc     540
gactaccggg ccctgaccgg ggacgagtcc gacaaccttc ccgggtcaa gggcatcggg     600 gagaagacgg cgaggaagct tctggaggag tgggggagcc tggaagccct cctcaagaac     660
ctggaccggc tgaagcccgc catccgggag aagatcctgg cccacatgga cgatctgaag     720
ctctcctggg acnnngccaa ggtgcgcacc gacctgcccc tggaggtgga cttcgccaaa     780
aggcgggagc ccgaccggga gaggcttagg gcctttctgg agaggcttga gtttggcagc     840
ctcctccacg agttcggcct tctggaaagc cccaaggccc tggaggaggc ccccctggcc     900
ccgccggaag gggccttcgt gggctttgtg ctttcccgca aggagcccat gtgggccgat     960
cttctggccc tggccgccgc cagggggggc cgggtccacc gggcccccga gccttataaa    1020
gccctcaggg acctgaagga ggcgcggggg cttctcgcca agacctgag cgttctggcc    1080 ctgagggaag gccttggcct cccgccggc gacgacccca tgctcctcgc ctacctcctg    1140
gacccttcca caccaccccc gagggggtg gcccggcgct acggcgggga gtggacggag    1200
gaggcggggg agcgggccgc cctttccgag aggctcttcg ccaacctgtg ggggaggctt    1260 gaggggggagg agaggctcct ttggctttac cggaggtgg agaggcccct ttccgctgtc    1320
ctggcccaca tggaggccac gggggtgcgc ctggacgtgg cctatctcag ggccttgtcc    1380
ctggaggtgg ccgaggagat cgcccgcctc gaggccgagg tcttccgcct ggccggccac    1440
cccttcaacc tcaactcccg ggaccagctg gaaagggtcc tctttgacga gctagggctt    1500
cccgccatcg gcaagacgnn naagaccggc aagcgctcca ccagcgccgc cgtcctggag    1560
gccctccgcg aggcccaccc catcgtggag aagatcctgc agtaccggga gctcaccaag    1620
ctgaagagca cctacattga cccccttgccg gacctcatcc accccaggac gggccgcctc    1680
cacacccgct caaccagac ggccacggcc acgggcaggc taagtagctc cgatcccaac    1740
ctccagaaca tccccgtccg cacccgcgctt gggcagagga tccgccgggc cttcatcgcc    1800
```

```
gaggaggggt ggctattggt ggccctggac tatagccaga tagagctcag ggtgctggcc      1860
cacctctccg gcgacgagaa cctgatccgg gtcttccagg aggggcggga catccacacg      1920
gagaccgcca gctggatgtt cggcgtcccc cgggaggccg tggacccct  gatgcgccgg      1980 gcggccaaga ccatcaactt cggggtcctc tacggcatgt cggcccaccg cctctcccag      2040
gagctagcca tcccttacga ggaggcccag gccttcattg agcgctactt tcagagcttc      2100
cccaaggtgc gggcctggat tgagaagacc ctggaggagg gcaggaggcg ggggtacgtg      2160
gagaccctct tcggccgccg ccgctacgtg ccagacctag aggcccgggt gaagagcgtg      2220
cgggaggcgg ccgagcgcat ggccnnnaac atgcccgtcc agggcaccgc cgccgacctc      2280
atgaagctgg ctatggtgaa gctcttcccc aggctggagg aaatgggggc aggatgctc       2340 cttcaggtcc acgacgagct ggtcctcgag gccccaaaag agagggcgga ggccgtggcc      2400
cggctggcca aggaggtcat ggaggggtg  tatcccctgg ccgtgcccct ggaggtggag      2460
gtggggatag ggaggactg  gctctccgcc aaggagtaa                             2499

<210> SEQ ID NO 32
<211> LENGTH: 832
<212> TYPE: PRT
<213> ORGANISM: Thermus aquaticus

<400> SEQUENCE: 32

Met Arg Gly Met Leu Pro Leu Phe Glu Pro Lys Gly Arg Val Leu Leu
1               5                   10                  15

Val Asp Gly His His Leu Ala Tyr Arg Thr Phe His Ala Leu Lys Gly
            20                  25                  30

Leu Thr Thr Ser Arg Gly Glu Pro Val Gln Ala Val Tyr Gly Phe Ala
        35                  40                  45

Lys Ser Leu Leu Lys Ala Leu Lys Glu Asp Trp Asp Ala Val Ile Val
    50                  55                  60

Val Phe Asp Ala Lys Ala Pro Ser Phe Arg His Glu Ala Tyr Gly Gly
65                  70                  75                  80

Tyr Lys Ala Gly Arg Ala Pro Thr Pro Glu Asp Phe Pro Arg Gln Leu
                85                  90                  95

Ala Leu Ile Lys Glu Leu Val Asp Leu Leu Gly Leu Ala Arg Leu Glu
            100                 105                 110

Val Pro Gly Tyr Glu Ala Asp Asp Val Leu Ala Ser Leu Ala Lys Lys
        115                 120                 125

Ala Glu Lys Glu Gly Tyr Glu Val Arg Ile Leu Thr Ala Asp Lys Asp
    130                 135                 140

Leu Tyr Gln Leu Leu Ser Asp Arg Ile His Val Leu His Pro Glu Gly
145                 150                 155                 160

Tyr Leu Ile Thr Pro Ala Trp Leu Trp Glu Lys Tyr Gly Leu Arg Pro
                165                 170                 175

Asp Gln Trp Ala Asp Tyr Arg Ala Leu Thr Gly Asp Glu Ser Asp Asn
            180                 185                 190

Leu Pro Gly Val Lys Gly Ile Gly Glu Lys Thr Ala Arg Lys Leu Leu
        195                 200                 205

Glu Glu Trp Gly Ser Leu Glu Ala Leu Leu Lys Asn Leu Asp Arg Leu
    210                 215                 220

Lys Pro Ala Ile Arg Glu Lys Ile Leu Ala His Met Asp Asp Leu Lys
225                 230                 235                 240

Leu Ser Trp Asp Met Ala Lys Val Arg Thr Asp Leu Pro Leu Glu Val
                245                 250                 255
```

-continued

```
Asp Phe Ala Lys Arg Arg Glu Pro Asp Arg Glu Arg Leu Arg Ala Phe
            260                 265                 270
Leu Glu Arg Leu Glu Phe Gly Ser Leu Leu His Glu Phe Gly Leu Leu
        275                 280                 285
Glu Ser Pro Lys Ala Leu Glu Glu Ala Pro Trp Pro Pro Glu Gly
    290                 295                 300
Ala Phe Val Gly Phe Val Leu Ser Arg Lys Glu Pro Met Trp Ala Asp
305                 310                 315                 320
Leu Leu Ala Leu Ala Ala Arg Gly Gly Arg Val His Arg Ala Pro
                325                 330                 335
Glu Pro Tyr Lys Ala Leu Arg Asp Leu Lys Glu Ala Arg Gly Leu Leu
            340                 345                 350
Ala Lys Asp Leu Ser Val Leu Ala Leu Arg Glu Gly Leu Gly Leu Pro
        355                 360                 365
Pro Gly Asp Asp Pro Met Val Leu Ala Tyr Leu Leu Asp Pro Ser Asn
    370                 375                 380
Thr Thr Pro Glu Gly Val Ala Arg Arg Tyr Gly Gly Glu Trp Thr Glu
385                 390                 395                 400
Glu Ala Gly Glu Arg Ala Ala Leu Ser Glu Arg Leu Phe Ala Asn Leu
                405                 410                 415
Trp Gly Arg Leu Glu Gly Glu Glu Arg Leu Leu Trp Leu Tyr Arg Glu
            420                 425                 430
Val Glu Arg Pro Leu Ser Ala Val Leu Ala His Met Glu Ala Thr Gly
        435                 440                 445
Val Arg Leu Asp Val Ala Tyr Leu Arg Ala Leu Ser Leu Glu Val Ala
    450                 455                 460
Glu Glu Ile Ala Arg Leu Glu Ala Glu Val Phe Arg Leu Ala Gly His
465                 470                 475                 480
Pro Phe Asn Leu Asn Ser Arg Asp Gln Leu Glu Arg Val Leu Phe Asp
                485                 490                 495
Glu Leu Gly Leu Pro Ala Ile Gly Lys Thr Lys Thr Gly Lys Arg
            500                 505                 510
Ser Thr Ser Ala Ala Val Leu Glu Ala Leu Arg Glu Ala His Pro Ile
        515                 520                 525
Val Glu Lys Ile Leu Gln Tyr Arg Glu Leu Thr Lys Leu Lys Ser Thr
    530                 535                 540
Tyr Ile Asp Pro Leu Pro Asp Leu Ile His Pro Arg Thr Gly Arg Leu
545                 550                 555                 560
His Thr Arg Phe Asn Gln Thr Ala Thr Ala Thr Gly Arg Leu Ser Ser
                565                 570                 575
Ser Asp Pro Asn Leu Gln Asn Ile Pro Val Arg Thr Pro Leu Gly Gln
            580                 585                 590
Arg Ile Arg Arg Ala Phe Ile Ala Glu Glu Gly Trp Leu Leu Val Ala
        595                 600                 605
Leu Asp Tyr Ser Gln Ile Glu Leu Arg Val Leu Ala His Leu Ser Gly
    610                 615                 620
Asp Glu Asn Leu Ile Arg Val Phe Gln Glu Gly Arg Asp Ile His Thr
625                 630                 635                 640
Glu Thr Ala Ser Trp Met Phe Gly Val Pro Arg Glu Ala Val Asp Pro
                645                 650                 655
Leu Met Arg Arg Ala Ala Lys Thr Ile Asn Phe Gly Val Leu Tyr Gly
            660                 665                 670
```

-continued

```
Met Ser Ala His Arg Leu Ser Gln Glu Leu Ala Ile Pro Tyr Glu Glu
            675                 680                 685

Ala Gln Ala Phe Ile Glu Arg Tyr Phe Gln Ser Phe Pro Lys Val Arg
        690                 695                 700

Ala Trp Ile Glu Lys Thr Leu Glu Glu Gly Arg Arg Arg Gly Tyr Val
705                 710                 715                 720

Glu Thr Leu Phe Gly Arg Arg Arg Tyr Val Pro Asp Leu Gly Ala Arg
                725                 730                 735

Val Lys Ser Val Arg Glu Ala Ala Glu Arg Met Ala Ile Asn Met Pro
            740                 745                 750

Val Gln Gly Thr Ala Ala Asp Leu Met Lys Leu Ala Met Val Lys Leu
        755                 760                 765

Phe Pro Arg Leu Glu Glu Met Gly Ala Arg Met Leu Leu Gln Val His
    770                 775                 780

Asp Glu Leu Val Leu Glu Ala Pro Lys Glu Arg Ala Glu Ala Val Ala
785                 790                 795                 800

Arg Leu Ala Lys Glu Val Met Glu Gly Val Tyr Pro Leu Ala Val Pro
                805                 810                 815

Leu Glu Val Glu Val Gly Ile Gly Glu Asp Trp Leu Ser Ala Lys Glu
            820                 825                 830
```

<210> SEQ ID NO 33
<211> LENGTH: 2499
<212> TYPE: DNA
<213> ORGANISM: Thermus aquaticus

<400> SEQUENCE: 33

| | |
|---|---|
| atgcgtggca tgcttcctct ttttgagccc aagggccggg tcctcctggt ggacggccac | 60 |
| cacctggcct accgcacctt ccacgccctg aagggcctca ccaccagccg ggggagccg | 120 |
| gtgcaggcgg tctacggctt cgccaagagc ctcctcaagg ccctcaagga ggactgggac | 180 |
| gcggtgatcg tggtctttga cgccaaggcc cctccttcc gccacgaggc ctacggggg | 240 |
| tacaaggcgg ccgggcccc cacgccggag gactttcccc ggcaactcgc cctcatcaag | 300 |
| gagctggtgg acctcctggg gctggcgcgc tcgaggtcc cgggctacga ggcggacgac | 360 |
| gtcctggcca gcctggccaa gaaggcggaa aaggagggct acgaggtccg catcctcacc | 420 |
| gccgacaaag accttttacca gctcctttcc gaccgcatcc acgtcctcca ccccgagggg | 480 |
| tacctcatca cccccggcctg gctttgggaa aagtacggcc tgaggcccga ccagtgggcc | 540 |
| gactaccggg ccctgaccgg ggacgagtcc gacaaccttc ccggggtcaa gggcatcggg | 600 |
| gagaagacgg cgaggaagct tctggaggag tgggggagcc tggaagccct cctcaagaac | 660 |
| ctggaccggc tgaagcccgc catccgggag aagatcctgg cccacatgga cgatctgaag | 720 |
| ctctcctggg acatggccaa ggtgcgcacc gacctgcccc tggaggtgga cttcgccaaa | 780 |
| aggcgggagc cgaccgggga gaggcttagg gcctttctgg agaggcttga gtttggcagc | 840 |
| ctcctccacg agttcggcct tctggaaagc cccaaggccc tggaggaggc ccctggcccc | 900 |
| ccgccggaag ggccttcgt gggctttgtg cttttcccgca aggagcccat gtgggccgat | 960 |
| cttctgcccc tggccgccgc cagggggggc cgggtccacc gggcccccga gccttataaa | 1020 |
| gccctcaggg acctgaagga ggcgcggggg cttctcgcca aagacctgag cgttctggcc | 1080 |
| ctgagggaag gccttggcct cccgcccggc gacgacccca tggtcctcgc ctacctcctg | 1140 |
| gacccttcca acaccacccc cgaggggggtg gcccggcgct acggcgggga gtggacggag | 1200 |
| gaggcggggg agcgggccgc ccttttccgag aggctcttcg ccaacctgtg ggggaggctt | 1260 |

```
gagggggagg agaggctcct ttggctttac cgggaggtgg agaggcccct ttccgctgtc   1320
ctggcccaca tggaggccac ggggtgcgc ctggacgtgg cctatctcag ggccttgtcc   1380
ctggaggtgg ccgaggagat cgcccgcctc gaggccgagg tcttccgcct ggccggccac   1440
cccttcaacc tcaactcccg ggaccagctg aaagggtcc tctttgacga gctagggctt   1500
cccgccatcg gcaagacgaa gaagaccggc aagcgctcca ccagcgccgc cgtcctggag   1560
gccctccgcg aggcccaccc catcgtggag aagatcctgc agtaccggga gctcaccaag   1620
ctgaagagca cctacattga ccccttgccg gacctcatcc accccaggac gggccgcctc   1680
cacacccgct caaccagac ggccacggcc acgggcaggc taagtagctc cgatcccaac   1740
ctccagaaca tccccgtccg caccccgctt gggcagagga tccgccgggc cttcatcgcc   1800
gaggagggt ggctattggt ggccctggac tatagccaga tagagctcag ggtgctggcc   1860
cacctctccg cgacgagaa cctgatccgg gtcttccagg aggggcggga catccacacg   1920
gagaccgcca gctggatgtt cggcgtcccc cgggaggccg tggacccct gatgcgccgg   1980
gcggccaaga ccatcaactt cggggtcctc tacggcatgt cggcccaccg cctctcccag   2040
gagctagcca tcccttacga ggaggcccag gccttcattg agcgctactt tcagagcttc   2100
cccaaggtgc gggcctggat tgagaagacc ctggaggagg caggaggcg gggtacgtg   2160
gagaccctct tcggccgccg ccgctacgtg ccagacctag ggcccgggt gaagagcgtg   2220
cgggaggcgg ccgagcgcat ggccatcaac atgcccgtcc agggcaccgc cgccgacctc   2280
atgaagctgg ctatggtgaa gctcttcccc aggctggagg aaatggggc caggatgctc   2340
cttcaggtcc acgacgagct ggtcctcgag gccccaaaag agagggcgga ggccgtggcc   2400
cggctggcca aggaggtcat ggaggggtg tatccctgg ccgtgcccct ggaggtggag   2460
gtggggatag gggaggactg gctctccgcc aaggagtaa                          2499
```

<210> SEQ ID NO 34  
<211> LENGTH: 832  
<212> TYPE: PRT  
<213> ORGANISM: Thermus aquaticus

<400> SEQUENCE: 34

```
Met Arg Gly Met Leu Pro Leu Phe Glu Pro Lys Gly Arg Val Leu Leu
1               5                   10                  15

Val Asp Gly His His Leu Ala Tyr Arg Thr Phe His Ala Leu Lys Gly
                20                  25                  30

Leu Thr Thr Ser Arg Gly Glu Pro Val Gln Ala Val Tyr Gly Phe Ala
            35                  40                  45

Lys Ser Leu Leu Lys Ala Leu Lys Glu Asp Trp Asp Ala Val Ile Val
        50                  55                  60

Val Phe Asp Ala Lys Ala Pro Ser Phe Arg His Glu Ala Tyr Gly Gly
65                  70                  75                  80

Tyr Lys Ala Gly Arg Ala Pro Thr Pro Glu Asp Phe Pro Arg Gln Leu
                85                  90                  95

Ala Leu Ile Lys Glu Leu Val Asp Leu Leu Gly Leu Ala Arg Leu Glu
            100                 105                 110

Val Pro Gly Tyr Glu Ala Asp Asp Val Leu Ala Ser Leu Ala Lys Lys
        115                 120                 125

Ala Glu Lys Glu Gly Tyr Glu Val Arg Ile Leu Thr Ala Asp Lys Asp
    130                 135                 140

Leu Tyr Gln Leu Leu Ser Asp Arg Ile His Ile Leu His Pro Glu Gly
```

```
            145                 150                 155                 160
Tyr Leu Ile Thr Pro Ala Trp Leu Trp Glu Lys Tyr Gly Leu Arg Pro
                    165                 170                 175

Asp Gln Trp Ala Asp Tyr Arg Ala Leu Thr Gly Asp Glu Ser Asp Asn
                    180                 185                 190

Leu Pro Gly Val Lys Gly Ile Gly Glu Lys Thr Ala Arg Lys Leu Leu
                    195                 200                 205

Glu Glu Trp Gly Ser Leu Glu Ala Leu Leu Lys Asn Leu Asp Arg Leu
                    210                 215                 220

Lys Pro Ala Ile Arg Glu Lys Ile Leu Ala His Met Asp Asp Leu Lys
225                 230                 235                 240

Leu Ser Trp Asp Met Ala Lys Val Arg Thr Asp Leu Pro Leu Glu Val
                    245                 250                 255

Asp Phe Ala Lys Arg Arg Glu Pro Asp Arg Glu Arg Leu Arg Ala Phe
                    260                 265                 270

Leu Glu Arg Leu Glu Phe Gly Ser Leu Leu His Glu Phe Gly Leu Leu
                    275                 280                 285

Glu Ser Pro Lys Ala Leu Glu Glu Ala Pro Trp Pro Pro Pro Glu Gly
                    290                 295                 300

Ala Phe Val Gly Phe Val Leu Ser Arg Lys Glu Pro Met Trp Ala Asp
305                 310                 315                 320

Leu Leu Ala Leu Ala Ala Ala Arg Gly Gly Arg Val His Arg Ala Pro
                    325                 330                 335

Glu Pro Tyr Lys Ala Leu Arg Asp Leu Lys Glu Ala Arg Gly Leu Leu
                    340                 345                 350

Ala Lys Asp Leu Ser Val Leu Ala Leu Arg Glu Gly Leu Gly Leu Pro
                    355                 360                 365

Pro Gly Asp Asp Pro Met Val Leu Ala Tyr Leu Leu Asp Pro Ser Asn
                    370                 375                 380

Thr Thr Pro Glu Gly Val Ala Arg Arg Tyr Gly Gly Glu Trp Thr Glu
385                 390                 395                 400

Glu Ala Gly Glu Arg Ala Ala Leu Ser Glu Arg Leu Phe Ala Asn Leu
                    405                 410                 415

Trp Gly Arg Leu Glu Gly Glu Glu Arg Leu Leu Trp Leu Tyr Arg Glu
                    420                 425                 430

Val Glu Arg Pro Leu Ser Ala Val Leu Ala His Met Glu Ala Thr Gly
                    435                 440                 445

Val Arg Leu Asp Val Ala Tyr Leu Arg Ala Leu Ser Leu Glu Val Ala
                    450                 455                 460

Glu Glu Ile Ala Arg Leu Glu Ala Glu Val Phe Arg Leu Ala Gly His
465                 470                 475                 480

Pro Phe Asn Leu Asn Ser Arg Asp Gln Leu Glu Arg Val Leu Phe Asp
                    485                 490                 495

Glu Leu Gly Leu Pro Ala Ile Gly Lys Thr Lys Arg Thr Gly Lys Arg
                    500                 505                 510

Ser Thr Ser Ala Ala Val Leu Glu Ala Leu Arg Glu Ala His Pro Ile
                    515                 520                 525

Val Glu Lys Ile Leu Gln Tyr Arg Glu Leu Thr Lys Leu Lys Ser Thr
                    530                 535                 540

Tyr Ile Asp Pro Leu Pro Asp Leu Ile His Pro Arg Thr Gly Arg Leu
545                 550                 555                 560

His Thr Arg Phe Asn Gln Thr Ala Thr Ala Thr Gly Arg Leu Ser Ser
                    565                 570                 575
```

```
Ser Asp Pro Asn Leu Gln Asn Ile Pro Val Arg Thr Pro Leu Gly Gln
            580                 585                 590

Arg Ile Arg Arg Ala Phe Ile Ala Glu Glu Gly Trp Leu Leu Val Ala
        595                 600                 605

Leu Asp Tyr Ser Gln Ile Glu Leu Arg Val Leu Ala His Leu Ser Gly
    610                 615                 620

Asp Glu Asn Leu Ile Arg Val Phe Gln Glu Gly Arg Asp Ile His Thr
625                 630                 635                 640

Glu Thr Ala Ser Trp Met Phe Gly Val Pro Arg Glu Ala Val Asp Pro
                645                 650                 655

Leu Met Arg Arg Ala Ala Lys Thr Ile Asn Phe Gly Val Leu Tyr Gly
                    660                 665                 670

Met Ser Ala His Arg Leu Ser Gln Glu Leu Ala Ile Pro Tyr Glu Glu
                675                 680                 685

Ala Gln Ala Phe Ile Glu Arg Tyr Phe Gln Ser Phe Pro Lys Val Arg
        690                 695                 700

Ala Trp Ile Glu Lys Thr Leu Glu Glu Gly Arg Arg Arg Gly Tyr Val
705                 710                 715                 720

Glu Thr Leu Phe Gly Arg Arg Arg Tyr Val Pro Asp Leu Gly Ala Arg
                725                 730                 735

Val Lys Ser Val Arg Glu Ala Ala Glu Arg Met Ala Ile Asn Met Pro
                740                 745                 750

Val Gln Gly Thr Ala Ala Asp Leu Met Lys Leu Ala Met Val Lys Leu
            755                 760                 765

Phe Pro Arg Leu Glu Glu Met Gly Ala Arg Met Leu Leu Gln Val His
    770                 775                 780

Asp Glu Leu Val Leu Glu Ala Pro Lys Glu Arg Ala Glu Ala Val Ala
785                 790                 795                 800

Arg Leu Ala Lys Glu Val Met Glu Gly Val Tyr Pro Leu Ala Val Pro
                805                 810                 815

Leu Glu Val Glu Val Gly Ile Gly Glu Asp Trp Leu Ser Ala Lys Glu
                820                 825                 830

<210> SEQ ID NO 35
<211> LENGTH: 2499
<212> TYPE: DNA
<213> ORGANISM: Thermus aquaticus

<400> SEQUENCE: 35
atgcgtggca tgcttcctct ttttgagccc aagggccggg tcctcctggt ggacggccac      60
cacctggcct accgcacctt ccacgccctg aagggcctca ccaccagccg gggggagccg     120
gtgcaggcgg tctacggctt cgccaagagc ctcctcaagg ccctcaagga ggactgggac     180
gcggtgatcg tggtctttga cgccaaggcc cctccttcc gccacgaggc ctacggggg      240 tacaaggcgg ccgggccccc cacgccggag actttcccc ggcaactcgc cctcatcaag     300
gagctggtgg acctcctggg gctggcgcgc ctcgaggtcc cgggctacga ggcggacgac     360
gtcctggcca gcctggccaa gaaggcggaa aaggagggct acgaggtccg catcctcacc     420
gccgacaaag acctttacca gctccttccc gaccgcatcc acatcctcca ccccgagggg     480
tacctcatca cccggcctg gctttgggaa agtacggcc tgaggcccga ccagtgggcc      540
gactaccggg ccctgaccgg ggacgagtcc gacaaccttc ccgggtcaa gggcatcggg     600 gagaagacgg cgaggaagct tctggaggag tgggggagcc tggaagccct cctcaagaac     660
```

|   |   |
|---|---|
| ctggaccggc tgaagcccgc catccgggag aagatcctgg cccacatgga cgatctgaag | 720 |
| ctctcctggg acatggccaa ggtgcgcacc gacctgcccc tggaggtgga cttcgccaaa | 780 |
| aggcgggagc ccgaccggga gaggcttagg gcctttctgg agaggcttga gtttggcagc | 840 |
| ctcctccacg agttcggcct tctggaaagc cccaaggccc tggaggaggc cccctggccc | 900 |
| ccgccggaag gggccttcgt gggctttgtg ctttcccgca aggagcccat gtgggccgat | 960 |
| cttctggccc tggccgccgc caggggggc cgggtccacc gggcccccga gccttataaa | 1020 |
| gccctcaggg acctgaagga ggcgcggggg cttctcgcca aagacctgag cgttctggcc | 1080 |
| ctgagggaag gccttggcct cccgcccggc gacgaccca tggtcctcgc ctacctcctg | 1140 |
| gaccccttcca acaccacccc cgagggggtg gcccggcgct acggcgggga gtggacggag | 1200 |
| gaggcggggg agcgggccgc cctttccgag aggctcttcg ccaacctgtg ggggaggctt | 1260 |
| gagggggagg agaggctcct ttggctttac cgggaggtgg agaggcccct ttccgctgtc | 1320 |
| ctggcccaca tggaggccac gggggtgcgc ctggacgtgg cctatctcag ggccttgtcc | 1380 |
| ctggaggtgg ccgaggagat cgcccgcctc gaggccgagg tcttccgcct ggccggccac | 1440 |
| cccttcaacc tcaactcccg ggaccagctg gaaagggtcc tctttgacga gctagggctt | 1500 |
| cccgccatcg gcaagacgaa gaggaccggc aagcgctcca ccagcgccgc cgtcctggag | 1560 |
| gccctccgcg aggcccaccc catcgtggag aagatcctgc agtaccggga gctcaccaag | 1620 |
| ctgaagagca cctacattga ccccttgccg gacctcatcc accccaggac gggccgcctc | 1680 |
| cacacccgct tcaaccagac ggccacggcc acgggcaggc taagtagctc cgatcccaac | 1740 |
| ctccagaaca tccccgtccg caccccgctt gggcagagga tccgccgggc cttcatcgcc | 1800 |
| gaggagggt ggctattggt ggccctggac tataccaga tagagctcag ggtgctggcc | 1860 |
| cacctctccg cgacgagaa cctgatccgg gtcttccagg aggggcggga catccacacg | 1920 |
| gagaccgcca gctggatgtt cggcgtcccc cgggaggccg tggacccct gatgcgccgg | 1980 |
| gcggccaaga ccatcaactt cggggtcctc tacggcatgt cggcccaccg cctctcccag | 2040 |
| gagctagcca tcccttacga ggaggcccag gccttcattg agcgctactt tcagagcttc | 2100 |
| cccaaggtgc gggcctggat tgagaagacc ctggaggagg caggaggcg ggggtacgtg | 2160 |
| gagaccctct tcggccgccg ccgctacgtg ccagacctag ggcccgggt gaagagcgtg | 2220 |
| cgggaggcgg ccgagcgcat ggccatcaac atgcccgtcc agggcaccgc cgccgacctc | 2280 |
| atgaagctgg ctatggtgaa gctcttcccc aggctggagg aaatgggggc caggatgctc | 2340 |
| cttcaggtcc acgacgagct ggtcctcgag gccccaaaag agagggcgga ggccgtggcc | 2400 |
| cggctggcca aggaggtcat ggaggggtg tatcccctgg ccgtgccct ggaggtggag | 2460 |
| gtggggatag gggaggactg gctctccgcc aaggagtaa | 2499 |

<210> SEQ ID NO 36
<211> LENGTH: 832
<212> TYPE: PRT
<213> ORGANISM: Thermus aquaticus

<400> SEQUENCE: 36

Met Arg Gly Met Leu Pro Leu Phe Glu Pro Lys Gly Arg Val Leu Leu
1               5                   10                  15

Val Asp Gly His His Leu Ala Tyr Arg Thr Phe His Ala Leu Lys Gly
                20                  25                  30

Leu Thr Thr Ser Arg Gly Glu Pro Val Gln Ala Val Tyr Gly Phe Ala
        35                  40                  45

-continued

```
Lys Ser Leu Leu Lys Ala Leu Lys Glu Asp Trp Asp Ala Val Ile Val
     50                  55                  60
Val Phe Asp Ala Lys Ala Pro Ser Phe Arg His Glu Ala Tyr Gly Gly
 65                  70                  75                  80
Tyr Lys Ala Gly Arg Ala Pro Thr Pro Glu Asp Phe Pro Arg Gln Leu
                 85                  90                  95
Ala Leu Ile Lys Glu Leu Val Asp Leu Gly Leu Ala Arg Leu Glu
            100                 105                 110
Val Pro Gly Tyr Glu Ala Asp Asp Val Leu Ala Ser Leu Ala Lys Lys
            115                 120                 125
Ala Glu Lys Glu Gly Tyr Glu Val Arg Ile Leu Thr Ala Asp Lys Asp
    130                 135                 140
Leu Tyr Gln Leu Leu Ser Asp Arg Ile His Val Leu His Pro Glu Gly
145                 150                 155                 160
Tyr Leu Ile Thr Pro Ala Trp Leu Trp Glu Lys Tyr Gly Leu Arg Pro
                165                 170                 175
Asp Gln Trp Ala Asp Tyr Arg Ala Leu Thr Gly Asp Glu Ser Asp Asn
            180                 185                 190
Leu Pro Gly Val Lys Gly Ile Gly Glu Lys Thr Ala Arg Lys Leu Leu
            195                 200                 205
Glu Glu Trp Gly Ser Leu Glu Ala Leu Leu Lys Asn Leu Asp Arg Leu
    210                 215                 220
Lys Pro Ala Ile Arg Glu Lys Ile Leu Ala His Met Asp Asp Leu Lys
225                 230                 235                 240
Leu Ser Trp Asp Met Ala Lys Val Arg Thr Asp Leu Pro Leu Glu Val
                245                 250                 255
Asp Phe Ala Lys Arg Arg Glu Pro Asp Arg Glu Arg Leu Arg Ala Phe
            260                 265                 270
Leu Glu Arg Leu Glu Phe Gly Ser Leu Leu His Glu Phe Gly Leu Leu
    275                 280                 285
Glu Ser Pro Lys Ala Leu Glu Glu Ala Pro Trp Pro Pro Pro Glu Gly
    290                 295                 300
Ala Phe Val Gly Phe Val Leu Ser Arg Lys Glu Pro Met Trp Ala Asp
305                 310                 315                 320
Leu Leu Ala Leu Ala Ala Ala Arg Gly Gly Arg Val His Arg Ala Pro
                325                 330                 335
Glu Pro Tyr Lys Ala Leu Arg Asp Leu Lys Glu Ala Arg Gly Leu Leu
            340                 345                 350
Ala Lys Asp Leu Ser Val Leu Ala Leu Arg Glu Gly Leu Gly Leu Pro
    355                 360                 365
Pro Gly Asp Asp Pro Met Val Leu Ala Tyr Leu Leu Asp Pro Ser Asn
370                 375                 380
Thr Thr Pro Glu Gly Val Ala Arg Arg Tyr Gly Gly Glu Trp Thr Glu
385                 390                 395                 400
Glu Ala Gly Glu Arg Ala Ala Leu Ser Glu Arg Leu Phe Ala Asn Leu
                405                 410                 415
Trp Gly Arg Leu Glu Gly Glu Glu Arg Leu Leu Trp Leu Tyr Arg Glu
            420                 425                 430
Val Glu Arg Pro Leu Ser Ala Val Leu Ala His Met Glu Ala Thr Gly
    435                 440                 445
Val Arg Leu Asp Val Ala Tyr Leu Arg Ala Leu Ser Leu Glu Val Ala
    450                 455                 460
Glu Glu Ile Ala Arg Leu Glu Ala Glu Val Phe Arg Leu Ala Gly His
```

```
465                 470                 475                 480
Pro Phe Asn Leu Asn Ser Arg Asp Gln Leu Glu Arg Val Leu Phe Asp
                485                 490                 495
Glu Leu Gly Leu Pro Ala Ile Gly Lys Thr Lys Arg Thr Gly Lys Arg
            500                 505                 510
Ser Thr Ser Ala Ala Val Leu Glu Ala Leu Arg Glu Ala His Pro Ile
        515                 520                 525
Val Glu Lys Ile Leu Gln Tyr Arg Glu Leu Thr Lys Leu Lys Ser Thr
    530                 535                 540
Tyr Ile Asp Pro Leu Pro Asp Leu Ile His Pro Arg Thr Gly Arg Leu
545                 550                 555                 560
His Thr Arg Phe Asn Gln Thr Ala Thr Ala Thr Gly Arg Leu Ser Ser
                565                 570                 575
Ser Asp Pro Asn Leu Gln Asn Ile Pro Val Arg Thr Pro Leu Gly Gln
            580                 585                 590
Arg Ile Arg Arg Ala Phe Ile Ala Glu Glu Gly Trp Leu Leu Val Ala
        595                 600                 605
Leu Asp Tyr Ser Gln Ile Glu Leu Arg Val Leu Ala His Leu Ser Gly
    610                 615                 620
Asp Glu Asn Leu Ile Arg Val Phe Gln Glu Gly Arg Asp Ile His Thr
625                 630                 635                 640
Glu Thr Ala Ser Trp Met Phe Gly Val Pro Arg Glu Ala Val Asp Pro
                645                 650                 655
Leu Met Arg Arg Ala Ala Lys Thr Ile Asn Phe Gly Val Leu Tyr Gly
            660                 665                 670
Met Ser Ala His Arg Leu Ser Gln Glu Leu Ala Ile Pro Tyr Glu Glu
        675                 680                 685
Ala Gln Ala Phe Ile Glu Arg Tyr Phe Gln Ser Phe Pro Lys Val Arg
    690                 695                 700
Ala Trp Ile Glu Lys Thr Leu Glu Glu Gly Arg Arg Arg Gly Tyr Val
705                 710                 715                 720
Glu Thr Leu Phe Gly Arg Arg Arg Tyr Val Pro Asp Leu Gly Ala Arg
                725                 730                 735
Val Lys Ser Val Arg Glu Ala Ala Glu Arg Met Ala Ile Asn Met Pro
            740                 745                 750
Val Gln Gly Thr Ala Ala Asp Leu Met Lys Leu Ala Met Val Lys Leu
        755                 760                 765
Phe Pro Arg Leu Glu Glu Met Gly Ala Arg Met Leu Leu Gln Val His
    770                 775                 780
Asp Glu Leu Val Leu Glu Ala Pro Lys Glu Arg Ala Glu Ala Val Ala
785                 790                 795                 800
Arg Leu Ala Lys Glu Val Met Glu Gly Val Tyr Pro Leu Ala Val Pro
                805                 810                 815
Leu Glu Val Glu Val Gly Ile Gly Glu Asp Trp Leu Ser Ala Lys Glu
            820                 825                 830

<210> SEQ ID NO 37
<211> LENGTH: 2499
<212> TYPE: DNA
<213> ORGANISM: Thermus aquaticus

<400> SEQUENCE: 37
atgcgtggca tgcttcctct ttttgagccc aagggccggg tcctcctggt ggacggccac      60
cacctggcct accgcacctt ccacgccctg aagggcctca ccaccagccg gggggagccg     120
```

```
gtgcaggcgg tctacggctt cgccaagagc ctcctcaagg ccctcaagga ggactgggac    180
gcggtgatcg tggtctttga cgccaaggcc ccctccttcc gccacgaggc ctacgggggg    240
tacaaggcgg gccgggcccc cacgccggag gactttcccc ggcaactcgc cctcatcaag    300
gagctggtgg acctcctggg gctggcgcgc ctcgaggtcc cgggctacga ggcggacgac    360
gtcctggcca gcctggccaa gaaggcggaa aaggagggct acgaggtccg catcctcacc    420
gccgacaaag acctttacca gctcctttcc gaccgcatcc acgtcctcca ccccgagggg    480
tacctcatca ccccggcctg gctttgggaa aagtacggcc tgaggcccga ccagtgggcc    540
gactaccggg ccctgaccgg ggacgagtcc gacaaccttc cgggggtcaa gggcatcggg    600
gagaagacgg cgaggaagct tctggaggag tgggggagcc tggaagccct cctcaagaac    660
ctggaccggg tgaagcccgc catccgggag aagatcctgg cccacatgga cgatctgaag    720
ctctcctggg acatggccaa ggtgcgcacc gacctgcccc tggaggtgga cttcgccaaa    780
aggcgggagc ccgaccggga gaggcttagg gcctttctgg agaggcttga gtttggcagc    840
ctcctccacg agttcggcct tctggaaagc cccaaggccc tggaggaggc cccctggccc    900
ccgccggaag gggccttcgt gggctttgtg ctttcccgca aggagcccat gtgggccgat    960
cttctggccc tggccgccgc caggggggggc cgggtccacc gggcccccga gccttataaa    1020
gccctcaggg acctgaagga ggcgcgggggg cttctcgcca aagacctgag cgttctggcc    1080
ctgagggaag gccttggcct cccgcccggc gacgacccca tggtcctcgc ctacctcctg    1140
gacccttcca acaccacccc cgaggggggtg gcccggcgct acgggcgggga gtggacggag    1200 gaggcggggg agcgggccgc cctttccgag aggctcttcg ccaacctgtg ggggaggctt    1260
gagggggagg agaggctcct ttggctttac cgggaggtgg agaggcccct ttccgctgtc    1320
ctggcccaca tggaggccac ggggggtgcgc ctggacgtgg cctatctcag ggccttgtcc    1380
ctggaggtgg ccgaggagat cgcccgcctc gaggccgagg tcttccgcct ggccggccac    1440
cccttcaacc tcaactcccg ggaccagctg gaaagggtcc tctttgacga gctagggctt    1500
cccgccatcg gcaagacgaa gaggaccggc aagcgctcca ccagcgccgc cgtcctggag    1560
gccctccgcg aggcccaccc catcgtggag aagatcctgc agtaccggga gctcaccaag    1620
ctgaagagca cctacattga ccccttgccg gacctcatcc accccaggac gggccgcctc    1680
cacacccgct tcaaccagac ggccacggcc acgggcaggg taagtagctc cgatcccaac    1740
ctccagaaca tccccgtccg caccccgctt gggcagagga tccgccgggc cttcatcgcc    1800
gaggaggggt ggctattggt ggccctggac tatagccaga tagagctcag ggtgctggcc    1860
cacctctccg gcgacgagaa cctgatccgg gtcttccagg aggggcggga catccacacg    1920
gagaccgcca gctggatgtt cggcgtcccc cgggaggccg tggacccccct gatgcgccgg    1980 gcggccaaga ccatcaactt cggggtcctc tacggcatgt cggcccaccg cctctcccag    2040
gagctagcca tcccttacga ggaggcccag gccttcattg agcgctactt tcagagcttc    2100
cccaaggtgc gggcctggat tgagaagacc ctggaggagg gcaggaggcg ggggtacgtg    2160
gagaccctct tcggccgccg ccgctacgtg ccagacctag ggccccgggt gaagagcgtg    2220
cgggaggcgg ccgagcgcat ggccatcaac atgcccgtcc agggcaccgc cgccgacctc    2280
atgaagctgg ctatggtgaa gctcttcccc aggctggagg aaatggggggc caggatgctc    2340 cttcaggtcc acgacgagct ggtcctcgag gccccaaaag agagggcgga ggccgtggcc    2400
cggctggcca aggaggtcat ggagggggtg tatcccctgg ccgtgccccct ggaggtggag    2460
```
gtggggatag gggaggactg gctctccgcc aaggagtaa 2499

<210> SEQ ID NO 38
<211> LENGTH: 832
<212> TYPE: PRT
<213> ORGANISM: Thermus aquaticus

<400> SEQUENCE: 38

| | | | | | | | | | | | | | | | |
|---|---|---|---|---|---|---|---|---|---|---|---|---|---|---|---|
| Met | Arg | Gly | Met | Leu | Pro | Leu | Phe | Glu | Pro | Lys | Gly | Arg | Val | Leu | Leu |
| 1 | | | | 5 | | | | | 10 | | | | | 15 | |
| Val | Asp | Gly | His | His | Leu | Ala | Tyr | Arg | Thr | Phe | His | Ala | Leu | Lys | Gly |
| | | | 20 | | | | | 25 | | | | | 30 | | |
| Leu | Thr | Thr | Ser | Arg | Gly | Glu | Pro | Val | Gln | Ala | Val | Tyr | Gly | Phe | Ala |
| | | 35 | | | | | 40 | | | | | 45 | | | |
| Lys | Ser | Leu | Leu | Lys | Ala | Leu | Lys | Glu | Asp | Trp | Asp | Ala | Val | Ile | Val |
| 50 | | | | | 55 | | | | | 60 | | | | | |
| Val | Phe | Asp | Ala | Lys | Ala | Pro | Ser | Phe | Arg | His | Glu | Ala | Tyr | Gly | Gly |
| 65 | | | | | 70 | | | | | 75 | | | | | 80 |
| Tyr | Lys | Ala | Gly | Arg | Ala | Pro | Thr | Pro | Glu | Asp | Phe | Pro | Arg | Gln | Leu |
| | | | | 85 | | | | | 90 | | | | | 95 | |
| Ala | Leu | Ile | Lys | Glu | Leu | Val | Asp | Leu | Leu | Gly | Leu | Ala | Arg | Leu | Glu |
| | | | 100 | | | | | 105 | | | | | 110 | | |
| Val | Pro | Gly | Tyr | Glu | Ala | Asp | Asp | Val | Leu | Ala | Ser | Leu | Ala | Lys | Lys |
| | | | 115 | | | | | 120 | | | | | 125 | | |
| Ala | Glu | Lys | Glu | Gly | Tyr | Glu | Val | Arg | Ile | Leu | Thr | Ala | Asp | Lys | Asp |
| | 130 | | | | | 135 | | | | | 140 | | | | |
| Leu | Tyr | Gln | Leu | Leu | Ser | Asp | Arg | Ile | His | Ile | Leu | His | Pro | Glu | Gly |
| 145 | | | | | 150 | | | | | 155 | | | | | 160 |
| Tyr | Leu | Ile | Thr | Pro | Ala | Trp | Leu | Trp | Glu | Lys | Tyr | Gly | Leu | Arg | Pro |
| | | | | 165 | | | | | 170 | | | | | 175 | |
| Asp | Gln | Trp | Ala | Asp | Tyr | Arg | Ala | Leu | Thr | Gly | Asp | Glu | Ser | Asp | Asn |
| | | | 180 | | | | | 185 | | | | | 190 | | |
| Leu | Pro | Gly | Val | Lys | Gly | Ile | Gly | Glu | Lys | Thr | Ala | Arg | Lys | Leu | Leu |
| | | 195 | | | | | 200 | | | | | 205 | | | |
| Glu | Glu | Trp | Gly | Ser | Leu | Glu | Ala | Leu | Leu | Lys | Asn | Leu | Asp | Arg | Leu |
| | 210 | | | | | 215 | | | | | 220 | | | | |
| Lys | Pro | Ala | Ile | Arg | Glu | Lys | Ile | Leu | Ala | His | Met | Asp | Asp | Leu | Lys |
| 225 | | | | | 230 | | | | | 235 | | | | | 240 |
| Leu | Ser | Trp | Asp | Met | Ala | Lys | Val | Arg | Thr | Asp | Leu | Pro | Leu | Glu | Val |
| | | | | 245 | | | | | 250 | | | | | 255 | |
| Asp | Phe | Ala | Lys | Arg | Arg | Glu | Pro | Asp | Arg | Glu | Arg | Leu | Arg | Ala | Phe |
| | | | 260 | | | | | 265 | | | | | 270 | | |
| Leu | Glu | Arg | Leu | Glu | Phe | Gly | Ser | Leu | Leu | His | Glu | Phe | Gly | Leu | Leu |
| | | | 275 | | | | | 280 | | | | | 285 | | |
| Glu | Ser | Pro | Lys | Ala | Leu | Glu | Glu | Ala | Pro | Trp | Pro | Pro | Pro | Glu | Gly |
| | 290 | | | | | 295 | | | | | 300 | | | | |
| Ala | Phe | Val | Gly | Phe | Val | Leu | Ser | Arg | Lys | Glu | Pro | Met | Trp | Ala | Asp |
| 305 | | | | | 310 | | | | | 315 | | | | | 320 |
| Leu | Leu | Ala | Leu | Ala | Ala | Ala | Arg | Gly | Gly | Arg | Val | His | Arg | Ala | Pro |
| | | | | 325 | | | | | 330 | | | | | 335 | |
| Glu | Pro | Tyr | Lys | Ala | Leu | Arg | Asp | Leu | Lys | Glu | Ala | Arg | Gly | Leu | Leu |
| | | | 340 | | | | | 345 | | | | | 350 | | |
| Ala | Lys | Asp | Leu | Ser | Val | Leu | Ala | Leu | Arg | Glu | Gly | Leu | Gly | Leu | Pro |
| | | | 355 | | | | | 360 | | | | | 365 | | |

```
Pro Gly Asp Asp Pro Met Val Leu Ala Tyr Leu Leu Asp Pro Ser Asn
    370                 375                 380

Thr Thr Pro Glu Gly Val Ala Arg Arg Tyr Gly Gly Glu Trp Thr Glu
385                 390                 395                 400

Glu Ala Gly Glu Arg Ala Ala Leu Ser Glu Arg Leu Phe Ala Asn Leu
                405                 410                 415

Trp Gly Arg Leu Glu Gly Glu Arg Leu Leu Trp Leu Tyr Arg Glu
                420                 425                 430

Val Glu Arg Pro Leu Ser Ala Val Leu Ala His Met Glu Ala Thr Gly
            435                 440                 445

Val Arg Leu Asp Val Ala Tyr Leu Arg Ala Leu Ser Leu Glu Val Ala
450                 455                 460

Glu Glu Ile Ala Arg Leu Glu Ala Glu Val Phe Arg Leu Ala Gly His
465                 470                 475                 480

Pro Phe Asn Leu Asn Ser Arg Asp Gln Leu Glu Arg Val Leu Phe Asp
                485                 490                 495

Glu Leu Gly Leu Pro Ala Ile Gly Lys Thr Lys Lys Thr Gly Lys Arg
                500                 505                 510

Ser Thr Ser Ala Ala Val Leu Glu Ala Leu Arg Glu Ala His Pro Ile
            515                 520                 525

Val Glu Lys Ile Leu Gln Tyr Arg Glu Leu Thr Lys Leu Lys Ser Thr
530                 535                 540

Tyr Ile Asp Pro Leu Pro Asp Leu Ile His Pro Arg Thr Gly Arg Leu
545                 550                 555                 560

His Thr Arg Phe Asn Gln Thr Ala Thr Ala Thr Gly Arg Leu Ser Ser
                565                 570                 575

Ser Asp Pro Asn Leu Gln Asn Ile Pro Val Arg Thr Pro Leu Gly Gln
            580                 585                 590

Arg Ile Arg Arg Ala Phe Ile Ala Glu Glu Gly Trp Leu Leu Val Ala
            595                 600                 605

Leu Asp Tyr Ser Gln Ile Glu Leu Arg Val Leu Ala His Leu Ser Gly
        610                 615                 620

Asp Glu Asn Leu Ile Arg Val Phe Gln Glu Gly Arg Asp Ile His Thr
625                 630                 635                 640

Glu Thr Ala Ser Trp Met Phe Gly Val Pro Arg Glu Ala Val Asp Pro
                645                 650                 655

Leu Met Arg Arg Ala Ala Lys Thr Ile Asn Phe Gly Val Leu Tyr Gly
                660                 665                 670

Met Ser Ala His Arg Leu Ser Gln Glu Leu Ala Ile Pro Tyr Glu Glu
            675                 680                 685

Ala Gln Ala Phe Ile Glu Arg Tyr Phe Gln Ser Phe Pro Lys Val Arg
        690                 695                 700

Ala Trp Ile Glu Lys Thr Leu Glu Glu Gly Arg Arg Arg Gly Tyr Val
705                 710                 715                 720

Glu Thr Leu Phe Gly Arg Arg Arg Tyr Val Pro Asp Leu Gly Ala Arg
                725                 730                 735

Val Lys Ser Val Arg Glu Ala Ala Glu Arg Met Ala Ile Asn Met Pro
            740                 745                 750

Val Gln Gly Thr Ala Ala Asp Leu Met Lys Leu Ala Met Val Lys Leu
        755                 760                 765

Phe Pro Arg Leu Glu Glu Met Gly Ala Arg Met Leu Leu Gln Val His
770                 775                 780

Asp Glu Leu Val Leu Glu Ala Pro Lys Glu Arg Ala Glu Ala Val Ala
```

| | | | |
|---|---|---|---|
| Arg Leu Ala Lys Glu Val Met Glu Gly Val Tyr Pro Leu Ala Val Pro | | | |
| 785 | 790 | 795 | 800 |

Leu Glu Val Glu Val Gly Ile Gly Glu Asp Trp Leu Ser Ala Lys Glu
                    820                   825                   830

<210> SEQ ID NO 39
<211> LENGTH: 2499
<212> TYPE: DNA
<213> ORGANISM: Thermus aquaticus

<400> SEQUENCE: 39

| | |
|---|---|
| atgcgtggca tgcttcctct ttttgagccc aagggccggg tcctcctggt ggacggccac | 60 |
| cacctggcct accgcacctt ccacgccctg aagggcctca ccaccagccg ggggagccg | 120 |
| gtgcaggcgg tctacggctt cgccaagagc ctcctcaagg ccctcaagga ggactgggac | 180 |
| gcggtgatcg tggtctttga cgccaaggcc cctccttcc gccacgaggc ctacggggg | 240 |
| tacaaggcgg gccgggcccc cacgccggag gactttcccc ggcaactcgc cctcatcaag | 300 |
| gagctggtgg acctcctggg gctggcgcgc ctcgaggtcc cgggctacga ggcggacgac | 360 |
| gtcctggcca gctggccaa gaaggcgaa aaggagggct acgaggtccg catcctcacc | 420 |
| gccgacaaag acctttacca gctcctttcc gaccgcatcc acatcctcca ccccgagggg | 480 |
| tacctcatca ccccggcctg gctttgggaa agtacggcc tgaggcccga ccagtgggcc | 540 |
| gactaccggg ccctgaccgg ggacgagtcc gacaaccttc cgggggtcaa gggcatcggg | 600 |
| gagaagacgc gaggaagct tctggaggag tgggggagcc tggaagccct cctcaagaac | 660 |
| ctggaccggc tgaagcccgc catccggag aagatcctgg cccacatgga cgatctgaag | 720 |
| ctctcctggg acatggccaa ggtgcgcacc gacctgcccc tggaggtgga cttcgccaaa | 780 |
| aggcgggagc ccgaccggga gaggcttagg ccttttctgg agaggcttga gtttggcagc | 840 |
| ctcctccacg agttcggcct tctggaaagc cccaaggccc tggaggaggc ccctggccc | 900 |
| ccgccggaag ggccttcgt gggctttgtg ctttcccgca aggagcccat gtgggccgat | 960 |
| cttctggccc tggccgccgc cagggggggc cgggtccacc gggcccccga gccttataaa | 1020 |
| gccctcaggg acctgaagga ggcgcgggg cttctcgcca aagacctgag cgttctggcc | 1080 |
| ctgaggaag gccttggcct cccgcccggc gacgacccca tggtcctcgc ctacctcctg | 1140 |
| gacccttcca cacaccaccc cgaggggtgc gccggcgct acggcgggga gtggacggag | 1200 |
| gaggcgggg agcgggccgc cctttccgag aggctcttcg ccaacctgtg ggggaggctt | 1260 |
| gaggggagg agaggctcct ttggctttac cgggaggtgg agaggcccct ttccgctgtc | 1320 |
| ctggcccaca tggaggccac ggggtgcgc ctggacgtgg cctatctcag ggccttgtcc | 1380 |
| ctggaggtgg ccgaggagat cgcccgcctc gaggccgagg tcttccgcct ggccggccac | 1440 |
| cccttcaacc tcaactcccg ggaccagctg gaaagggtcc tctttgacga gctagggctt | 1500 |
| cccgccatcg gcaagacgaa gaagaccggc aagcgctcca ccagcgccgc cgtcctggag | 1560 |
| gccctccgcg aggcccaccc catcgtggag aagatcctgc agtaccggga gctcaccaag | 1620 |
| ctgaagagca cctacattga ccccttgccg gacctcatcc accccaggac gggccgcctc | 1680 |
| cacacccgct tcaaccagac ggccacggcc acgggcaggc taagtagctc cgatcccaac | 1740 |
| ctccagaaca tccccgtccg caccccgctt gggcagagga tccgccgggc cttcatcgcc | 1800 |
| gaggaggggt ggctattggt ggccctggac tatagccaga tagagctcag ggtgctggcc | 1860 |
| cacctctccg gcgacgagaa cctgatccgg gtcttccagg aggggcggga catccacacg | 1920 |

-continued

```
gagaccgcca gctggatgtt cggcgtcccc cgggaggccg tggacccct  gatgcgccgg    1980 gcggccaaga ccatcaactt cggggtcctc tacggcatgt cggcccaccg cctctcccag    2040
gagctagcca tcccttacga ggaggcccag gccttcattg agcgctactt tcagagcttc    2100
cccaaggtgc gggcctggat tgagaagacc ctggaggagg gcaggaggcg ggggtacgtg    2160
gagaccctct tcggccgccg ccgctacgtg ccagacctag gggcccgggt gaagagcgtg    2220
cgggaggcgg ccgagcgcat ggccatcaac atgcccgtcc agggcaccgc cgccgacctc    2280
atgaagctgg ctatggtgaa gctcttcccc aggctggagg aaatgggggc caggatgctc    2340
cttcaggtcc acgacgagct ggtcctcgag gccccaaaag agagggcgga ggccgtggcc    2400
cggctggcca aggaggtcat ggaggggtg  tatccctgg  ccgtgcccct ggaggtggag    2460
gtggggatag gggaggactg gctctccgcc aaggagtaa                           2499
```

THERMOSTABLE TYPE-A DNA POLYMERASE MUTANTS WITH INCREASED POLYMERIZATION RATE AND RESISTANCE TO INHIBITORS

CROSS-REFERENCE TO RELATED APPLICATIONS

This application relies on and claims the benefit of the filing date of U.S. provisional patent application No. 61/230,275, filed 31 Jul. 2009, the entire disclosure of which is hereby incorporated herein in its entirety by reference.

BACKGROUND OF THE INVENTION

Field of the Invention

The present invention relates to the field of molecular biology. More specifically, the present invention relates to methods of performing Polymerase Chain Reactions (PCR) and to improved polymerases for performing PCR.

Description of Related Art

DNA polymerases are enzymes capable of catalyzing the replication of DNA and have become indispensable research tools in biotechnology. In particular, the thermostable DNA polymerase from *Thermus aquaticus*, Taq, is commonly used in PCR reactions. Cyclic polymerase-mediated reactions, such as PCR, have numerous applications in the fields of basic research, medical diagnostics, and forensics.

In a standard protocol, PCR is based on three repeated steps: denaturation of a DNA template, annealing of primers to the denatured DNA template, and extension of the primers with a polymerase to synthesize nucleic acids complementary to the template. The conditions under which these steps are performed are well established in the art.

One important characteristic of the thermostable DNA polymerase used in a PCR reaction is its polymerization rate. A fast polymerase is desirable because it allows for shorter extension cycle times, resulting in production of amplification products in a shorter period of time than a slower polymerase. An amplification run thus may be shortened, allowing more efficient use of researchers' time, higher throughput on cost-limiting PCR equipment, and rapid medical diagnostic applications. Polymerization rate, or the number of nucleotides incorporated per unit time (under specified reaction conditions including temperature, pH, ionic strength, etc.), is influenced by a number of parameters including binding affinity for substrates (dNTPs, primed DNA) and catalytic efficiency (rate of nucleotidyl transfer, pyrophosphate release, and translocation steps). Processivity, or the number of nucleotides incorporated per binding event, is largely influenced by the affinity of polymerase for template. Polymerases with increased polymerization rate or increased processivity provide several benefits to PCR, including the ability to use faster cycling times.

Attempts to increase processivity of DNA polymerase used in PCR have included the use of fusion proteins containing DNA polymerase activity. For example, DNA polymerases have been fused to a domain for binding known processivity factors, such as thioredoxin or an Archaeal proliferating cell nuclear antigen. DNA polymerases have also been fused to multiple helix-hairpin-helix motifs identified in DNA topoisomerase V and to a sequence non-specific dsDNA binding protein.

Another strategy to improve PCR performance under fast cycling conditions is to mutate the polymerase. In this case, other characteristics of the enzyme may be reduced or eliminated, such as the 5'-3' exonuclease activity (see, for example, U.S. Pat. No. 5,474,920).

Another desirable characteristic of a DNA polymerase to be used in PCR reactions is its ability to work in complex or "dirty" environments. The ability of a DNA polymerase to polymerize in these kinds of samples significantly increases the applicability of the polymerase. Complex biological samples such as blood, cell lysates, plants and plant extracts, environmental samples, etc. have many components that can inhibit DNA polymerases used in PCR reactions. These components include hemoglobin, immunoglobulin G, lactoferrin, and perhaps protease activity in blood. Soil sample components that interfere with PCR reactions include humic acid, fulvic acid, plant polysaccharides, and metal ions. Although various procedures have been developed to pre-treat samples before attempting PCR reactions, these steps are generally time-consuming, labor-intensive, and might not achieve the purification required for the subsequent PCR. In addition, precious nucleic acid can be lost from the sample before the PCR reaction step.

Strategies to improve PCR reactions using complex samples without pre-treatment include the addition of substances to the PCR reaction, which can reduce the effect of PCR inhibitors found in the sample. For example, the addition of bovine serum albumin or the addition of single-stranded DNA binding T4 gene 32 protein to a PCR reaction mixture is known to enhance the amplification capacities of some DNA polymerases.

As with strategies that have been used to develop DNA polymerases with increased processivity, one strategy to improve the ability of DNA polymerases to perform PCR reactions in complex samples involves mutating the DNA polymerase itself. For example, it is known that N-terminal deletions of Taq DNA polymerase and/or mutations of certain amino acids can confer enhanced resistance to various inhibitors of PCR reactions. However, very few mutant DNA polymerases suitable for use in "dirty" PCR reactions have been reported.

SUMMARY OF THE INVENTION

The inventors have recognized that a need exists in the art for improved polymerase enzymes, including those used in PCR. More specifically, they have recognized that there is a need for genetically engineered polymerases that amplify target nucleic acids more rapidly than the wild-type enzymes from which they are created, and for genetically engineered polymerases that are capable of functioning at a relatively high level in the presence of substances that typically inhibit the polymerization activity of wild-type polymerase enzymes. The recognition of these needs has resulted in the development of newly engineered DNA polymerases that address the shortcomings of polymerases known in the art.

The present invention addresses this now recognized need in the art by providing engineered (also referred to herein as "genetically engineered" or "mutant") DNA polymerases, many of which are suitable for use in PCR reactions, that are able to polymerize a nucleic acid molecule that is complementary to a template nucleic acid, where the polymerization rate of the engineered polymerases is greater than the wild-type polymerases from which the engineered polymerases are derived and wherein the engineered polymerases are resistant to inhibitors that affect the polymerization activity of the wild-type enzyme. According to some embodiments of the invention, the engineered polymerases are mutants of thermostable Type-A DNA polymerases, where the mutants have a mutation at residue 507 of Taq DNA polymerase or at a residue in a DNA polymerase of another thermostable Type-A DNA polymerase that corresponds to residue 507 of Taq DNA polymerase, and an additional mutation at another residue that enhances the polymerization rate and/or resistance to inhibition. The additional mutation(s) are found at one or more of the following exemplary residues of Taq DNA polymerase (or corresponding residues of other thermostable Type-A DNA polymerases): 59, 155, 245, 375, 508, 734, and 749. It has been surprisingly found that a combination of mutations can provide an improvement in polymerase rate and/or resistance to polymerase activity inhibition, as compared to wild-type thermostable Type-A DNA polymerases. In embodiments where the mutant polymerase is a Taq DNA polymerase, it is preferred that the mutant not comprise an E507Q mutation or an E507K mutation as the sole mutation, as such an enzyme does not provide a suitable level of DNA polymerase activity under inhibitory conditions. Likewise, where the mutation is in another thermostable Type-A DNA polymerase at a residue corresponding to E507 of the Taq polymerase, it is preferred that the mutation not be a glutamic acid to glutamine (E to Q) or glutamic acid to lysine (E to K) mutation. As used herein, a Type-A DNA polymerase is a polymerase generally recognized in the art as having regions of sequence identity or similarity to polA (pol I) of *Escherichia coli*. Type-A DNA polymerases are recognized by the presence of three conserved motifs: A, B, and C. Motifs A and C are part of the catalytic site, whereas motif B is involved in the binding of dNTPs. Type-A DNA polymerases are widely known and recognized in the art as a structurally-related group of enzymes. Furthermore, a sub-set of Type-A DNA polymerases, the thermostable Type-A DNA polymerases, are likewise widely recognized as Type-A DNA polymerases that retain substantial activity when exposed to high temperatures, such as above 72° C.

Using the engineered DNA polymerases, the inventors have developed methods of polymerizing nucleic acids from template nucleic acids. In general, the methods comprise exposing (such as by combining together, etc.) an engineered DNA polymerase to (or with) a template DNA of interest and at least one primer suitable for priming polymerization of a nucleic acid that is complementary to one strand of the template DNA, and exposing (such as by subjecting) the polymerase, template, and primer(s) to conditions that are suitable for polymerization of a nucleic acid from the primer(s), based on the sequence of the template DNA. In some embodiments, two or more primers having different sequences are used. For example, in some embodiments two primers are used, where one primer specifically binds to one strand of the template DNA and the other binds to the other strand of the template DNA, allowing for production of a double-stranded polymerization product. In preferred embodiments, the method is a method of PCR.

The invention further provides compositions comprising an engineered DNA polymerase, such as compositions for polymerization of a template DNA. Also provided are nucleic acids encoding the engineered DNA polymerases, and compositions comprising them. Further, kits for sale or distribution of the engineered DNA polymerase or compositions comprising the engineered DNA polymerase, or for practice of a method according to the invention, are provided. Likewise, the invention provides for use of the engineered DNA polymerase or compositions comprising it in the polymerization of a nucleic acid, such as use in a PCR reaction.

BRIEF DESCRIPTION OF THE DRAWINGS

The accompanying drawings, which are incorporated in and constitute a part of this specification, provide data supporting embodiments of the invention, and together with the written description, serve to explain certain principles of the invention.

FIG. 1 shows an alignment of exemplary thermostable Type-A DNA polymerases that can be mutated to create an engineered DNA polymerase according to the invention.

FIG. 5 depicts Real-Time QPCR amplification plots and melt curves comparing the amplification of a 322 base-pair target by wild-type Taq DNA polymerase and two mutants according to the invention, in the presence of 10 ng of genomic DNA and in the absence of blood (Panels A and B, respectively), and in the presence of 4% (v/v) blood and the absence of genomic DNA (Panels C and D, respectively).

FIG. 6, Panels A-C, depict agarose gels, showing amplification products obtained from PCR amplification of a 286 base pair target (aldolase) in the absence of blood or in the presence of 2, 10, 15, 20, 25, 30, or 35% (v/v) blood (prepared using heparin according to standard blood collection and storage protocols), using exemplary mutant enzymes of the invention.

FIG. 7, Panels A-C, depict agarose gels, showing amplification products obtained from PCR amplification of a 286 base pair target (aldolase) in the absence of blood or in the presence of 2, 10, 15, 20, 25, 30, or 35% (v/v) blood (prepared using EDTA according to standard blood collection and storage protocols), using exemplary mutant enzymes of the invention.

DETAILED DESCRIPTION OF VARIOUS EMBODIMENTS OF THE INVENTION

Figure 2:
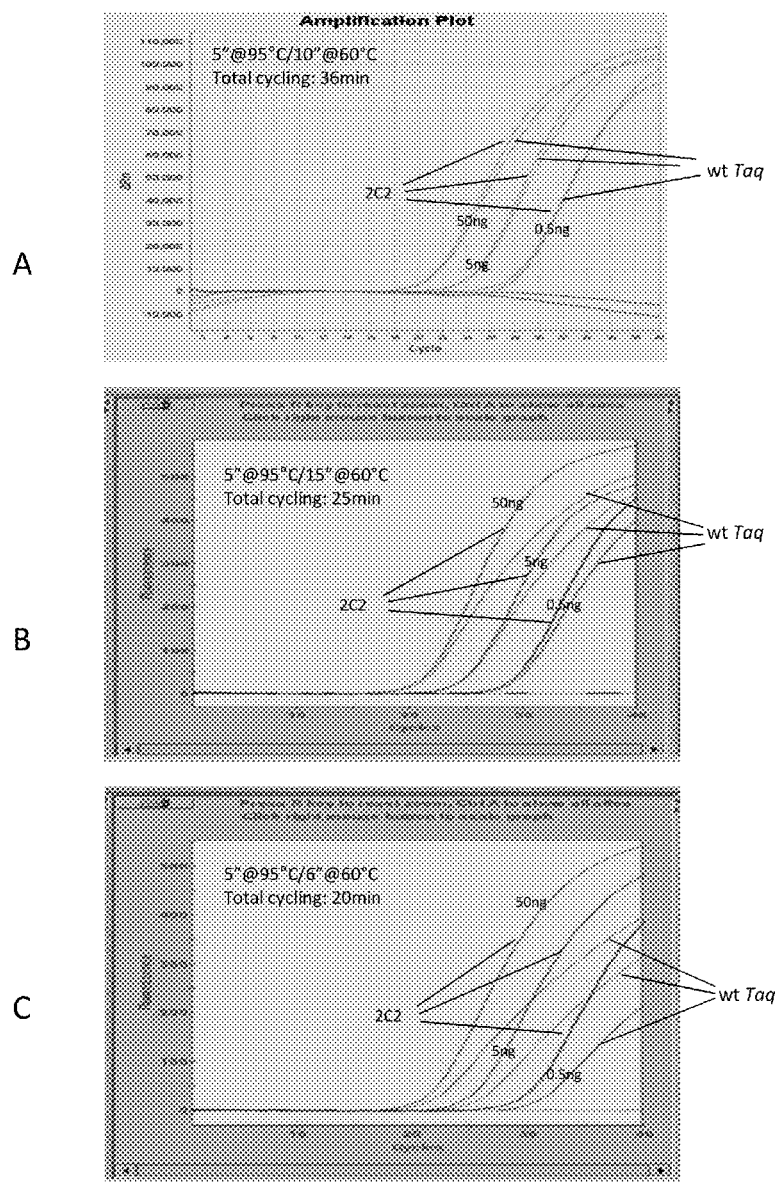
FIG. 2 depicts Real-Time QPCR amplification plots comparing amplification of a 69 base-pair target under various conditions, comparing the performance of wild-type Taq DNA polymerase and a mutant DNA polymerase according to the invention. Panel A shows amplification plots for amplifications run using a Step One Plus machine and using a 5 second denaturation period at 95° C., and a 10 second extension period at 60° C. (total cycling time of 36 minutes). Panel B shows amplification plots for amplifications run using a Smart Cycler and using a 5 second denaturation period at 95° C., and a 15 second extension period at 60° C. (total cycling time of 25 minutes). Panel C shows amplification plots for amplifications run using a Smart Cycler and using a 5 second denaturation period at 95° C., and a 6 second extension period at 60° C. (total cycling time of 20 minutes).

Reference will now be made in detail to various exemplary embodiments of the invention. The following detailed description is provided to give the reader a better understanding of embodiments of the invention. The following description should not be interpreted as limiting the invention in any way.

Before embodiments of the present invention are described in detail, it is to be understood that the terminology used herein is for the purpose of describing particular embodiments only, and is not intended to be limiting. Further, where a range of values is provided, it is understood that each intervening value, to the tenth of the unit of the lower limit, unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither, or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which the term belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited. The present disclosure is controlling to the extent it conflicts with any incorporated publication.

As used herein and in the appended claims, the singular forms "a", "an", and "the" include plural referents unless the context clearly dictates otherwise. Thus, for example, reference to "a polymerase" includes a plurality of such polymerases and reference to "the sample" includes reference to one or more samples and equivalents thereof known to those skilled in the art, and so forth.

In a first aspect, the present invention provides genetically engineered DNA polymerases, which can be suitable for use in PCR reactions. As used herein, the term "genetically engineered" is used interchangeably with "mutant" to indicate a protein or nucleic acid that has been altered in its sequence from the wild-type sequence to include an amino acid residue or nucleotide that is different than the corresponding residue or nucleotide in the wild-type protein or nucleic acid, respectively, from which it is derived. Mutants according to the invention thus include site-directed mutants in which specific residues have been intentionally changed, include deletions of one or more residue; insertions of one or more residue, and replacement of one or more residue of one Type-A DNA polymerase with an exogenous sequence, such as a corresponding sequence from another Type-A DNA polymerase. In situations where a replacement/substitution of one or very few residues is made to create a mutant, it is a straightforward matter to identify the DNA polymerase "from which the mutant is derived". However, in situations where regions of sequences are replaced by other regions of sequences, it may be difficult to define the DNA polymerase "from which the mutant is derived". In such cases, it is sufficient to understand that the mutant can be considered "derived" from either/any of the wild-type thermostable Type-A DNA polymerases from which sequences of the mutant show identity, particularly any one of the exemplary DNA polymerases shown in FIG. 1 (SEQ ID NOs:1-10).

In the exemplary embodiments discussed in detail herein, the DNA polymerases of the invention are mutant forms of wild-type Taq DNA polymerase, which have altered features that provide the mutant polymerases with advantageous properties. However, it is to be understood that the invention is not limited to the exemplary embodiments discussed in detail below. For example, the invention includes mutants of polymerases other than Taq DNA polymerase, such as mutants of any thermostable Type-A family DNA polymerase. These mutants can be mutants of polymerases, including but not limited to those, from species of *Thermus* or *Thermatoga*. It is well documented and well understood by those of skill in the art that thermostable Type-A DNA polymerases show high levels of sequence identity and conservation. Thus, it is a simple matter for one of skill in the art to identify residues of one particular Type-A DNA polymerase that correspond to residues of another. Thus, reference herein to specific mutations in wild-type Taq DNA polymerase can easily be correlated to corresponding mutations in other polymerases.

FIG. 1 presents an alignment of the primary amino acid sequences of several non-limiting exemplary thermostable Type-A DNA polymerases. As shown in FIG. 1, various regions of thermostable Type-A DNA polymerases are highly conserved while other regions are variable. Those of skill in the art will immediately recognize and understand that mutations in addition to those specifically identified and discussed herein may be made in the variable regions of Type-A DNA polymerases without altering, or without substantially altering, the polymerase activity of the mutated enzyme. Likewise, conservative mutations at conserved residues may be made without altering, or substantially altering, the polymerase activity of the mutated enzyme. Mutating enzymes based on comparative structure analysis with other related enzymes is a common and useful technique in the molecular biology field that allows a person of skill to reasonably predict the effect of a given mutation on the enzymatic activity of the enzyme. Using the structural data and known physical properties of amino acids, those of skill in the art can mutate enzymes, such as the DNA polymerases encompassed by the present invention, without altering, or without substantially altering, the essential enzymatic characteristics of the enzymes.

Thus, in embodiments, the present invention is directed to mutant thermostable Type-A DNA polymerases having 30% or more sequence identity to the wild-type enzyme from which they are derived, 40% or more sequence identity, 50% or more sequence identity, 55% or more identity, 60% or more identity, 65% or more identity, 70% or more identity, 75% or more identity, 80% or more identity, 85% or more identity, 90% or more identity, 91% or more identity, 92% or more identity, 93% or more identity, 94% or more identity, 95% or more identity, 96% or more identity, 97% or more identity, 98% or more identity, or 99% or more identity. Identity can be calculated by a linear comparison of amino acid sequences, optimized for the greatest amount of overlap of the sequences compared. Percentage is determined with reference to the wild-type sequence. As those of skill in the art will recognize, any particular level of identity (e.g., 51%, 52%, 53%, etc.) or range of identity encompassed by the values given herein are contemplated by the invention, and as such, each specific value and range need not be recited herein for those of skill in the art to recognize that the invention encompasses those values and ranges. In exemplary embodiments, the mutant DNA polymerase is derived from wild-type Taq DNA polymerase, and the above levels of sequence identity are based on the wild-type Taq DNA polymerase sequence.

In some embodiments of this invention, a mutant DNA polymerase comprises a sequence at least 31% (or at least 40, 50, 55, 60, 65, 70, 75, 80, 85, 90, 91, 92, 93, 94, 95, 96, 97, 98 or 99%) identical to any one of SEQ ID NOs: 1-10, which mutant polymerase comprises a mutation at residue 507 of wild-type Taq polymerase or at a residue of another thermostable Type-A DNA polymerase corresponding to residue 507 of wild-type Taq polymerase, as well as at least one mutation at a position selected from residues 59, 155, 245, 375, 508, 734, and 749 of wild-type Taq DNA polymerase or at one or more residues of another thermostable Type-A DNA polymerase corresponding to those residues. The mutant has a higher polymerization rate and/or resistance to inhibitors compared to the polymerase in FIG. 1 (SEQ ID NOs:1-10) that shares the most sequence identity with the mutant.

In some embodiments, the mutant polymerase of the present invention is encoded by a nucleic acid that hybridizes to the complement of a DNA sequence coding for SEQ ID NO:4 (wild-type Taq polymerase) under stringent conditions, wherein the mutant polymerase comprises a mutation at residue 507 of wild-type Taq polymerase or at a residue of another thermostable Type-A DNA polymerase corresponding to residue 507 of wild-type Taq polymerase, as well as at least one mutation at a position selected from residues 59, 155, 245, 375, 508, 734, and 749 of wild-type Taq DNA polymerase or at one or more residues of another thermostable Type-A DNA polymerase corresponding to those residues. The mutant has a higher polymerization rate and/or resistance to inhibitors compared to the polymerase in FIG. 1 (SEQ ID NOs:1-10) that shares the most sequence identity with the mutant. The stringent conditions refer to an experimental condition equivalent to hybridizing at 42° C. in 1×SSC, and washing at 65° C. in 0.1×SSC and 0.1% SDS.

In some embodiments, mutant DNA polymerases are provided that are faster than the wild-type enzyme from which they derive. In general, a "fast" or "faster" DNA polymerase is one that can incorporate nucleotides into a primed nucleic acid at a greater rate under a set of conditions than the wild-type enzyme from which it derives. The "fast" polymerase need not provide an increased rate of incorporation under all conditions, but rather may be one that incorporates at an increased rate under one or more conditions, which generally are those used in typical nucleic acid polymerase reactions. For example, according to the invention, a polymerase is considered "faster" if it satisfies the following criteria under PCR conditions. Using equivalent enzyme amounts, a "fast" DNA polymerase, such as a "fast" Taq mutant, will produce earlier Ct values, relative to the corresponding wild-type polymerase, as the time used for the PCR extension step (or a combined anneal/extend step) is incrementally decreased during subsequent experiments. A suitable time range consists of several time points, beginning with the shortest time period where Ct values are identical between wild type and mutant enzymes (long cycling conditions, where sufficient time allows slower wild-type enzyme to catch up with faster mutant) and the time period where no amplification occurs for either wild-type or mutant enzyme (insufficient time for fast enzyme to generate amplicon). "Fast" polymerases are useful in many applications, including Fast PCR, which is a modified PCR reaction that permits amplification of target nucleic acids in a shorter period of time, typically 40 minutes or less, than standard PCR, which typically takes about 90 minutes.

In the exemplary embodiments of this aspect of the invention, mutant Taq DNA polymerases are provided that show a greater rate of polymerization of a nucleic acid from a primed DNA template, as compared to the wild-type Taq DNA polymerase from which they derive. The DNA polymerases of this embodiment of the invention comprise at least one mutation, as compared to wild-type Taq DNA polymerase, that allows for an increased rate of polymerization of a DNA template. In preferred embodiments, the mutation is at E507 of Taq DNA polymerase or at a residue of another thermostable Type-A DNA polymerase corresponding to E507 of Taq DNA polymerase.

In another aspect, the engineered DNA polymerases of the invention are resistant to one or more inhibitors of a particular DNA polymerase. More specifically, a DNA polymerase according to this aspect of the present invention comprises at least one mutation, as compared to the wild-type DNA polymerase from which it derives, that allows for acceptable levels of DNA polymerization or correct amplification of a desired product during PCR in the presence of one or more inhibitors that reduce the polymerization rate of the wild-type DNA polymerase to a level that does not permit successful product formation in a PCR reaction. Any assay known in the art for determining polymerase activity and/or product formation can be used. In preferred embodiments, an assay as described above, but additionally including one or more inhibitors in one or more of the polymerization reactions, is used to determine inhibition. The DNA polymerases of this aspect of the invention typically have a mutation at one or more of residues 59, 155, 245, 375, 734, 749, and 508 of Taq, or at residue(s) corresponding to those residues in another thermostable Type-A DNA polymerase. In exemplary embodiments, the following mutations are present in Taq DNA polymerase, or at residues corresponding to these residues in Taq: G59W, V155I, L245M, L375V E507K, K508R, E734G, and F749I.

Among the inhibitors of Taq DNA polymerase that the present mutant polymerases are resistant to, mention may be made of: whole blood, fractions of whole blood, or components of blood, such as blood plasma, hemoglobin, heme, immunoglobulin G, and lactoferrin; cell lysates, such as ones containing inhibitory concentrations of polysaccharides; plant substances, such as pectin, xylan, and acidic polysaccharides; substances found in soil samples, such as humic acid, fulvic acid, and metal ions, including heavy metals and heavy metal ions; and certain organic solvents. Additional non-limiting examples include urea, heparin, EDTA, organic and phenolic compounds (e.g., phenol), glycogen, fats, calcium, cellulose, nitrocellulose, mineral oil, pollen, glove powder, SDS, and detergents. As the analysis of blood samples is of importance in medical and forensic analyses, resistance to inhibitors found in blood or blood fractions, including inhibitors that are commonly added to blood to stabilize it (e.g., EDTA and heparin) is a characteristic of some mutant enzymes according to certain embodiments. Various other inhibitors are known in the art, including without limitation those discussed in Kermekchiev, et al., "Mutants of Taq DNA polymerase resistant to PCR inhibitors allow DNA amplification from whole blood and crude soil samples", Nucleic Acids Research, Vol. 1, p. 14, 2008; and Abu Al-Soud, W., et al., "Capacity of Nine Thermostable DNA Polymerases To Mediate DNA Amplification in the Presence of PCR-Inhibiting Samples", Applied and Environmental Microbiology, Vol. 64, No. 10, October 1998.

In preferred embodiments, an engineered DNA polymerase according to the invention possesses both increased DNA polymerization rate and resistance to at least one DNA polymerase inhibitor. Such polymerases thus are capable of polymerizing a nucleic acid strand from a primed DNA template at an increased rate even in the presence of substances that are widely known to be inhibitory to the polymerization rate of the wild-type DNA polymerase.

The DNA polymerases of the invention are suitable for use in any nucleic acid polymerization reaction. The polymerases are advantageously used in any variation or type of PCR reaction for amplification of nucleic acids, including both DNA and RNA amplifications. For amplification of RNA templates, an RNA-dependent DNA polymerase (e.g., a reverse transcriptase; RT) can be used to make a DNA strand complementary to the RNA template, and a DNA polymerase of the invention can be used to amplify the DNA complementary strand. Due to their increased polymerization rate, the polymerase enzymes of the present invention are well suited for "fast PCR" reactions, such as those known in the art. Further, due to their resistance to inhibitors found in blood and blood products, they are particularly well suited for "fast PCR" reactions in samples that contain blood or fractions of blood. Preferably, they are well suited for "fast PCR" reactions in "dirty samples, such as those containing blood or fractions of blood.

The genetically engineered DNA polymerases of the invention can be produced and obtained using any suitable technique known in the art. For example, nucleic acids encoding the DNA polymerases may be introduced into a host cell and the mutant polymerases recombinantly produced from the resulting recombinant cell. Numerous techniques for introducing heterologous nucleic acids into host cells, and recombinant production of proteins from such cells, are known in the art, and any suitable technique may be used by the practitioner to produce the engineered polymerases.

By their recombinant nature, the mutant DNA polymerases of the invention are not products of nature, but are instead created through human intervention. In some embodiments, the engineered polymerases are used in the environment in which they are produced. However, the engineered DNA polymerases of the invention are preferably purified away from some or all other substances present in the environment in which the polymerases are produced. Various protocols for purification of proteins are known and widely used in the art. For example, protocols for purification of recombinantly expressed proteins from host cells are known. In particular, various protocols for purification of recombinant Taq DNA polymerases and other Type-A polymerases from host cells are known in the art. Protocols for purification can include one or more of the following techniques: cell lysis and centrifugation, for example to separate large cell debris and solid materials; precipitation with salt(s) and/or organic solvent(s); and column chromatography (e.g., size exclusion chromatography, anion- or cation-exchange chromatography, affinity chromatography). In general, the mutant DNA polymerases are purified to an extent that no other detectable DNA polymerase activity is present in samples containing the mutant DNA polymerases. Typically, the DNA polymerases are purified from most, preferably all, other proteinaceous material present in the environment in which they are produced. As a general matter, a "purified" DNA polymerase is one that represents at least 20%, at least 50%, at least 60%, at least 70%, at least 80%, at least 90%, more preferably at least 95%, and most preferably at least 99% or greater of the proteinaceous material in the sample in which it is contained, as determined by SDS gel electrophoresis and staining with Coomassie Blue. As used herein, the term "isolated" is used interchangeably with "pure", to signify a purity, with respect to other proteinaceous molecules in a sample, of at least 99%. That is, the pure or isolated molecule represents at least 99% of the proteinaceous molecules in a sample (prior, of course, to its addition to other substances for a nucleic acid polymerization reaction). In accordance with the discussion above relating to stated numerical values, the level of purity can be any specific value within the ranges discussed here, and each specific value need not be specifically listed for those of skill in the art to recognize that the invention contemplates all of the values.

In developing the exemplary DNA polymerases of the invention discussed in detail, the inventors mutagenized a nucleic acid encoding wild-type Taq DNA polymerase (SEQ ID NO:4 and SEQ ID NO:11, respectively) and selected mutants having increased polymerization rate. Various mutants were isolated, and their amino acid sequences determined. Many had increased polymerization rates as compared to the wild-type Taq polymerase. Surprisingly, the inventors found that certain mutants having increased polymerization rate also had an enhanced resistance to certain substances that are widely known in the art as inhibiting the polymerization activity of polymerases, and in particular reducing (or completely abolishing) the polymerization rate of polymerases. The present invention thus provides polymerases that can be advantageously used for rapid or "fast" PCR and for PCR in samples that contain common PCR/QPCR inhibitors.

The sequences of two exemplary engineered DNA polymerases are provided herein as SEQ ID NO:12 and SEQ ID NO:14. As shown in the sequences, one exemplary mutant DNA polymerase (SEQ ID NO:12) has the sequence of wild-type Taq DNA polymerase, with the exception of mutations at residues 59, 245, 375, 507, 734, and 749. Also as shown in the sequences, one exemplary mutant DNA polymerase (SEQ ID NO:14) has the sequence of wild-type Taq DNA polymerase with the exception of mutations at residues 59, 155, 245, 375, 507, 508, 734, and 749. Representative nucleic acid sequences encoding these mutant proteins are provided as SEQ ID NO:13 and SEQ ID NO:15, respectively.

The sequence of yet another exemplary DNA polymerase of the invention is provided as SEQ ID NO:16. The sequence of this mutant DNA polymerase has the sequence of wild-type Taq DNA polymerase with the exception of mutations at residues 59, 245, 375, 507, 508, 734, and 749. Further, the sequence of another exemplary DNA polymerase of the invention is provided as SEQ ID NO:18. The sequence of this mutant DNA polymerase has the sequence of wild-type Taq DNA polymerase with the exception of mutations at residues 59, 155, 245, 375, 507, 734, and 749. Representative nucleic acid sequences encoding these mutant proteins are provided as SEQ ID NO:17 and SEQ ID NO:19, respectively.

Additionally, the sequence of another exemplary DNA polymerase of the invention is provided as SEQ ID NO:20. The sequence of this mutant DNA polymerase has the sequence of wild-type Taq DNA polymerase with the exception of a mutation at residue 507, where the mutation is not an E507Q mutation. A representative nucleic acid sequence encoding this mutant protein is provided as SEQ ID NO:21. Another exemplary DNA polymerase of the invention is provided as SEQ NO 22. The sequence of this mutant DNA polymerase has the sequence of wild-type Taq DNA polymerase with the exception of an E507K mutation. A representative nucleic acid sequence encoding this mutant protein is provided as SEQ ID NO:23. The sequences of other exemplary DNA polymerases of the invention are provided as SEQ ID NO:24 and SEQ ID NO:26. The sequences of these mutant DNA polymerases have the sequence of wild-type Taq DNA polymerase with the exception of mutations at residues 245 and 507. Representative nucleic acid sequences encoding these mutant proteins are provided as SEQ ID NO:25 and SEQ ID NO:27, respectively. The sequences of other exemplary DNA polymerases of the invention are provided as SEQ ID NO:28 and SEQ ID NO:30. The sequences of these mutant DNA polymerases have the sequence of wild-type Taq DNA polymerase with the exception of mutations at residues 155, 245, and 507. Representative nucleic acid sequences encoding these mutant proteins are provided as SEQ ID NO:29 and SEQ ID NO:31, respectively.

Yet again, the sequences of two particular mutant DNA polymerases of the invention are provided as SEQ ID NO:32 and SEQ ID NO:34 (encoded by SEQ ID NO:33 and SEQ ID NO:35, respectively). Additional particular mutant DNA polymerases according to the invention are provided as SEQ ID NO:36 and SEQ ID NO:38 (encoded by SEQ ID NO:37 and SEQ ID NO:39, respectively).

The mutant DNA polymerase can be an amino acid polymer represented by a sequence consisting of the sequence disclosed as SEQ ID NO:12, 14, 16, 18, 20, 22, 24, 26, 28, 30, 32, 34, 36, or 38. Alternatively, the polymerase can be an amino acid polymer represented by a sequence that comprises one of these sequences, but has one or more additional amino acids added to the polymer at the C-terminus, the N-terminus, or both. Post-translationally modified residues, or analogs of amino acid residues, are encompassed by the primary sequences discussed herein. In embodiments, the mutant DNA polymerase does not comprise an E507Q mutation or an E507K mutation in Taq DNA polymerase as the sole mutation, as such mutants do not perform adequately under inhibitory conditions. In embodiments, the mutant DNA polymerase is a mutant of another thermostable Type-A DNA polymerase, and likewise does not comprise an E507Q or E507K mutation at a residue corresponding to the Taq 507 residue as the sole mutation selected from among the mutations specifically exemplified herein.

While exemplary embodiments discussed in detail herein relate to Taq DNA polymerase mutants and other thermostable Type-A DNA polymerases, it is to be understood that the mutant DNA polymerases may be derived from any DNA polymerase having identity to a Type-A polymerase. Where the mutant DNA polymerase is not derived from Taq DNA polymerase, the mutant polymerase can have one or more mutations at residues corresponding to the residues identified herein with specific reference to Taq polymerase. As will be recognized by those of skill in the art, the DNA polymerases may be any thermostable DNA polymerase, including, but not limited to thermostable Eubacterial or Archaeal DNA polymerases, as well as mutants or derivatives thereof. Thus, in embodiments, the DNA polymerase is derived from an Archaeal DNA polymerase. Suitable thermostable Pol I DNA polymerases can be derived from a variety of thermophilic Eubacteria, including, but not necessarily limited to, *Thermus* species and *Thermotoga maritima*, such as *Thermus aquaticus* (Taq), *Thermus thermophilus* (Tth), and *Thermotoga maritima* (Tma UITma).

The mutant DNA polymerases of the present invention can have the mutations specified and exemplified above. It has been realized that disruption of the wild-type sequence at the residues and combinations of residues specified herein provides mutant DNA polymerases with advantageous, and even unexpected, properties. It is to be understood that alteration of the cited residues by an amino acid substitution can result in the advantageous properties discussed herein. Further, deletion of one or more of the noted residues can also produce mutant DNA polymerases according to the invention. Thus, for example mutation of a glycine residue (e.g., G59 of Taq) with one of the other 19 typically recognized naturally occurring amino acid or one of the other naturally occurring (but less common) amino acids (e.g., selenocysteine) residues can provide a mutant thermostable Type-A DNA polymerase with increased polymerization activity and resistance to inhibitors. While not being limited to any particular mutant sequence, exemplary mutant sequences are provided herein as specific SEQ ID NOs. Corresponding exemplary nucleic acid sequences encoding these proteins are also provided as specific SEQ ID NOs.

While a variety of mutations can be made at each residue noted above, mention may be made of the following non-limiting mutations. Glycine at residue 59 can be altered to alanine, valine, leucine, isoleucine, proline, phenylalanine, tryptophan, methionine, aspartic acid, glutamic acid, lysine, arginine, or histidine, and in particular embodiments, to leucine, isoleucine, phenylalanine, tryptophan, methionine, tyrosine, or glutamine. Valine at residue 155 can be altered to glycine, serine, threonine, cysteine, tyrosine, asparagine, glutamine, aspartic acid, glutamic acid, lysine, arginine, or histidine, and in particular embodiments, to leucine, isoleucine, phenylalanine, tryptophan, methionine, tyrosine, or glutamine. Leucine at residue 245 and/or residue 375 can be altered to methionine, valine, glycine, serine, threonine, cysteine, tyrosine, asparagine, glutamine, aspartic acid, glutamic acid, lysine, arginine, or histidine, and in particular embodiments, to valine, phenylalanine, tryptophan, methionine, tyrosine, or glutamine. Glutamic acid at residue 507 and/or residue 734 can be altered to alanine, valine, leucine, isoleucine, proline, phenylalanine, tryptophan, methionine, glycine, serine, threonine, cysteine, tyrosine, asparagine, glutamine, lysine, arginine, or histidine, and in particular embodiments to glycine, serine, alanine, valine, leucine, or isoleucine. Lysine at residue 508 can be altered to alanine, valine, leucine, isoleucine, proline, phenylalanine, tryptophan, methionine, glycine, serine, threonine, cysteine, tyrosine, asparagine, glutamine, aspartic acid, glutamic acid, lysine, arginine, or histidine, and in particular embodiments, to leucine, isoleucine, phenylalanine, tryptophan, methionine, tyrosine, or arginine.

As those of skill in the art will immediately recognize, equivalent sequences of those of the exemplary SEQ ID NOs can be easily created by making one or more conservative substitutions at one or more residues not specified. Such equivalent sequences retain the essential polymerase characteristics of the mutant enzymes. The various conservative substitutions for different amino acids are known in the art, and need not be detailed herein. Important regions and residues for DNA polymerase activity of Taq DNA polymerase and other Type-A DNA polymerases are well characterized, and those of skill in the art are well aware of which regions and residues can be altered without disrupting the activity of the DNA polymerase of interest. An exemplary comparison of selected thermostable Type-A polymerases is provided in FIG. 1 to give the reader an understanding of conserved and variable regions within this group of enzymes; however, those of skill in the art will be aware of other alterations that can be made without substantially altering the activities discussed herein. In view of the fact that production of recombinant proteins is a routine matter in the field of biotechnology today, and as polymerase assays, such as Taq DNA polymerase assays, are well known and widely practiced as routine assays, production of mutant polymerases according to the present invention using the information provided herein is a routine matter for those of skill in the art. Automation and very powerful techniques and kits allow those practicing the invention to rapidly and routinely identify mutants according to the invention, and identify the particular levels of polymerase activity of interest (i.e., polymerization rate and polymerization rate in the presence of inhibitor(s)).

Alternatively or additionally, the mutants of the invention can comprise a specified number of mutations, as compared to the wild-type enzyme from which they are derived. For example, the mutants can comprise one or more mutations, preferably including a mutation corresponding to residue 507 of wild-type Taq DNA polymerase, but preferably not comprising an E507Q or E507K mutation of Taq or another thermostable Type-A DNA polymerase as the sole mutation. For example, the mutants can comprise 2, 3, 4, 5, 6, 7, 8, 9, 10, or more mutations. In exemplary embodiments, the mutants comprise two to eight specifically engineered mutations. In some embodiments, the mutants comprise a total of 8-20 mutations, 21-30 mutations, 31-40 mutations, or 41-50 mutations. In some embodiments, the mutants comprise 51-100 mutations or more.

As a general matter, it has been found that mutation of E507 of Taq DNA polymerase, and in particular the mutation E507K, provides the mutant polymerase with enhanced polymerization speed, as compared to the wild-type Taq polymerase from which it derives. However, a substantial enhancement of resistance to inhibitors was not detected in mutants comprising this mutation as the sole mutation. Interestingly, the combination of this mutation with the various other mutations, either in the form of double mutants or mutants having a higher number of defined amino acid alterations, provides additional speed enhancements and/or resistance to the deleterious effects of substances known to inhibit the polymerase activity of DNA polymerases. The present invention provides a number of mutant enzymes that have the surprising ability to polymerize nucleic acids at a faster rate than the wild-type enzymes from which they derive while at the same time showing resistance to DNA polymerase inhibitors.

The mutant DNA polymerases of the present invention can be provided in purified or isolated form, or can be part of a composition. Preferably, where in a composition, the mutant DNA polymerases are first purified to some extent, more preferably to a high level of purity (e.g., about 99% or higher). Compositions according to the invention can be any type of composition desired, but typically are aqueous compositions suitable for use as, or inclusion in, a composition for amplification of a target nucleic acid, and in particular for acellular amplification, such as through use of a PCR technique. As such, the compositions typically comprise at least one substance other than the mutant DNA polymerase, such as water, glycerol or another stabilizing agent, an aqueous buffer, an aqueous salt buffer, and the like. In exemplary embodiments, the compositions comprise some or all of the solvents, salts, buffers, nucleotides, and other reagents typically present in a PCR reaction. Thus, in some embodiments, the compositions comprise one or more nucleoside triphosphates, one or more nucleic acid primers or probes, one or more additional nucleic acid polymerases or fragments thereof having desired activities, one or more polymerization detection agents (e.g., specific or non-specific dyes or fluorescent molecules), and/or one or more nucleic acid templates for amplification or sequencing. Other exemplary substances include detergents, DMSO, DMF, gelatin, glycerol, betaine, spermidine, T4 gene 32 protein, E. coli SSB, BSA, and ammonium sulfate. Those of skill in the art are well aware of the various substances that can be included in polymerization reaction compositions, and as such an exhaustive list is not necessary here.

The invention further encompasses nucleic acids encoding the proteins of the invention. The amino acid sequences of exemplary mutant DNA polymerases of the invention are disclosed above as are exemplary nucleic acid sequences encoding them. As those of skill in the art are aware, nucleic acid sequences encoding amino acid sequences can be easily determined based on the genetic code. As also known by those of skill in the art, the genetic code is degenerate, such that multiple different codons can encode a single amino acid. The present invention recognizes the degeneracy of the genetic code, and provides for all nucleic acids that can encode a protein according to the invention. It is a matter of routine practice, which can be accomplished quickly using computers and publicly available software, to identify all possible nucleic acid sequences encoding a given amino acid sequence. Thus, one of skill in the art can easily identify nucleic acids according to the present invention without undue or excessive experimentation, and without the need to recite all such nucleic acids specifically by sequence herein. This concept extends to mutant DNA sequences that encode mutant polymerases other than Taq polymerases. That is, because one of skill can easily identify the residues in other thermostable Type-A polymerases that correspond to the specifically identified Taq residues, and because the skilled artisan can use the known sequences of the other Type-A polymerases (and their underlying DNA sequences), the skilled artisan can rapidly and accurately identify all of the nucleic acid sequences encoding all mutant polymerases encompassed by the invention.

The nucleic acids of the invention can be provided in a purified or isolated form. Like the DNA polymerases of the invention, the nucleic acids can be provided in pure or essentially pure form (e.g., as the sole or essentially sole component of a sample), or can be a part of a composition. Furthermore, as with the mutant DNA polymerases, when provided in a composition, the nucleic acids can represent substantially all, a majority, or a minority of the substances in the composition. Other components of the compositions can be any suitable substances, including, but not limited to, water, an aqueous buffer, salt(s), organic solvent(s), and nucleic acid polymerase(s). The nucleic acids can be provided as part of cells harboring them.

The nucleic acids can have a sequence that is represented by a sequence consisting of the sequences disclosed herein, or can have a sequence that comprises one of the sequences. In situations where the nucleic acids have a sequence that comprises a sequence disclosed herein, additional nucleotide sequences can be included at one or both ends of the sequences disclosed herein. For example, the nucleic acids of the invention can include sequences that participate in expression or regulation of expression of a coding region, sequences that participate in maintenance of the nucleic acid in a host cell (either transiently or permanently), sequences that allow for replication of the nucleic acid in a host cell (e.g., plasmid on sequences), and the like. The nucleic acids of the invention thus may be part of an autonomously replicating extrachromasomal element, such as a plasmid, virus, or phagemid, or can be part of an integration vector for homologous or non-homologous integration of the nucleic acid into a host genome.

The nucleic acids of the invention can be used for any suitable purpose, such as to produce mutant DNA polymerases according to the invention. Methods for using nucleic acids, and in particular for expressing nucleic acids (e.g., recombinant expression in a host cell), are widely known and practiced. Thus, they need not be detailed herein. Those practicing the invention may use any suitable method for using the nucleic acids of the invention without undue or excessive experimentation.

Using the engineered DNA polymerases, the inventors have developed methods of polymerizing nucleic acids from a primer or set of primers and a nucleic acid template. In general, the methods comprise: (A) exposing (such as combining together, mixing, etc.) an engineered DNA polymerase according to the invention to (1) a target nucleic acid and (2) at least one primer suitable for priming polymerization of a nucleic acid that is complementary to one strand of the target nucleic acid, and (B) exposing (such as subjecting) the polymerase, target nucleic acid, and primer(s) to conditions that allow polymerization of nucleic acids from the primer(s). The step of exposing the polymerase to the other substances can be any action that results in exposure of the recited substances to each other such that they can physically interact. It thus can comprise adding the substances together in a composition, mixing the substances together in a composition (i.e., a mixture), etc. Exposing may be performed fully or partially manually, or fully or partially automatically (i.e., by way of machinery, robotics, etc.). As those of skill in the art are aware, a wide variety of nucleic acids can be subjected to copying, amplifying, sequencing, etc. Thus, the invention is not limited by the target nucleic acid, its sequence, length, etc. Further, those of skill in the art are fully aware of the parameters to be considered when designing primers for priming polymerization of a nucleic acid based on a target nucleic acid template. Thus, the invention is not limited by the identity or sequence of the primers. It is to be understood that, where amplification is desired (e.g., PCR), two primers having different sequences and having specificity for two different sequences on opposite strands of the target nucleic acid should be used. In addition, the step of exposing the combined substances to conditions that allow for polymerization can be any action that allows for polymerization. A great many conditions that are suitable for polymerization are known in the art, and those of skill in the art may select any appropriate conditions, as the situation requires, without undue or excessive experimentation. Parameters to be considered include, but are not necessarily limited to, salt concentration, metal ion or chelator concentration, buffer concentration and identity, presence or absence of detergents and organic solvents, concentration of polymerase or other enzymes, presence or concentration of nucleotides or modified nucleotides, presence or concentration of polymerization inhibitors or terminators, presence or concentration of probes or dyes for detection of polymerization products, temperature, and length of time of exposure. In exemplary embodiments, the conditions that allow polymerization of nucleic acids from the primer(s) are conditions for a PCR reaction. As will be recognized by those of skill in the art, the step of exposing the substances to conditions for polymerization can be considered as a step of polymerizing, such as a step of amplifying a nucleic acid template.

In some embodiments, the method is a method of PCR. Numerous PCR methods are known in the art, and any such method may be used in conjunction with the engineered DNA polymerases of the invention. In exemplary embodiments, the PCR method is a "fast PCR" method that allows for shorter total cycling times, as compared to total cycling times required when using a wild-type DNA polymerase. In yet other exemplary embodiments, the PCR method is a "fast PCR" method conducted on "dirty" samples, such as blood. In general, as used herein, a "dirty" sample is one that includes undefined substances, typically present originally in the environment where the target nucleic acid was present. Thus, a "dirty" sample in general is a sample in which the target nucleic acid was not purified prior to inclusion in the polymerization reaction. In yet further exemplary embodiments, the PCR method is not a "fast PCR" reaction, for example it is a standard PCR reaction of a "dirty" sample.

In some embodiments, two or more primers having different sequences are used in the method. For example, in some embodiments two primers are used, where one primer specifically binds to one strand of the template DNA and the other binds to the other strand of the template DNA, allowing for production of a double-stranded polymerization product. In some embodiments, one primer is specific for a sequence present on a single-stranded RNA template, such as an mRNA. Polymerization of a first complementary strand of the RNA from the first primer provides a template for the second primer. Subsequent to a first polymerization, the first primer can prime polymerization from either the template RNA or the DNA complement. One or more nucleic acid probes having sequence specificity for the target nucleic acid (including a complementary strand of the target, where the target is single-stranded) can be included in the method to provide a means for detection.

As alluded to above, many PCR methods include probes, dyes, or other substances that allow for detection of polymerization (e.g., amplification) products. One example of such methods is Real-Time PCR. Accordingly, the method can include a step of including in the polymerization reaction a substance that allows for detection of polymerization products. Furthermore, the method of the invention encompasses methods that include one or more control reactions to determine if the methods, or particular method steps, have been performed successfully. The control reactions can be positive control reactions or negative control reactions. Those of skill in the art are fully capable of devising appropriate control reaction conditions without the need for particular steps to be detailed herein.

The invention provides kits. In general, the kits comprise one or more containers containing one or more mutant DNA polymerases of the invention. A kit can contain a single mutant polymerase in a single container, multiple containers containing the same mutant DNA polymerase, a single container containing two or more different mutant DNA polymerases of the invention, or multiple containers containing different mutant DNA polymerases or containing mixtures of two or more mutant DNA polymerases. Any combination and permutation of DNA polymerase(s) and containers is encompassed by the kits of the invention. Typically, the kits will also include packaging materials for holding the container or combination of containers. In some embodiments, the kits contain some or all of the reagents, materials, etc. for performing a method that uses a mutant DNA polymerase according to the invention. The kits thus may comprise some or all of the reagents for performing a PCR reaction using the DNA polymerase of the invention. Some or all of the components of the kits can be provided in containers separate from the container(s) containing the polymerases of the invention. Examples of additional components of the kits include, but are not limited to, one or more different polymerases, one or more primers that are specific for a control nucleic acid or for a target nucleic acid, one or more probes that are specific for a control nucleic acid or for a target nucleic acid, buffers for polymerization reactions (in 1× or concentrated forms), and one or more dyes or fluorescent molecules for detecting polymerization products.

The present invention thus provides the following. A nucleic acid polymerase consisting of or comprising an amino acid sequence represented by SEQ ID NO:12; a composition comprising the nucleic acid polymerase and at least one other substance (e.g., water or an aqueous buffer, a nucleic acid); and a kit comprising the nucleic acid polymerase. The invention also provides a method of amplifying a target nucleic acid, wherein the method comprises: combining a nucleic acid polymerase consisting of or comprising an amino acid sequence represented by SEQ ID NO:12 and the target nucleic acid, and subjecting the combination to conditions allowing for amplification of the target nucleic acid. The method can be a PCR amplification method, which can be performed in the presence of a PCR inhibitor, such as one that inhibits the activity of wild-type Taq DNA polymerase or another thermostable Type-A DNA polymerase. In embodiments, the invention provides such polymerase, composition, kit, and method where the polymerase consists of or comprises an amino acid sequence of a Type-A DNA polymerase that is not Taq but has mutations at amino acid residues corresponding to those present in SEQ ID NO:12.

The present invention also thus provides the following. A nucleic acid polymerase consisting of or comprising the amino acid sequence of wild-type Taq DNA polymerase, with the exception of mutations at residues 59, 245, 375, 507, 734, and 749. In some embodiments, the nucleic acid polymerase includes a G59W mutation, an L245M mutation, an L375V mutation, an E507K mutation, an E734G mutation, and/or an F749I mutation; a composition comprising the nucleic acid polymerase, and a kit comprising the nucleic acid polymerase. The invention also provides a method of amplifying a target nucleic acid, wherein the method comprises: combining a nucleic acid polymerase consisting of or comprising the amino acid sequence of wild-type Taq DNA polymerase, with the exception of mutations at residues 59, 245, 375, 507, 734, and 749 (for example, the specific mutations mentioned above), and subjecting the combination to conditions allowing for amplification of the target nucleic acid. The method can be a PCR amplification method, which can be performed in the presence of a PCR inhibitor, such as one that inhibits the activity of wild-type Taq DNA polymerase or another thermostable Type-A DNA polymerase. In embodiments, the invention provides such polymerase, composition, kit, and method where the polymerase consists of or comprises an amino acid sequence of a Type-A DNA polymerase that is not Taq but has mutations at amino acid residues corresponding to those recited above.

The present invention also thus further provides the following. A nucleic acid polymerase consisting of or comprising an amino acid sequence represented by SEQ ID NO:14; a composition comprising the nucleic acid polymerase and at least one other substance (e.g., water or an aqueous buffer, a nucleic acid); and a kit comprising the nucleic acid polymerase. The invention also provides a method of amplifying a target nucleic acid, wherein the method comprises: combining a nucleic acid polymerase consisting of or comprising an amino acid sequence represented by SEQ ID NO:14 and the target nucleic acid, and subjecting the combination to conditions allowing for amplification of the target nucleic acid. The method can be a PCR amplification method, which can be performed in the presence of a PCR inhibitor, such as one that inhibits the activity of wild-type Taq DNA polymerase or another thermostable Type-A DNA polymerase. In embodiments, the invention provides such polymerase, composition, kit, and method where the polymerase consists of or comprises an amino acid sequence of a Type-A DNA polymerase that is not Taq but has mutations at amino acid residues corresponding to those present in SEQ ID NO:14.

The present invention also further provides the following. A nucleic acid polymerase consisting of or comprising the amino acid sequence of wild-type Taq DNA polymerase, with the exception of mutations at residues 59, 155, 245, 375, 507, 508, 734, and 749. In some embodiments, the nucleic acid polymerase includes a G59W mutation, a V155I mutation, an L245M mutation, an L375V mutation, an E507K mutation, a K508R mutation, an E734G mutation, and/or an F749I mutation; a composition comprising the nucleic acid polymerase, and a kit comprising the nucleic acid polymerase. The invention also provides a method of amplifying a target nucleic acid, wherein the method comprises: combining a nucleic acid polymerase consisting of or comprising the amino acid sequence of wild-type Taq DNA polymerase, with the exception of mutations at residues 59, 155, 245, 375, 507, 508, 734, and 749 (for example, the specific mutations mentioned above), and subjecting the combination to conditions allowing for amplification of the target nucleic acid. The method can be a PCR amplification method, which can be performed in the presence of a PCR inhibitor, such as one that inhibits the activity of wild-type Taq DNA polymerase or another thermostable Type-A DNA polymerase. In embodiments, the invention provides such polymerase, composition, kit, and method where the polymerase consists of or comprises an amino acid sequence of a Type-A DNA polymerase that is not Taq but has mutations at amino acid residues corresponding to those recited above.

The present invention thus additionally provides the following. A nucleic acid polymerase consisting of or comprising an amino acid sequence represented by SEQ ID NO:16, a composition comprising the nucleic acid polymerase and at least one other substance (e.g., water or an aqueous buffer, a nucleic acid); and a kit comprising the nucleic acid polymerase. The invention also provides a method of amplifying a target nucleic acid, wherein the method comprises: combining a nucleic acid polymerase consisting of or comprising an amino acid sequence represented by SEQ ID NO:16 and the target nucleic acid, and subjecting the combination to conditions allowing for amplification of the target nucleic acid. The method can be a PCR amplification method, which can be performed in the presence of a PCR inhibitor, such as one that inhibits the activity of wild-type Taq DNA polymerase or another thermostable Type-A DNA polymerase. In embodiments, the invention provides such polymerase, composition, and kit where the polymerase consists of or comprises an amino acid sequence of a Type-A DNA polymerase that is not Taq but has mutations at amino acid residues corresponding to those present in SEQ ID NO:16.

The present invention additionally provides the following. A nucleic acid polymerase consisting of or comprising the amino acid sequence of wild-type Taq DNA polymerase, with the exception of mutations at residues 59, 245, 375, 507, 734, and 749. In some embodiments, the nucleic acid polymerase includes a G59W mutation, an L245M mutation, an L375V mutation, an E507K mutation, an E734G mutation, and/or an F749I mutation; a composition comprising the nucleic acid polymerase, and a kit comprising the nucleic acid polymerase. The invention also provides a method of amplifying a target nucleic acid, wherein the method comprises: combining a nucleic acid polymerase consisting of or comprising the amino acid sequence of wild-type Taq DNA polymerase, with the exception of mutations at residues 59, 245, 375, 507, 734, and 749 (for example, the specific mutations mentioned above), and subjecting the combination to conditions allowing for amplification of the target nucleic acid. The method can be a PCR amplification method, which can be performed in the presence of a PCR inhibitor, such as one that inhibits the activity of wild-type Taq DNA polymerase or another thermostable Type-A DNA polymerase. In embodiments, the invention provides such polymerase, composition, kit, and method where the polymerase consists of or comprises an amino acid sequence of a Type-A DNA polymerase that is not Taq but has mutations at amino acid residues corresponding to those recited above.

The present invention thus provides the following. A nucleic acid polymerase consisting of or comprising an amino acid sequence represented by SEQ ID NO:18, a composition comprising the nucleic acid polymerase and at least one other substance (e.g., water or an aqueous buffer, a nucleic acid); and a kit comprising the nucleic acid polymerase. The invention also provides a method of amplifying a target nucleic acid, wherein the method comprises: combining a nucleic acid polymerase consisting of or comprising an amino acid sequence represented by SEQ ID NO:18 and the target nucleic acid, and subjecting the combination to conditions allowing for amplification of the target nucleic acid. The method can be a PCR amplification method, which can be performed in the presence of a PCR inhibitor, such as one that inhibits the activity of wild-type Taq DNA polymerase or another thermostable Type-A DNA polymerase. In embodiments, the invention provides such polymerase, composition, and kit where the polymerase consists of or comprises an amino acid sequence of a Type-A DNA polymerase that is not Taq but has mutations at amino acid residues corresponding to those present in SEQ ID NO:18.

The present invention additionally provides the following. A nucleic acid polymerase consisting of or comprising the amino acid sequence of wild-type Taq DNA polymerase, with the exception of mutations at residues 59, 155, 245, 375, 507, 734, and 749. In some embodiments, the nucleic acid polymerase includes a G59W mutation, a V155I mutation, an L245M mutation, an L375V mutation, an E507K mutation, an E734G mutation, and/or an F749I mutation; a composition comprising the nucleic acid polymerase, and a kit comprising the nucleic acid polymerase. The invention also provides a method of amplifying a target nucleic acid, wherein the method comprises: combining a nucleic acid polymerase consisting of or comprising the amino acid sequence of wild-type Taq DNA polymerase, with the exception of mutations at residues 59, 155, 245, 375, 507, 734, and 749 (for example, the specific mutations mentioned above), and subjecting the combination to conditions allowing for amplification of the target nucleic acid. The method can be a PCR amplification method, which can be performed in the presence of a PCR inhibitor, such as one that inhibits the activity of wild-type Taq DNA polymerase or another thermostable Type-A DNA polymerase. In embodiments, the invention provides such polymerase, composition, kit, and method where the polymerase consists of or comprises an amino acid sequence of a Type-A DNA polymerase that is not Taq but has mutations at amino acid residues corresponding to those recited above.

The present invention also thus further provides the following. A nucleic acid polymerase consisting of or comprising an amino acid sequence represented by SEQ ID NO:22; a composition comprising the nucleic acid polymerase and at least one other substance (e.g., water or an aqueous buffer, a nucleic acid); and a kit comprising the nucleic acid polymerase. The invention also provides a method of amplifying a target nucleic acid, wherein the method comprises: combining a nucleic acid polymerase consisting of or comprising an amino acid sequence represented by SEQ ID NO:22 and the target nucleic acid, and subjecting the combination to conditions allowing for amplification of the target nucleic acid. The method can be a PCR amplification method, which can be performed in the presence of a PCR inhibitor, such as one that inhibits the activity of wild-type Taq DNA polymerase or another thermostable Type-A DNA polymerase. In embodiments, the invention provides such polymerase, composition, kit, and method where the polymerase consists of or comprises an amino acid sequence of a Type-A DNA polymerase that is not Taq but has mutations at amino acid residues corresponding to those present in SEQ ID NO:22.

The present invention also thus further provides the following. A nucleic acid polymerase consisting of or comprising an amino acid sequence represented by SEQ ID NO:20; a composition comprising the nucleic acid polymerase and at least one other substance (e.g., water or an aqueous buffer, a nucleic acid); and a kit comprising the nucleic acid polymerase. The invention also provides a method of amplifying a target nucleic acid, wherein the method comprises: combining a nucleic acid polymerase consisting of or comprising an amino acid sequence represented by SEQ ID NO:20 and the target nucleic acid, and subjecting the combination to conditions allowing for amplification of the target nucleic acid. The method can be a PCR amplification method, which can be performed in the presence of a PCR inhibitor, such as one that inhibits the activity of wild-type Taq DNA polymerase or another thermostable Type-A DNA polymerase. In embodiments, the invention provides such polymerase, composition, kit, and method where the polymerase consists of or comprises an amino acid sequence of a Type-A DNA polymerase that is not Taq but has mutations at amino acid residues corresponding to those present in SEQ ID NO:20.

Some embodiments of the present invention provide isolated nucleic acid molecules (DNA or RNA) that comprise a sequence encoding a polymerase mutant described herein. Vectors comprising such nucleic acid molecules, as well as prokaryotic or eukaryotic host cells comprising such vectors, are also provided.

EXAMPLES

The invention will be further explained by the following Examples, which are intended to be purely exemplary of the invention, and should not be considered as limiting the invention in any way.

Example 1

Generation and Screening of Mutant Polymerases

Mutant Taq DNA polymerases were generated by random mutagenesis of a nucleic acid comprising the sequence of SEQ ID NO:4, which encoded wild-type Taq DNA polymerase (SEQ ID NO:11). Briefly, random mutant libraries were subject to 5 rounds of selection under fast cycling conditions, followed by screening (after rounds 2, 4, and 5) to identify clones that support amplification using shortened extension times. Polymerases showing improved performance during Real-Time PCR under fast cycling conditions, as compared to wild-type Taq DNA polymerase, were subjected to DNA sequencing to identify mutations. Mutations of interest appearing in fast-amplifying clones were identified and recombined using site-directed mutagenesis. Recombinants were screened using Real-Time PCR with fast cycling conditions. Mutant polymerases that outperformed both wild-type Taq and the best performers from the original selection/screening were identified, sequenced, and purified for further characterization to identify clones with combinations of mutations that support PCR using the shortest extension times.

Example 2

Mutant Polymerases Amplify better than Wild-Type Taq Under Fast Cycling Conditions Selected mutant polymerases obtained according to Example 1 were further characterized to assess their ability to polymerize a nucleic acid chain from a primer. Specifically, real-time quantitative PCR reactions were performed under "fast cycling" conditions to amplify a 69 base-pair target nucleic acid.

Real-time PCR reactions using SYBR® Green dye to monitor amplification of the template were performed using wild-type Taq DNA polymerase and a mutant according to the invention referred to as "2C2" (SEQ ID NO:38). Two different real-time PCR systems were used: the Step-One-Plus™ system from Applied Biosystems (Life Technologies) and the SmartCycler® system (Cepheid). Extension times for the amplification reactions were varied in the experiment to generate data for a variety of time points, in order to better characterize the difference between the mutant and wild-type enzymes. As shown in FIG. 2, reactions were run with 0.5 ng, 5 ng, and 50 ng of template.

The results of the real-time PCR reactions are shown in FIG. 2, Panels A-C. More specifically, FIG. 2, Panel A, shows Real-Time QPCR amplification plots comparing amplification of the 69 base-pair template using a 5 second denaturation period at 95° C., and a 10 second extension period at 60° C., using a Step-One-Plus™ PCR system. Using these parameters, the total cycling time for the amplification run was 36 minutes. As can be seen from the plot, clone 2C2 shows a slight increase in polymerization rate under these conditions. Looking now at Panel B, a substantial difference in amplification rate can be seen between the mutant and wild-type enzymes. Panel B shows Real-Time QPCR amplification plots comparing amplification of the 69 base-pair template using a 5 second denaturation period at 95° C., and a 15 second extension period at 60° C., using a SmartCycler® system. Using these parameters, the total cycling time for the amplification run was 25 minutes. As shown in the panel, the mutant DNA polymerase showed a substantial increase in amplification product, as compared to the wild-type enzyme. Further, as shown in Panel C, shorter extension times result in an even more pronounced difference in Ct between the mutant and wild-type enzymes. Panel C shows Real-Time amplification plots for amplifications run using a 5 second denaturation period at 95° C., and a 6 second extension period at 60° C. (total cycling time of 20 minutes). The panel shows that the mutant provided normal or at least acceptable amplification of the template at this very short extension time, whereas the wild-type enzyme provided a much later Ct. The mutant polymerase thus amplifies target better than wild-type Taq under fast cycling conditions.

Example 3

Further Characterization of Mutant Polymerase Performance Under Fast Cycling Conditions In this Example 3, Real-Time PCR was performed on a 160 base-pair target DNA molecule, SYBR® Green, and the PCR systems of Example 2. The results are shown in FIG. 3, Panels A-C.

Figure 3:
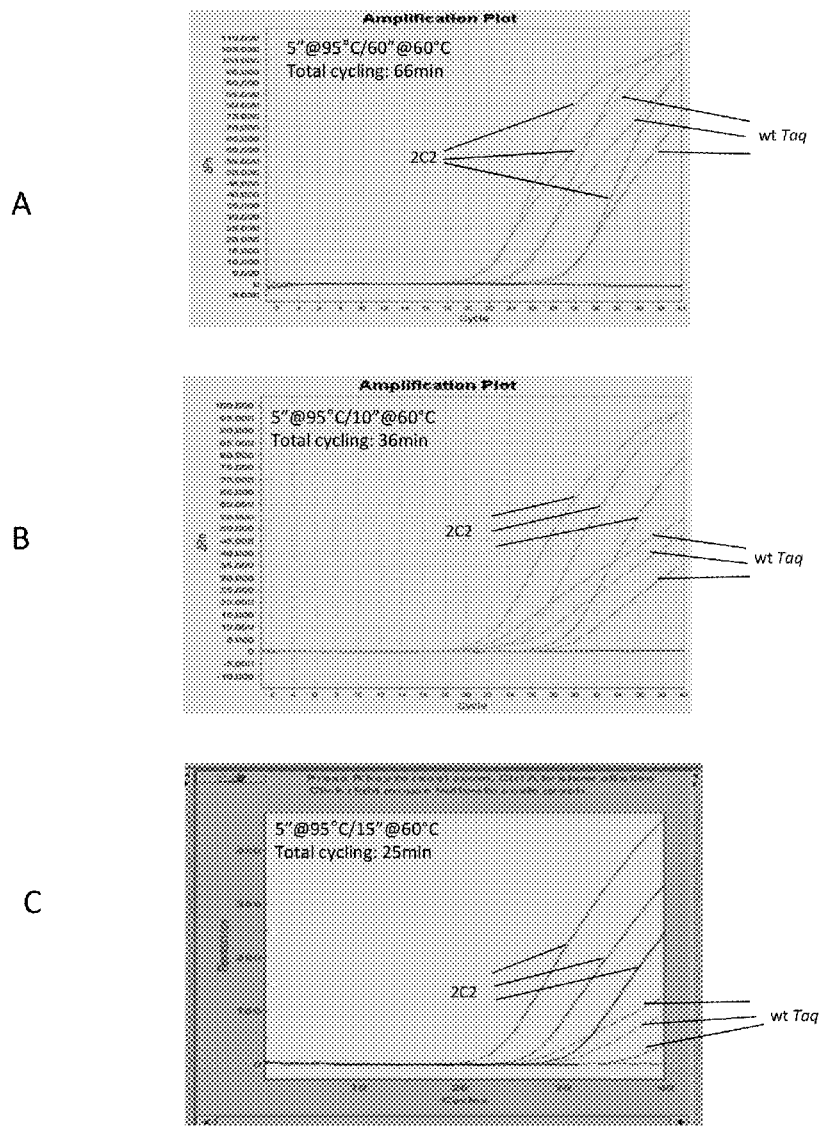
FIG. 3 depicts Real-Time QPCR amplification plots comparing amplification of a 160 base-pair target under various conditions, comparing the performance of wild-type Taq DNA polymerase and a mutant DNA polymerase according to the invention. Panel A shows amplification plots for amplifications run using a Step One Plus and using a 5 second denaturation period at 95° C., and a 60 second extension period at 60° C. (total cycling time of 66 minutes). Panel B shows amplification plots for amplifications run using a Step One Plus and using a 5 second denaturation period at 95° C., and a 15 second extension period at 60° C. (total cycling time of 25 minutes). Panel C shows amplification plots for amplifications run using a Smart Cycler and using a 5 second denaturation period at 95° C., and a 10 second extension period at 60° C. (total cycling time of 36 minutes).

FIG. 3, Panel A, shows Real-Time QPCR amplification plots comparing amplification of the 160 base-pair template using a 5 second denaturation period at 95° C., and a 60 second extension period at 60° C. (total cycling time of 66 minutes), and a Step-One-Plus™ PCR system. As can be seen from the panel, the mutant according to the present invention showed an earlier Ct compared to the wild-type enzyme. Panel B shows amplification plots for amplifications run using a 5 second denaturation period at 95° C., and a 15 second extension period at 60° C. (total cycling time of 25 minutes), using the SmartCycler™ system. Under these conditions, the difference between the mutant and wild-type enzymes is even more pronounced. Panel C shows amplification plots for amplifications run using a 5 second denaturation period at 95° C., and a 10 second extension period at 60° C. (total cycling time of 36 minutes), using the Step-One-Plus™ PCR system. The results also show a pronounced speed advantage for the mutant enzyme over the wild-type enzyme. These data further support the conclusion that mutants according to the invention amplify templates better than wild-type Taq under fast cycling conditions.

Example 4

Characterization of Mutant Enzyme Resistance to Inhibitors

To further characterize mutant enzymes of the invention, the inventors assayed the ability of a mutant enzyme to amplify a target DNA during End-Point PCR in the presence of whole blood (collected and stored in EDTA), which is known to contain inhibitors of Taq DNA polymerase activity. Specifically, PCR reactions containing components typical for End-Point assays were assembled using wild-type Taq (Taq2000, Agilent Technologies; SEQ ID NO:4), mutant "2C2" (SEQ ID NO:38), or mutant "Taq42" (SEQ ID NO:36). Either 20 ng of purified human genomic DNA or 1 ul human blood (2% final concentration) was added individually as template to enzyme master mixes previously aliquotted into PCR strip tubes. Each polymerase and template combination was assayed in duplicate. Amplification was performed using 1.25 Units of enzyme per 50 ul reaction mix. The thermocycling parameters were as follows: 95° C. for 5 minutes; 95° C. for 30 seconds; 58° C. for 30 seconds; and 72° C. for 60 seconds; for 40 cycles.

Figure 4:
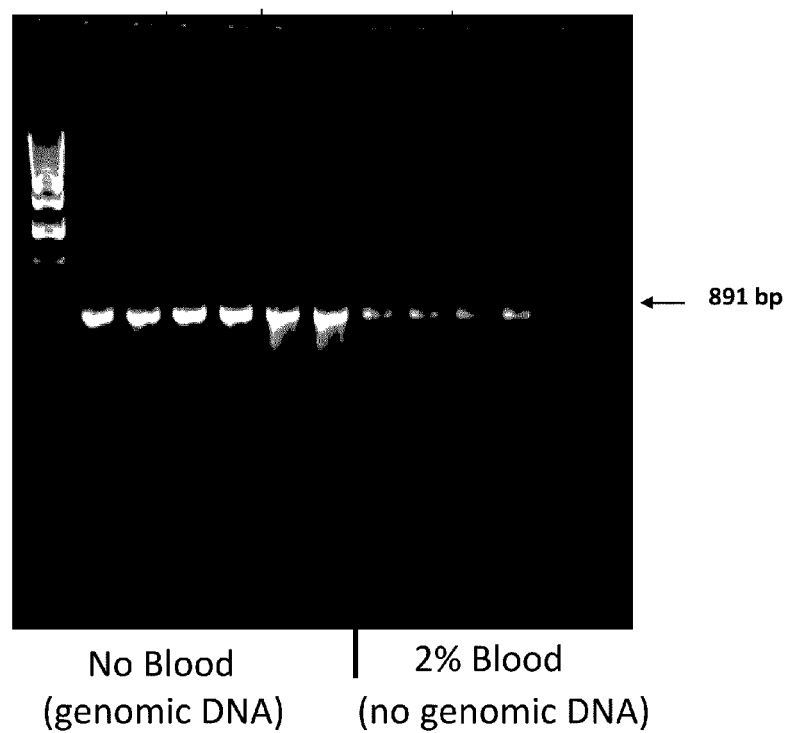
FIG. 4 depicts an agarose gel, showing amplification products obtained from PCR amplification of an 891 base pair target in the absence of blood or the presence of 2% (v/v) blood. 1.25 Units of enzyme were used per 50 ul reaction with a cycling scheme of 95° C. for 5 minutes, followed by 95° C. for 30 seconds, 58° C. for 30 seconds, and 72° C. for 60 seconds, run for 42 cycles.
Figure 8A:
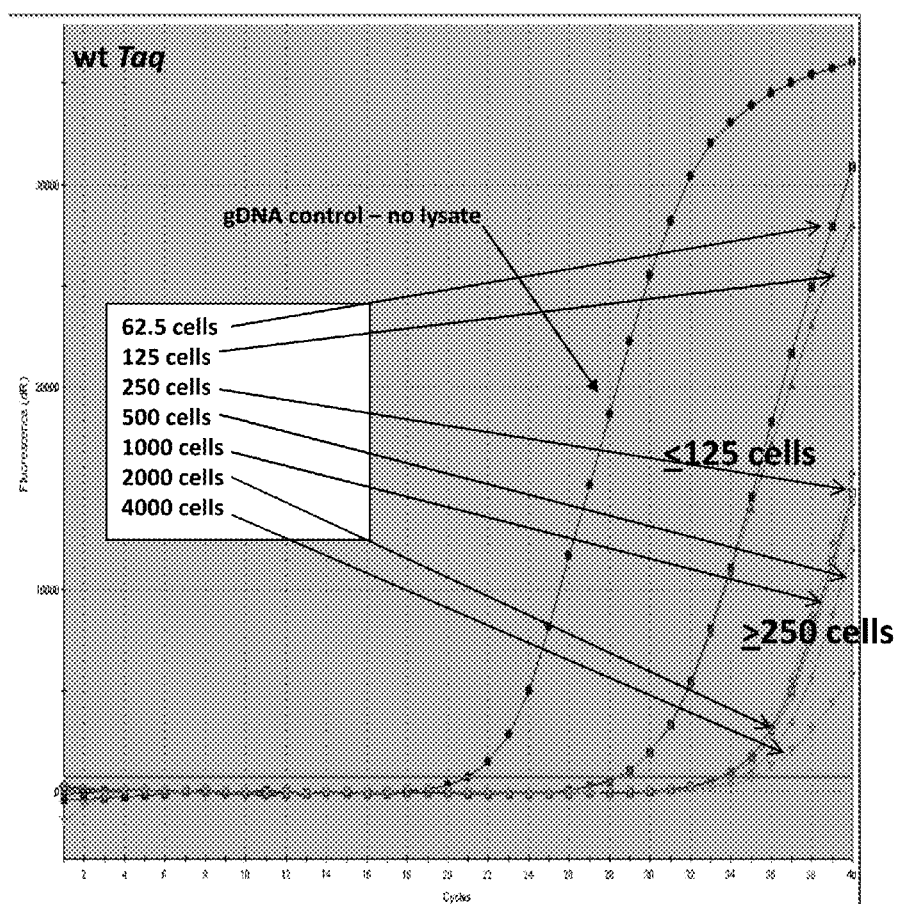
FIG. 8 depicts Real-Time QPCR amplification plots and melt curves comparing the amplification of a genomic fragment target by wild-type Taq DNA polymerase and a mutant according to the invention. Panels A and B show that the wild-type enzyme is poorly able to amplify the target in the presence of extract from 125 or fewer cells, and incapable of amplifying the target in the presence of extract from 250 or more cells. Panels C and D show that a mutant according to the invention can amplify the target in the presence of extract from at least 4000 cells.
Figure 8B:
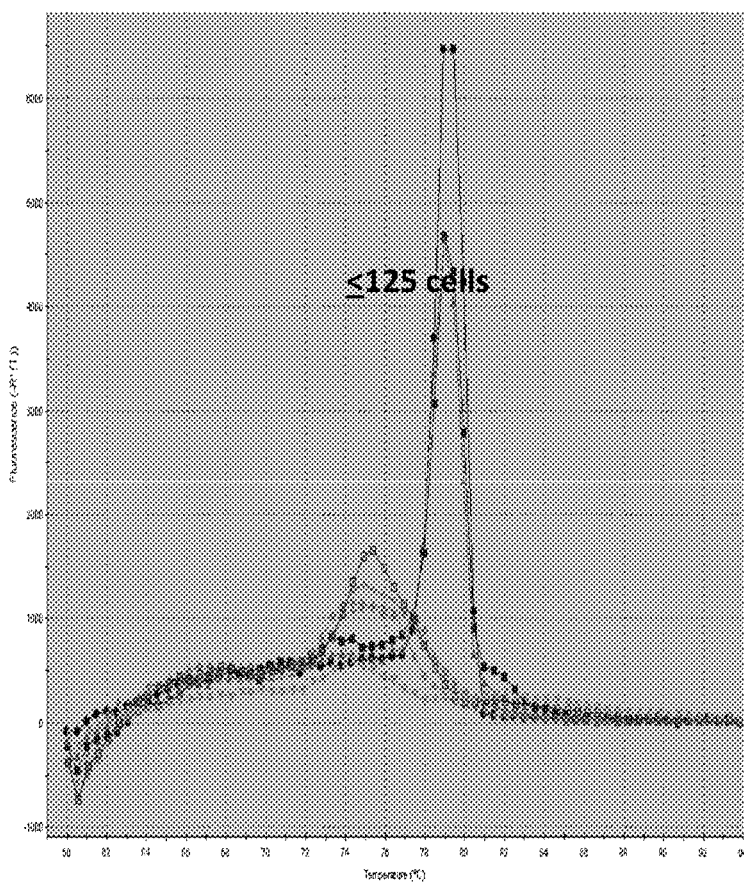
Figure 8C:
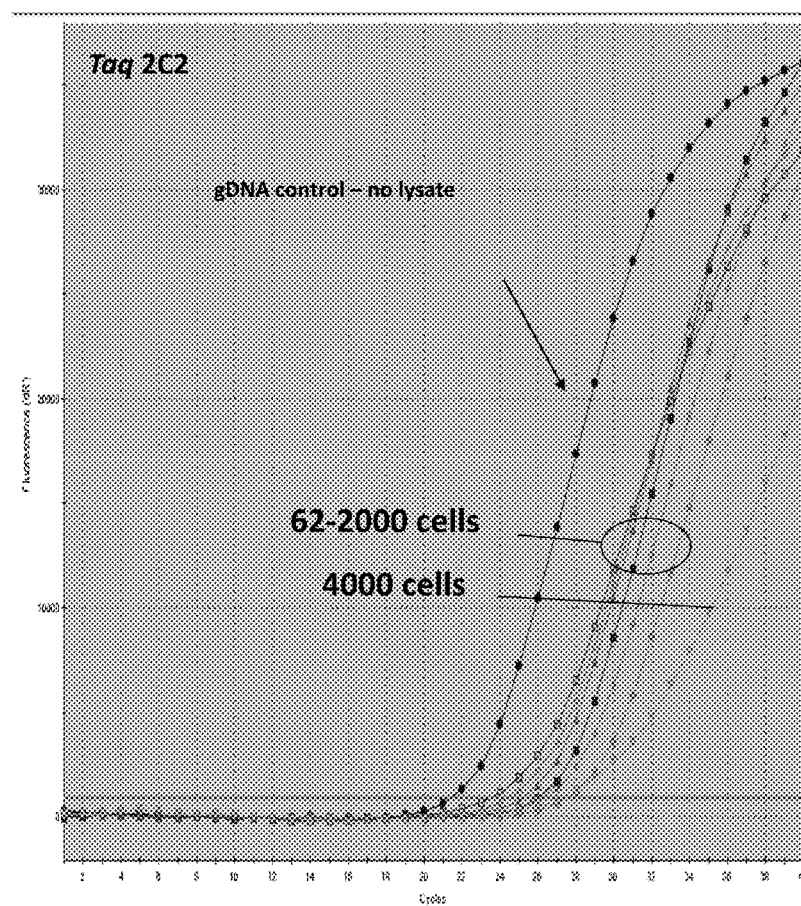
Figure 8D:
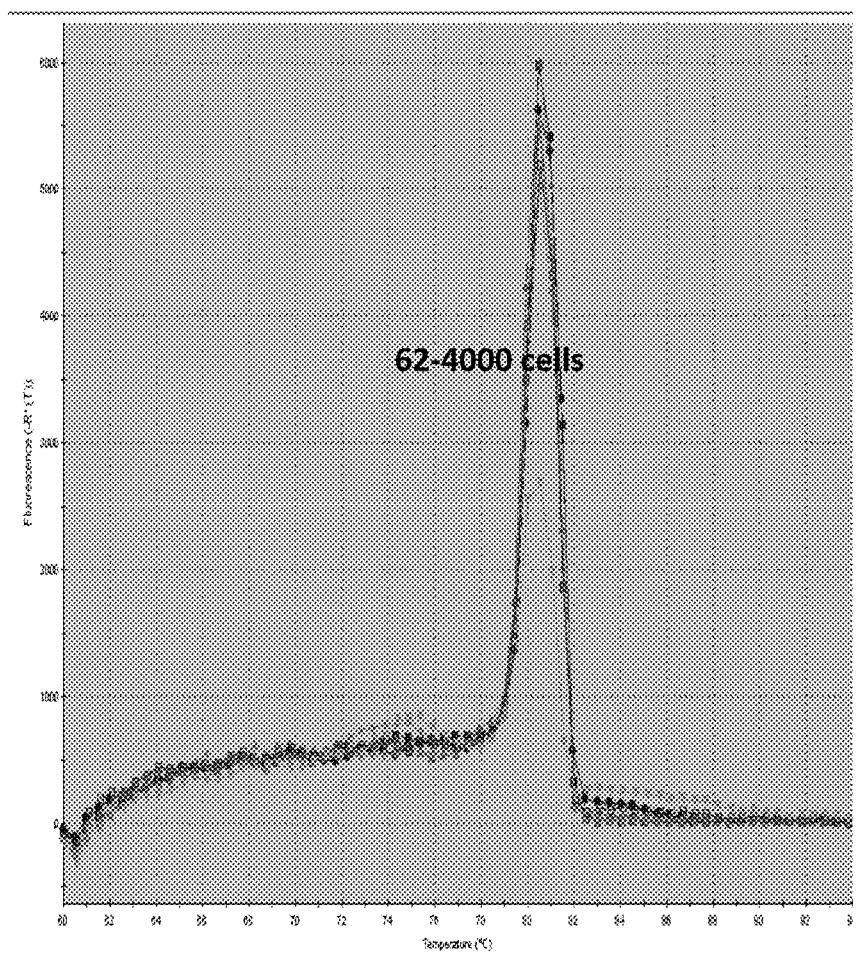

The amplification products were fractionated on an agarose gel pre-stained with ethidium bromide. The results are shown in FIG. 4, in which the first lane is a molecular weight marker, the second through seventh lanes contain amplification products produced from samples with genomic DNA, but lacking blood, and the eighth through thirteenth lanes contain amplification products produced from samples without genomic DNA, but containing 2% blood. Duplicate reactions are shown adjacent to one another on the gel in lanes 2 and 3, 4 and 5, 6 and 7, 8 and 9, 10 and 11, and 12 and 13. As can be seen from FIG. 4, both mutants tested ("Taq42" and "2C2") were able to amplify the target DNA, in the presence or absence of blood, whereas the wild-type Taq DNA polymerase was incapable of amplifying the target DNA in the presence of blood. The figure provides full support for the conclusion that mutant DNA polymerases according to the invention are capable of polymerizing nucleic acid strands in the presence of inhibitors of Taq, and specifically in the presence of blood.

Example 5

Further Characterization of Mutant Activity in the Presence of Inhibitors

The results obtained in Example 4 show that mutants according to the present invention are capable of amplifying a target nucleic acid during End-Point PCR in the presence of blood, whereas wild-type Taq DNA polymerase is not. To characterize the activity of the mutants in more detail, Real-Time PCR was performed on a 322 base-pair target from either purified human genomic DNA or whole blood as template. PCR reactions containing components typical for Real-Time assays were assembled using wild-type Taq (Taq2000, Agilent Technologies), mutant "2C2", or mutant "Taq42". Either 10 ng of purified human genomic DNA or 1 ul human blood (4% final concentration) was added individually as template to enzyme master mixes previously aliquotted into PCR strip tubes. Each polymerase and template combination was assayed in duplicate. Amplification was performed using 10 ng of each enzyme per 25 ul reaction. The thermocycling parameters were as follows: 95° C. for 5 minutes; 95° C. for 12 seconds; and 60° C. for 1 minute; for 45 cycles. The results are depicted in FIG. 5.

More specifically, FIG. 5 depicts Real-Time QPCR amplification plots and the corresponding melt curves comparing amplification of a 322 base-pair target by wild-type Taq and two mutants according to the invention, in the presence of 10 ng of genomic DNA and in the absence of blood (Panels A and B, respectively), or in the presence of 4% (v/v) blood and the absence of genomic DNA (Panels C and D, respectively). For simplicity, the average of duplicate reactions is shown on the amplification plots and melt curves. Panel A shows that, in the absence of blood, all polymerases tested are capable of synthesizing the desired product using the conditions tested. Panel B shows the melt peaks corresponding to the amplification products generated using the different polymerases (the peak for the wild-type enzyme is shifted slightly lower relative to the mutants due to slightly different salt conditions present in these reactions). In contrast to the results depicted in Panel A, the result in Panel C show that wild-type Taq DNA polymerase was not able to amplify the target DNA in a sample containing 4% (v/v) blood/EDTA (i.e., 1 ul of blood in a 25 ul reaction mixture). While the wild-type Taq DNA polymerase was inhibited by the blood, the tested mutants were able to amplify the specific product from the endogenous DNA present in the blood cells when 4% blood was used as template. Panel D confirms that the products amplified by the mutants represented a single amplification species with the expected $T_m$, and that both mutant enzymes produced the same species. Panel D further shows that no specific amplification product was generated by the wild-type Taq DNA polymerase. The data shown in FIG. 5 further support the conclusion that mutant enzymes according to the present invention can function well in the presence of inhibitors of wild-type Taq DNA polymerase.

Example 6

Additional Testing of Activity in Blood

To further characterize the ability of exemplary mutants of the invention to perform in PCR reactions using blood as a sample for DNA template, PCR reactions containing components typical for End-Point assays were assembled using wild-type Taq (Taq2000, Agilent Technologies; SEQ ID NO:4), mutant "2C2" (SEQ ID NO:38), mutant "Taq42" (SEQ ID NO:36), mutant "3B" (SEQ ID NO:28), and mutant "5A2" (SEQ ID NO:22). Either 5 ng of purified human genomic DNA (0% blood) or human blood containing heparin (FIG. 6) or EDTA (FIG. 7), at blood concentrations of 2%, 10%, 15%, 20%, 25%, and 30% (final concentration) was added individually as template to enzyme master mixes previously aliquotted into PCR strip tubes. Amplification was performed using 20 ng of enzyme per 20 ul reaction mix. The thermocycling parameters were as follows: 95° C. for 5 minutes; 95° C. for 20 seconds; and 60° C. for 50 seconds; for 30 cycles.

The results of the amplification reactions are shown in FIG. 6 and FIG. 7. Specifically, these figures show the presence and relative abundance of amplified product from the various reactions. FIG. 6, Panel A, shows that wild-type Taq DNA polymerase is able to amplify a 286 bp product from purified template, but was completely incapable of producing product in the presence of 2%, 10%, or 15% heparin-treated blood. Panels A also shows that, in contrast to the wild-type Taq polymerase, mutant "2C2" was able to produce an essentially equivalent amount of product in the presence of at least 20% heparin-treated blood. Panel B shows that mutant "5A2" is capable of producing wild-type amounts of product in the absence of inhibitors, but shows a rapid loss in activity in the presence of 2% heparin-treated blood, and a total lack of activity in the presence of 10% or more of heparin-treated blood. Panel C shows that mutants "42" ("Taq42") and "3B" are capable of producing high levels of product in the presence of 2% heparin-treated blood, but show a significant reduction in product production at 10% heparin-treated blood.

The results of FIG. 6 provide further support that the mutant DNA polymerases of the invention possess advantageous properties as compared to wild-type DNA polymerases. The data also indicate the superiority of mutant polymerases having one or more mutations in addition to a mutation at residue 507 of Taq.

Turning now to FIG. 7, the results of PCR amplifications of the 286 by aldolase template using the same mutants as in FIG. 6, but using EDTA-treated blood as the sample are shown. Similar to the results for heparin-treated blood, FIG. 7, Panel A, shows that wild-type Taq is capable of producing product from purified "clean" DNA template, but produces very little product in the presence of 2% EDTA-treated blood. Further, as with heparin-treated blood, mutant "5A2" shows little activity in the presence of 2% EDTA-treated blood, although it does show detectable activity at 10% EDTA-treated blood. Panel B shows that mutant "42" has very high activity in the presence of up to 20% EDTA-treated blood. Note that the 2% sample for the reactions relating to mutants "42", "3B", and "2C2" show incorrectly low amounts of product as a result of an unknown processing error. Like mutant "42", Panel C shows that mutants "3B" and especially "2C2" show high polymerase activity in the presence of up to 20% of EDTA-treated blood. It is especially interesting that mutant "2C2" shows high activity in the presence of 25% EDTA-treated blood, and still retains some activity at 30% EDTA-treated blood.

Taken together, the results presented in FIGS. 6 and 7 provide evidence of the superiority of mutants according to the invention in amplifying a target nucleic acid in a "dirty" sample.

Example 7

Mutant Polymerase Activity in the Presence of Cell Lysates

Cell lysates, or more specifically components present in cell lysates, are known to be inhibitors of Taq DNA polymerase activity. To determine whether mutants according to the present invention are resistant to inhibition by cell lysates, Real-Time QPCR reactions were run. The reactions were run as a series of amplifications, using differing amounts of cell lysates in the reaction. PCR reactions containing components typical for Real-Time PCR were assembled using wild-type Taq (Taq2000, Agilent Technologies), mutant "2C2", or mutant "Taq42". Either 10 ng of purified human genomic DNA or cell lysates produced from varying amounts of cells in SideStep lysis and stabilization buffer (Agilent Technologies) were then added individually to enzyme master mixes previously aliquotted into PCR strip tubes. Each polymerase and template combination was assayed in duplicate. To generate the dilution series of cell lysates used as template in this set of reactions, cells were lysed in SideStep buffer (4000 per ul SideStep buffer; SideStep buffer from Agilent Technologies) then serially diluted 1:2 in the same buffer down to 62.5 cells per ul. Amplification was performed using 1 ul of the appropriate template and 10 ng of each enzyme per 25 ul reaction. The thermocycling parameters were as follows: 95° C. for 5 minutes; 95° C. for 15 seconds, 60° C. for 1 minute; and 72° C. for 30 sec; for 40 cycles.

As shown in FIG. 8, Panel A, wild-type Taq DNA polymerase was able to amplify the specific product in the presence of cell lysates representing 125 cells or fewer, but unable to do so in the presence of cell lysates representing 250 or more cells. The melt curve in Panel B shows that amplification in the presence of lysates from 125 or fewer cells was specific, whereas any amplification seen in the presence of lysates from 250 or more cells did not produce a specific product with the appropriate $T_m$. Wild-type Taq DNA polymerase was thus shown to be inhibited by a relatively small amount of cell lysates, consistent with results from others.

In contrast to the activity of wild-type Taq, mutant "2C2" was able to amplify specific product in samples containing cell lysates representing up to 2,000 cells (see FIG. 8, Panel C). The panel further shows that low levels of amplification product was obtained even in the presence of lysates from 4000 cells, the highest amount tested. FIG. 8, Panel D, shows that the amplification product from samples containing lysates representing from 62 to 4000 cells all showed a single species amplified, indicating specific amplification of the target. FIG. 8 thus shows that mutants according to the invention can function well in the presence of cell lysates at levels well exceeding those that inhibit wild-type Taq DNA polymerase.

Example 8

Mutant Activity in the Presence of Inhibitors Derived from Plants

To even further characterize the inhibitor resistance of mutants according to the invention, End-Point PCR reactions were run in the presence of the acidic plant polysaccharide pectin. PCR reactions containing components typical for End-Point PCR were assembled using wild-type Taq (Taq2000, Agilent Technologies), mutant "2C2", or mutant "Taq42". Twenty nanograms of purified human genomic DNA with or without pectin (0.005% final concentration, obtained from Sigma) was added individually as template to enzyme master mixes previously aliquotted into PCR strip tubes. Each polymerase and template combination was assayed in duplicate. Amplification was performed using 1.25 Units of enzyme per 50 ul reaction mix. The thermocycling parameters were as follows: 95° C. for 5 minutes; 95° C. for 30 seconds; 58° C. for 30 seconds; and 72° C. for 60 seconds; for 40 cycles.

Figure 9:
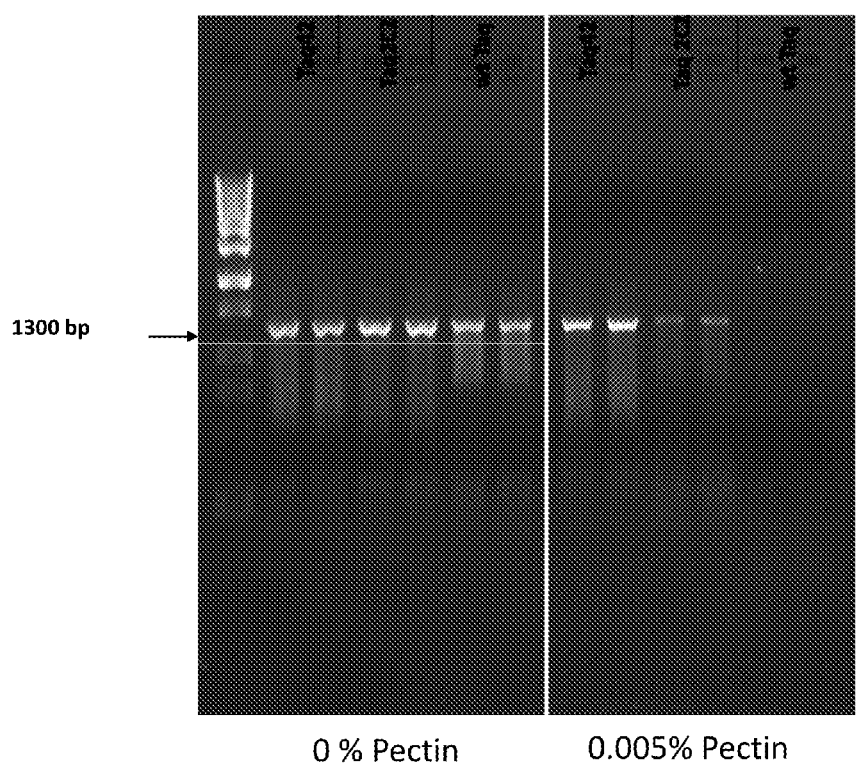
FIG. 9 depicts an agarose gel, showing amplification products obtained from PCR amplification of a 1300 base-pair target in the absence of pectin or the presence of 0.005% pectin. 1.25 Units of enzyme were used per reaction (50 ul) and an amplification scheme was used as follows: 95° C. for 5 minutes followed by 95° C. for 30 seconds, followed by 58° C. for 30 seconds, followed by 72° C. for 60 seconds. The process was repeated for 40 cycles.
Figure 10A:
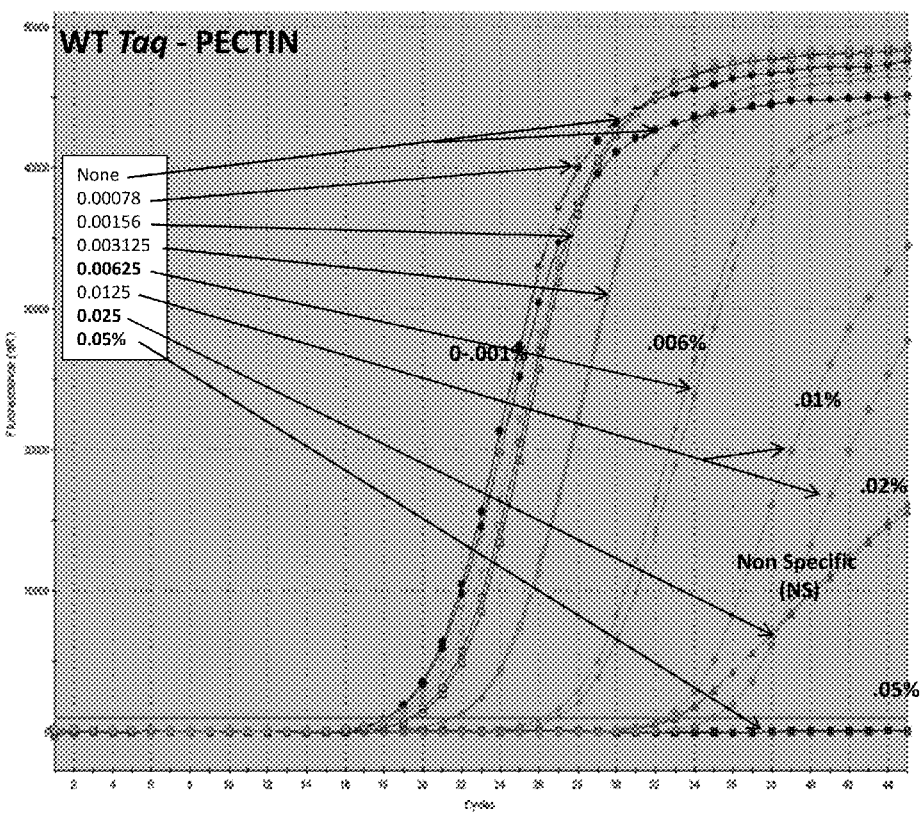
FIG. 10 depicts Real-Time QPCR amplification plots comparing the amplification of a 510 base-pair product by wild-type Taq DNA polymerase and a mutant according to the invention, in the presence of various concentrations of pectin (Panels A and B) or the presence of various concentrations of xylan (Panels C and D).
Figure 10B:
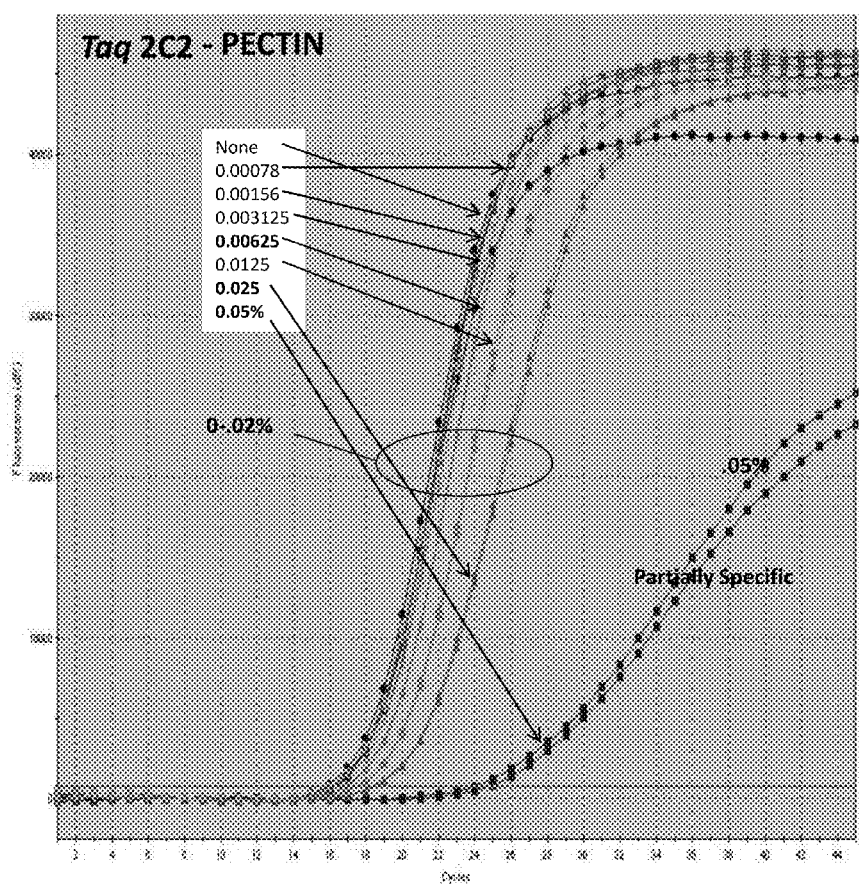
Figure 10C:
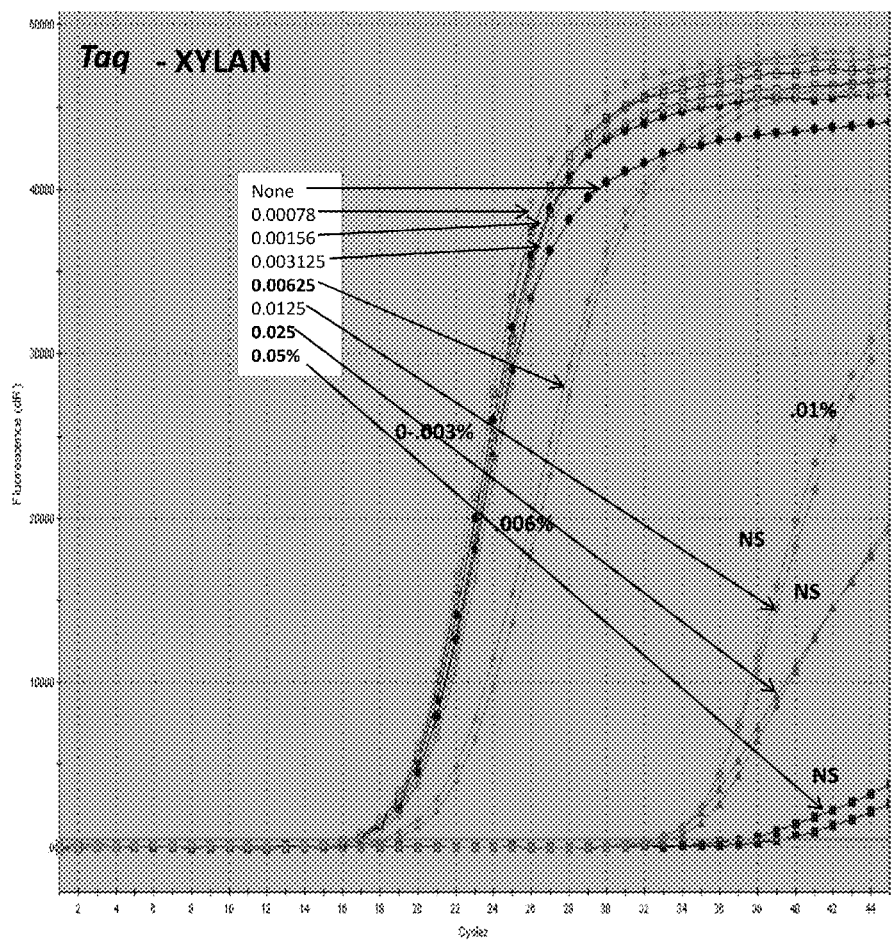
Figure 10D:
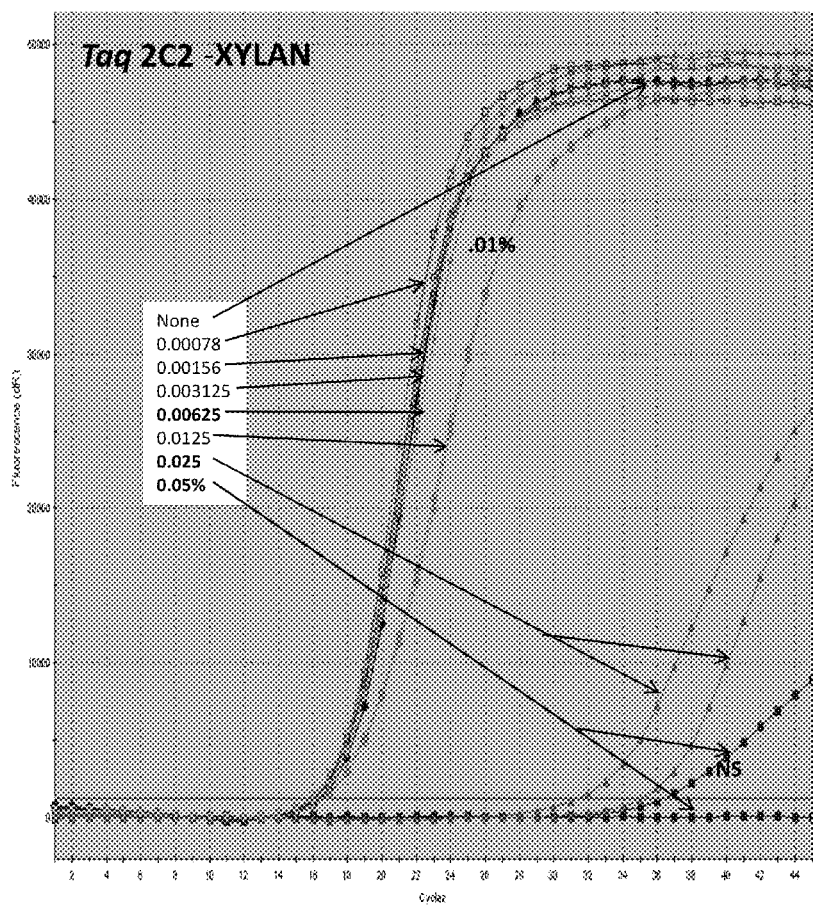

The results of the amplification reactions are depicted in FIG. 9. Amplification products were fractionated through an agarose gel pre-stained with ethidium bromide. In the Figure, lane 1 represents a molecular weight marker ladder, lanes 2 through 7 represent samples from reactions run in the absence of pectin, and lanes 8 through 13 represent samples from reactions run in the presence of 0.005% pectin. Duplicate reactions are shown adjacent to one another on the gel. As can be seen from the figure, two mutant enzymes ("Taq42" and "2C2") and wild-type Taq DNA polymerase were able to amplify the 1300 base-pair target in the absence of pectin. However, in the presence of 0.005% pectin, the wild-type Taq enzyme was not capable of amplifying a detectable product, whereas the "Taq42" mutant showed essentially full activity and the "2C2" mutant showed reduced, but detectable, activity. This figure provides additional support for the conclusion that mutant polymerases according to the present invention are active in the presence of inhibitors of wild-type Taq DNA polymerase.

Example 9

Further Characterization of Resistance to Inhibitors Derived from Plants

The previous Example showed that mutant polymerases of the invention are resistant to inhibitory concentrations of pectin in End-Point PCR, the ability of the mutants to function in the presence of inhibitors derived from pants was further characterized in Real-Time PCR. In this Example, the extent to which mutant "2C2" is resistant to the acidic plant polysaccharides pectin and xylan was determined. Real-Time QPCR reactions were performed independently in the absence or presence of increasing amounts of pectin and xylan. PCR reactions containing components typical for Real-Time PCR were assembled using wild-type Taq (Taq2000, Agilent Technologies), mutant "2C2", or mutant "Taq42". Ten nanograms of purified human genomic DNA with and without different amounts of either pectin or xlyan was added as template individually to enzyme master mixes previously aliquotted into PCR strip tubes. Two-fold serial dilutions of either Xylan or Pectin (in separate experiments, obtained from Sigma) were generated and added individually to PCR reactions prior to amplification. Each polymerase and template combination was assayed in duplicate. PCR was performed using 2 Units of each enzyme per 25 ul reaction. The thermocycling parameters were as follows: 95° C. for 2 minutes; 95° C. for 12 seconds; and 60° C. for 1 minute; for 45 cycles.

FIG. 10 depicts Real-Time QPCR amplification plots comparing amplification of a 510 base-pair target by wild-type Taq DNA polymerase and a mutant according to the invention. Panel A shows amplification by wild-type Taq DNA polymerase in the absence of pectin or in the presence of pectin at concentrations ranging from 0.00078% to 0.05%. As shown, specific product is formed in the presence of up to 0.0125% pectin. Only non-specific products are obtained when the concentration of pectin reaches 0.25% or higher under these conditions (data not shown). In contrast, Panel B shows that specific product was obtained for mutant "2C2" in the presence of at least 0.025% pectin. Amplification at 0.05% pectin was detected, however, the amplification products were found to include both specific and non-specific species (data not shown). The results presented in Panels A and B show that mutant polymerases according to the invention are capable of specific amplification of targets in the presence of concentrations of pectin that inhibit wild-type Taq DNA polymerase.

FIG. 10 further shows the results of amplification reactions in the presence of varying concentrations of xylan. Panel C shows the results of Real-Time QPCR using wild-type Taq DNA polymerase in the absence of xylan and the presence of xylan at concentrations ranging from 0.00078% to 0.05%. As shown in the panel, wild-type Taq DNA polymerase was able to amplify specific product at concentrations of xylan ranging from 0.00078% to 0.006%, but failed to do so at concentrations of xylan at or above 0.0125%. Amplification products detected at xylan concentrations of 0.0125% or above were non-specific amplification products (data not shown). In contrast, mutant "2C2" showed excellent amplification activity in the presence of 0.0125% xylan. The results presented in FIG. 10, Panels C and D, provide further support for the conclusion that mutant DNA polymerases according to the present invention are resistant to inhibitors of wild-type Taq DNA polymerase at levels that inhibit the wild-type enzyme.

It will be apparent to those skilled in the art that various modifications and variations can be made in the practice of the present invention without departing from the scope or spirit of the invention. Other embodiments of the invention will be apparent to those skilled in the art from consideration of the specification and practice of the invention. It is intended that the specification and examples be considered as exemplary only, with a true scope and spirit of the invention being indicated by the following claims.

The invention claimed is:

1. A mutant thermostable Type-A DNA polymerase consisting of or comprising:
  a first mutation at residue 507 of wild-type Taq DNA polymerase, which has the sequence of SEQ ID NO:4, or at a residue corresponding to residue 507 of wild-type Taq DNA polymerase in another thermostable Type-A DNA polymerase; and at least one additional mutation at a residue selected from 59, 155, 245, 375, 508, 734, and 749 of wild-type Taq DNA polymerase, or at a corresponding residue in another thermostable Type-A DNA polymerase,
  wherein the combination of mutations provides a mutant polymerase that possesses a faster polymerization rate and a higher resistance to polymerization activity inhibitors than the wild-type DNA polymerase from which it is derived.

2. The mutant of claim 1, wherein the mutant DNA polymerase is a mutant Taq DNA polymerase, which comprises an E507K mutation as the first mutation.

3. The mutant of claim 1, which is a mutant Taq DNA polymerase and which comprises mutations at the following residues: G59, V155, L245, L375, E507, E734, and F749.

4. The mutant of claim 3, which comprises the following mutations: G59W, V155A, L245M, L375V, E507K, E734G, and F749I.

5. The mutant of claim 1, which is a mutant of a thermostable Type-A DNA polymerase other than Taq DNA polymerase and which comprises mutations at residues corresponding to the following residues of Taq DNA polymerase: G59, V155, L245, L375, E507, E734, and F749.

6. The mutant of claim 1, which is a mutant Taq DNA polymerase and which comprises mutations at the following residues: G59, L245, L375, E507, K508, E734, and F749.

7. The mutant of claim 6, which comprises the following mutations: G59W, L245M, L375V, E507K, K508R, E734G, and F749I.

8. The mutant of claim 1, which is a mutant of a thermostable Type-A DNA polymerase other than Taq DNA polymerase and which comprises mutations at residues corresponding to the following residues of Taq DNA polymerase: G59, L245, L375, E507, K508, E734, and F749.

9. The mutant of claim 1, which comprises mutations at the following residues of Taq DNA polymerase: L245, E507, and F749, or at corresponding residues in another thermostable Type-A DNA polymerase.

10. The mutant of claim 1, which comprises mutations at the following residues of Taq DNA polymerase: L245, L375, E507, E734, and F749, or at corresponding residues in another thermostable Type-A DNA polymerase.

11. The mutant of claim 1, consisting of or comprising the sequence of SEQ ID NO:12, SEQ ID NO:14, SEQ ID NO:16, SEQ ID NO:18, SEQ ID NO:20, SEQ ID NO:24, SEQ ID NO:26, SEQ ID NO:28, SEQ ID NO:30, SEQ ID NO:32, SEQ ID NO:34, SEQ ID NO:36, or SEQ ID NO:38, wherein the polymerase possesses a faster polymerization activity than wild-type Taq polymerase and is resistant to inhibitors of wild-type Taq polymerase.

12. A kit for amplification of a target nucleic acid, said kit comprising the mutant DNA polymerase of claim 1 and packaging materials therefor.

13. A method of polymerization of a target nucleic acid from a primer that specifically binds to the target nucleic acid, said method comprising:
  combining the primer with the target nucleic acid and the mutant thermostable Type-A DNA polymerase of claim 1,
  wherein the mutant thermostable Type-A DNA polymerase consists of or comprises:
  a first mutation at residue 507 of wild-type Taq DNA polymerase or at a residue corresponding to residue 507 of wild-type Taq DNA polymerase in another thermostable Type-A DNA polymerase; and
  at least one additional mutation at a residue selected from 59, 155, 245, 375, 508, 734, and 749 of wild-type Taq DNA polymerase, or at a corresponding residue in another thermostable Type-A DNA polymerase,
  wherein the combination of mutations provides a mutant polymerase that possesses a faster polymerization rate and a higher resistance to polymerization activity inhibitors than the wild-type DNA polymerase from which it is derived, and
  providing conditions under which the polymerase extends the primer using the sequence of the target as a template for incorporation of nucleotides.

14. The method of claim 13, which is a method of PCR.

15. The method of claim 14, which is a method of fast PCR.

16. The method of claim 13, wherein the conditions include the presence of an inhibitor of the wild-type DNA polymerase at a concentration that is inhibitory to the wild-type DNA polymerase.

17. The method of claim 13, wherein the target nucleic acid is present in blood or a fraction of blood.

18. The method of claim 13, wherein the target nucleic acid is present in plant material or a sample containing plant material.

\* \* \* \* \*